(12) United States Patent
Won

(10) Patent No.: US 12,234,458 B2
(45) Date of Patent: Feb. 25, 2025

(54) COMPOSITION FOR INHIBITING CTGF EXPRESSION

(71) Applicant: LEMONEX INC., Seoul (KR)

(72) Inventor: Cheol Hee Won, Seoul (KR)

(73) Assignee: LEMONEX INC., Seoul (KR)

( * ) Notice: Subject to any disclaimer, the term of this patent is extended or adjusted under 35 U.S.C. 154(b) by 1065 days.

(21) Appl. No.: 17/162,045

(22) Filed: Jan. 29, 2021

(65) Prior Publication Data

US 2021/0230602 A1 Jul. 29, 2021

Related U.S. Application Data

(63) Continuation of application No. PCT/KR2019/095026, filed on Jun. 3, 2019.

(60) Provisional application No. 62/712,317, filed on Jul. 31, 2018.

(30) Foreign Application Priority Data

Jun. 3, 2019 (KR) .......................... 10-2019-0065618

(51) Int. Cl.
*C12N 15/113* (2010.01)
*A61K 9/16* (2006.01)
*A61P 17/02* (2006.01)
*C07K 14/00* (2006.01)

(52) U.S. Cl.
CPC ........ *C12N 15/1136* (2013.01); *A61K 9/1611* (2013.01); *A61P 17/02* (2018.01); *C07K 14/003* (2013.01); *C12N 2310/14* (2013.01); *C12N 2310/3181* (2013.01); *C12N 2310/351* (2013.01)

(58) Field of Classification Search
CPC ............ C12N 15/1136; C12N 2310/14; C12N 2310/3181; C12N 2310/351; A61K 9/1611; A61P 17/02; C07K 14/003
See application file for complete search history.

(56) References Cited

U.S. PATENT DOCUMENTS

| | | | |
|---|---|---|---|
| 9,340,786 B2 | 5/2016 | Khvorova et al. | |
| 2008/0108583 A1 | 5/2008 | Feinstein | |
| 2010/0130595 A1 | 5/2010 | Dean et al. | |
| 2014/0113950 A1* | 4/2014 | Khvorova ................. | A61P 1/00 536/24.5 |
| 2019/0071314 A1* | 3/2019 | Min ....................... | A61K 9/501 |

FOREIGN PATENT DOCUMENTS

| | | |
|---|---|---|
| CN | 101160138 A | 4/2008 |
| CN | 101884789 A | 11/2010 |
| CN | 105462975 A | 4/2016 |
| CN | 108251420 A | 7/2018 |
| EP | 3 173 074 A1 | 5/2017 |
| EP | 3018209 B1 | 10/2019 |
| EP | 3831392 A1 | 6/2021 |
| KR | 10-2014-0010285 A | 1/2014 |
| KR | 10-2016-0011565 A | 2/2016 |
| KR | 10-1697396 B1 | 1/2017 |
| WO | WO 2003/053340 A3 | 3/2004 |
| WO | WO 2010/042281 A2 | 4/2010 |
| WO | WO 2010/107952 A2 | 9/2010 |
| WO | WO 2011/119887 A1 | 9/2011 |
| WO | WO 2014/207199 A1 | 12/2014 |
| WO | WO 2017/178883 A2 | 10/2017 |

OTHER PUBLICATIONS

Dharmacon Research Inc., Technical Bulletin #003-Revision A, "siRNA Oligonucleotides for RNAi Applications", Aug. 20, 2001, pp. 1-12, Retrieved from the Internet: <http://www.dharmacon.com/tech/tech003.html>. (Year: 2001).*
Knezevic (Dissertation, Iowa State Univ; Functionalized mesoporous silica nanoparticles for stimuli-responsive and targeted drug delivery, 2009, pp. 1-104). (Year: 2009).*
Office action issued on Feb. 22, 2022 from Japan Intellectual Property Office in a counterpart Japanese Patent Application No. 2021-505193 (all the cited references are listed in this IDS.)(English translation is also submitted herewith.).
S Kondo et al., "Characterization of a mouse ctgf 3'-UTR segment that mediates repressive regulation of gene expression", Biochemical and Biophysical Research Communications, 2000, and vol. 278. pp. 119-124.
J George et al., "siRNA-mediated knockdown of connective tissue growth factor prevents N-nitrosodimethylamine-induced hepatic fibrosis in rats", Gene Therapy, 2007, and vol. 14 and pp. 790-803.
Guangming Li et al., "Inhibition of connective tissue growth factor by siRNA prevents liver fibrosis in rats", The Journal of Gene Medicine, 2006, and vol. 8 and pp. 889-900.
Office action issued on Oct. 30, 2023 from Korean Patent Office in a counterpart Korean Patent Application No. 10-2023-0089843 (all the cited references are listed in this IDS.) (English translation is also submitted herewith.).
Helen L. Lightfoot et al., "Target mRNA inhibition by oligonucleotide drugs in man", Nucleic Acids Research, vol. 40, No. 21. pp. 10585-10595, 2012.
Office action issued on Mar. 30, 2021 from Korean Patent Office in a counterpart Korean Patent Application No. 10-2019-0065618 (all the cited references are listed in this IDS.) (English translation is also submitted herewith.).

(Continued)

*Primary Examiner* — Brian Whiteman
*Assistant Examiner* — Stephanie L Sullivan
(74) *Attorney, Agent, or Firm* — The PL Law Group, PLLC

(57) ABSTRACT

A composition according to an embodiment of the present invention includes nucleic acid molecules which are capable of effectively inhibiting the expression level of connective tissue growth factor (CTGF) and collagen by RNA interference (RNAi), thereby preventing or treating a variety of fibroproliferative diseases due to overexpression of CTGF or collagen.

10 Claims, 27 Drawing Sheets

Specification includes a Sequence Listing.

(56) References Cited

OTHER PUBLICATIONS

Examination Report issued on May 9, 2022 from Australia Intellectual Property Office in a counterpart Australian Patent Application No. 2019314093 (all the cited references are listed in this IDS.).
International Search Report for PCT/KR2019/095026 mailed on Sep. 10, 2019.
European Search Report For EP19843450.8 issued on Jul. 18, 2022 from European patent office in a counterpart European patent application.
Hwang Jihye et al., "Development of Cell-Penetrating Asymmetric Interfering RNA Targeting Connective Tissue Growth Factor", Journal of Investigative Dermatology, vol. 136, No. 11, Aug. 16, 2016, pp. 2305-2313, XP055876531.
Cho Ki-Hyun et al., "Local Delivery of CTGF siRNA with Poly(sorbitol-co-PEI) Reduces Scar Contraction in Cutaneous Wound Healing", Tissue Engineering and Regenerative Medicine, vol. 14, No. 3, May 12, 2017, pp. 211-220, XP036252134, ISSN: 1738-2696, DOI: 10.1007/S13770-017-0059-9.
Keasberry N A et al., "Mesoporous Silica Nanoparticles as a Carrier Platform for Intracellular Delivery of Nucleic Acids", Biochemistry, vol. 82, No. 6, Mar. 6, 2017, pp. 655-662, XP036260228, ISSN: 0006-2979, DOI: 10.1134/S0006297917060025.
Rafael R. Castillo et al., "Recent applications of the combination of mesoporous silica nanoparticles with nucleic acids: development of bioresponsive devices, carriers and sensors", Biomaterials Science, vol. 5, No. 3, Jan. 20, 2017, pp. 353-377, XP055643393, GB ISSN: 2047-4830, DOI: 10.1039/C6BM00872K.

* cited by examiner

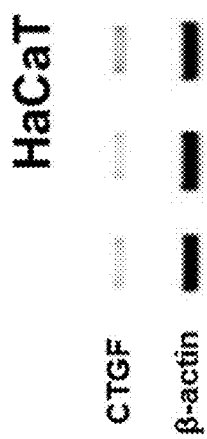
FIG. 17B HaCaT
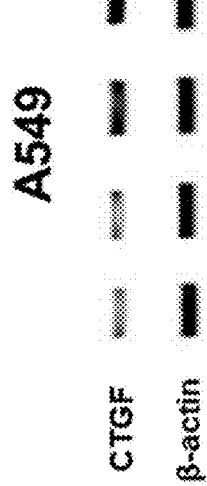
FIG. 17A A549

$t_{50\%}$ = about 2.5 days

COMPOSITION FOR INHIBITING CTGF EXPRESSION

CROSS REFERENCE TO RELATED APPLICATIONS AND CLAIM OF PRIORITY

The present application is a continuation application to International Application No. PCT/KR2019/095026 with an International Filing Date of Jun. 3, 2019, which claims the benefit of U.S. Application No. 62/712,317 filed on Jul. 31, 2018 and Korean Patent Application No. 10-2019-0065618 filed on Jun. 3, 2019 at the Korean Intellectual Property Office, the disclosures of which are incorporated by reference herein in their entirety.

REFERENCE TO AN ELECTRONIC SEQUENCE LISTING

A sequence listing electronically submitted with the present application on Jan. 29, 2021 as an ASCII text file named 20210129_Q45020LC42_TU_SEQ.TXT, created on Jan. 21, 2021 and having a size of 25,000 bytes, is incorporated herein by reference in its entirety.

BACKGROUND

1. Technical Field

The present invention relates to a composition that inhibits CTGF expression with high efficiency and has excellent prophylactic or therapeutic effects on fibroproliferative diseases.

2. Background Art

Tissue remodeling is to reconstruct existing tissues in response to physiological or pathological stress. The tissue remodeling in pathophysiology is characterized by connective tissue growth factor (CTGF), myofiber differentiation and activation, deposition of extracellular matrix (ECM) and overexpression of fibrosis. Among various signal molecules and factors, CTGF has been considered as an essential mediator in tissue remodeling. CTGF participates in diverse signal transduction pathways, resulting in cell adhesion and migration, ECM remodeling and alteration of organ structures. The tissue remodeling and fibrosis are associated with numerous fibrotic disorders such as pulmonary fibrosis, liver fibrosis, kidney fibrosis, diabetic retinopathy, and skin fibrosis (keloids and hypertrophic scars).

A process of healing wound in the skin is very complicated and consists of overlapping steps of inflammation, cell differentiation and proliferation, and tissue remodeling (including collagen production). Some cytokines and growth factors, especially TGF-β, play an important role in early and late stages of wound healing. TGF-β mediates leukocyte migration, angiogenesis, fibroblast migration and ECM components (collagen and fibronectin) production through CTGF upregulation. Since overexpression of CTGF has been observed in patients with hypertrophic scars and keloid, suppression of CTGF expression is an attractive strategy to modulate fibrosis mechanisms that can inhibit or reverse the fibrosis process.

Many antibodies or antisense oligonucleotides have been investigated in terms of functions to inhibit CTGF expression or to reduce excessive collagen production and fibrosis. siRNA is one of the promising candidates for CTGF inhibition. RNA interference induced by siRNA is mediated by a highly specific and efficient gene silencing tool that recognizes a target mRNA complementary to sequence and cleaves the same. Despite high potential of the above materials as a new therapeutic agent, there are several limitations and obstacles such as 1) rapid degradation by nucleases in biological systems, 2) difficulty in maintenance of effective siRNA doses, 3) difficulty in efficient delivery across biological barriers.

To date, cationic polymers, lipid nanoparticles (LNPs), viruses, and various nanomaterials have been developed for delivery of siRNAs. The clinical application of cationic polymers and LNPs should be carefully implemented due to toxicity and/or instability of structures in vivo, and viral gene transfer causes mutagenesis in addition to low packaging capacity. Chemical modification of siRNA backbones can increase stability and cell uptake, but may still suffer from disadvantages such as high expense, labor intensive and time consuming process, and administration of high amount of siRNA for achieving satisfactory efficacy in target cells.

SUMMARY

An object of the present invention is to provide a composition with high efficiency of inhibiting CTGF expression and excellent prophylactic or therapeutic effects on fibroproliferative diseases.

To achieve the above objects, the following technical solutions are adopted in the present invention.

1. A composition for inhibiting CTGF gene expression, including a nucleic acid molecule comprised of a sequence having complementarity of 10 nucleotides or more to a sequence of SEQ ID NO: 1.

2. The composition according to the above 1, wherein the nucleic acid molecule consists of a sequence having complementarity of 16 nucleotides or more to the sequence of SEQ ID NO: 1.

3. The composition according to the above 1, wherein the nucleic acid molecule consists of a sequence complementary to the entire sequence of SEQ ID NO: 1.

4. The composition according to the above 1, wherein the nucleic acid molecule forms a strand of siRNA, dsRNA, PNA or miRNA.

5. The composition according to the above 4, wherein the composition includes at least one siRNA or dsRNA selected from the group consisting of: siRNA comprised of a sense RNA having the sequence of SEQ ID NO: 1 and an antisense RNA having the sequence of SEQ ID NO: 2; dsRNA comprised of a strand having a sequence of SEQ ID NO: 3 and another strand complementary thereto; siRNA comprised of a sense RNA having a sequence of SEQ ID NO: 52 and an antisense RNA having a sequence of SEQ ID NO: 53; dsRNA comprised of a strand having a sequence of SEQ ID NO: 54 and another strand complementary thereto; siRNA comprised of a sense RNA having a sequence of SEQ ID NO: 55 and an antisense RNA having a sequence of SEQ ID NO: 56; dsRNA comprised of a strand having a sequence of SEQ ID NO: 57 and another strand complementary thereto; siRNA comprised of a sense RNA having a sequence of SEQ ID NO: 58 and an antisense RNA having a sequence of SEQ ID NO: 59; dsRNA comprised of a strand having a sequence of SEQ ID NO: 60 and another strand complementary thereto; siRNA comprised of a sense RNA having a sequence of SEQ ID NO: 61 and an antisense RNA having a sequence of SEQ ID NO: 62; dsRNA comprised of a strand having a sequence of SEQ ID NO: 63 and another strand complementary thereto, siRNA comprised of a sense RNA having a sequence of SEQ ID NO: 64 and an antisense RNA having a sequence of SEQ ID NO: 65; dsRNA comprised a strand having a sequence of SEQ ID NO: 66 and another strand complementary thereto: siRNA comprised of a sense RNA having a sequence of SEQ ID NO: 67 and an antisense RNA having a sequence of SEQ ID NO: 68; dsRNA comprised of a strand having a sequence of SEQ ID NO: 69 and another strand complementary thereto; siRNA comprised of a sense RNA having a sequence of SEQ ID NO: 70 and an antisense RNA having a sequence of SEQ ID NO: 71; and dsRNA comprised of a strand having a sequence of SEQ ID NO: 72 and another strand complementary thereto.

6. The composition according to the above 5, further including a sequence of UU or dTdT at 3'-terminals of the sense RNA and the antisense RNA sequence.

7. The composition according to the above 4, further including at least one PNA comprised of one sequence selected from the group consisting of sequences of SEQ ID NO: 87 to SEQ ID NO: 99.

8. The composition according to the above 7, wherein at least one terminal of the PNA is further bound to a peptide having at least one sequence selected from the group consisting of SEQ ID NO: 101 to SEQ ID NO: 107, or mPEG$_{5000}$.

9. A pharmaceutical composition for prevention or treatment of fibroproliferative diseases, including the composition according to any one of the above 1 to 8.

10. The composition according to the above 9, wherein the fibroproliferative disease is at least one selected from the group consisting of hypertrophic scar, keloid, fibrosis, pulmonary fibrosis, idiopathic pulmonary fibrosis, liver fibrosis, kidney fibrosis, cystic fibrosis, myelofibrosis, post-peritoneal fibrosis, scleroderma, diabetic retinopathy, Duken's muscular dystrophy, radiation-induced fibrosis, myocardial fibrosis, diabetic kidney disease, chronic renal failure, chronic viral hepatitis, biliary fibrosis, fatty hepatitis, alcoholic steatohepatitis, nonalcoholic steatohepatitis, proliferative vitreoretinopathy, musculoskeletal tumor, osteosarcoma, rhabdomyosarcoma, glioblastoma, lung cancer, ovarian cancer, esophageal cancer, colon cancer, pancreatic cancer, renal sclerosis, sarcoidosis, glaucoma, macular degeneration, subretinal fibrosis, choroidal angiogenesis, vitreoretinopathy, proliferative vitreoretinopathy, diabetic retinopathy, keratitis, pterygium, ophthalmology disease, scleroderma, uterine fibroids, systemic sclerosis, glomerulonephritis, human immuno-deficient viral renal disease, acute respiratory distress syndrome, chronic obstructive pulmonary disease, Raynaud's disease, rheumatoid arthritis, polymyositis, vascular stenosis, periodontitis and periodontal gingiva.

11. A composition for inhibiting CTGF gene expression, including: porous silica particles carrying nucleic acid molecules that complementarily bind to at least a portion of a transcript of CTGF gene,
wherein the porous silica particles are prepared by: reacting silica particles having pores with a pore diameter of less than 5 nm with a swelling agent at 120 to 180° C. for 24 to 96 hours to expand the pores with a pore diameter of less than 5 nm; and calcining the silica particles having expanded pores at a temperature of 400° C. or higher for at least 3 hours,
wherein an average diameter of the porous silica particles ranges from 100 to 1000 nm, a BET surface area ranges from 200 to 700 m$^2$/g, and a volume per gram ranges from 0.7 to 2.2 ml, and
wherein the porous silica particles are characterized in that t, at which an absorbance ratio in the following Equation 1 becomes 1/2, is 24 or more, $$A_t/A_0 \quad \text{[Equation 1]}$$

wherein $A_0$ is absorbance of the porous silica particles measured by putting 5 ml of suspension containing 1 mg/ml of porous silica particles into a cylindrical permeable membrane having pores with a pore diameter of 50 kDa,
15 ml of the same solvent as the suspension comes into contact with an outside of the permeable membrane, and the inside/outside of the permeable membrane are horizontally stirred at 60 rpm and at 37° C.,
pH of the suspension is 7.4, and
$A_t$ indicates absorbance of the porous silica particle measured after lapse of "t" hours since $A_o$ was measured.

12. The composition according to the above 11, wherein the porous silica particles are positively charged or uncharged at neutral pH on an outer surface thereof or an inside of the pores.

13. The composition according to the above 11, wherein the porous silica particles have hydrophilic or hydrophobic functional groups.

14. The composition according to the above 11, the nucleic acid molecule is complementary to a sequence of SEQ ID NO: 1 with complementarity of 10 nucleotides or more.

15. The composition according to the above 11, the nucleic acid molecule is complementary to the sequence of SEQ ID NO: 1 with complementarity of 16 nucleotides or more.

16. The composition according to the above 11, wherein the nucleic acid molecule consists of a sequence complementary to the entire sequence of SEQ ID NO: 1.

17. The composition according to the above 11, wherein the nucleic acid molecule forms a strand of siRNA, dsRNA, PNA or miRNA.

18. The composition according to the above 17, wherein the composition includes at least one siRNA or dsRNA selected from the group consisting of: siRNA comprised of a sense RNA having the sequence of SEQ ID NO: 1 and an antisense RNA having the sequence of SEQ ID NO: 2; dsRNA comprised of a strand having a sequence of SEQ ID NO: 3 and another strand complementary thereto, siRNA comprised of a sense RNA having a sequence of SEQ ID NO: 52 and an antisense RNA having a sequence of SEQ ID NO: 53; dsRNA comprised of a strand having a sequence of SEQ ID NO: 54 and another strand complementary thereto; siRNA comprised of a sense RNA having a sequence of SEQ ID NO: 55 and an antisense RNA having a sequence of SEQ ID NO: 56; dsRNA comprised of a strand having a sequence of SEQ ID NO: 57 and another strand complementary thereto; siRNA comprised of a sense RNA having a sequence of SEQ ID NO: 58 and an antisense RNA having a sequence of SEQ ID NO: 59; dsRNA comprised of a strand having a sequence of SEQ ID NO: 60 and another strand complementary thereto; siRNA comprised of a sense RNA having a sequence of SEQ ID NO: 61 and an antisense RNA having a sequence of SEQ ID NO: 62; dsRNA comprised of a strand having a sequence of SEQ ID NO: 63 and another strand complementary thereto; siRNA comprised of a sense RNA having a sequence of SEQ ID NO: 64 and an antisense RNA having a sequence of SEQ ID NO: 65; dsRNA comprised a strand having a sequence of SEQ ID NO: 66 and another strand complementary thereto; siRNA comprised of a sense RNA having a sequence of SEQ ID NO: 67 and an antisense RNA having a sequence of SEQ ID NO: 68; dsRNA comprised of a strand having a sequence of SEQ ID NO: 69 and another strand complementary thereto; siRNA comprised of a sense RNA having a sequence of SEQ ID NO: 70 and an antisense RNA having a sequence of SEQ ID NO: 71; and dsRNA comprised of a strand having a sequence of SEQ ID NO: 72 and another strand complementary thereto.

19. The composition according to the above 18, further including a sequence of UU or dTdT at 3'-terminals of the sense RNA and the antisense RNA sequence.

20. The composition according to the above 17, further including at least one PNA comprised of one sequence selected from the group consisting of sequences of SEQ ID NO: 87 to SEQ ID NO: 99.

21. The composition according to the above 20, wherein at least one terminal of the PNA is further bound to a peptide having at least one sequence selected from the group consisting of SEQ ID NO: 101 to SEQ ID NO: 107, or mPEG$_{5000}$.

22. A pharmaceutical composition for prevention or treatment of fibroproliferative diseases, including the composition according to any one of the above 11 to 21.

23. The composition according to the above 22, wherein the fibroproliferative disease is at least one selected from the group consisting of: hypertrophic scar, keloid, fibrosis, pulmonary fibrosis, idiopathic pulmonary fibrosis, liver fibrosis, kidney fibrosis, cystic fibrosis, myelofibrosis, post-peritoneal fibrosis, scleroderma, diabetic retinopathy, Duken's muscular dystrophy, radiation-induced fibrosis, myocardial fibrosis, diabetic kidney disease, chronic renal failure, chronic viral hepatitis, biliary fibrosis, fatty hepatitis, alcoholic steatohepatitis, nonalcoholic steatohepatitis, proliferative vitreoretinopathy, musculoskeletal tumor, osteosarcoma, rhabdomyosarcoma, glioblastoma, lung cancer, ovarian cancer, esophageal cancer, colon cancer, pancreatic cancer, renal sclerosis, sarcoidosis, glaucoma, macular degeneration, subretinal fibrosis, choroidal angiogenesis, vitreoretinopathy, proliferative vitreoretinopathy, diabetic retinopathy, keratitis, pterygium, ophthalmology disease, scleroderma, uterine fibroids, systemic sclerosis, glomerulonephritis, human immuno-deficient viral renal disease, acute respiratory distress syndrome, chronic obstructive pulmonary disease, Raynaud's disease, rheumatoid arthritis, polymyositis, vascular stenosis, periodontitis and periodontal gingiva.

A composition of the present invention includes nucleic acid molecules capable of effectively inhibiting expression of CTGF and collagen, thereby preventing or treating a variety of fibroproliferative diseases due to overexpression of CTGF or collagen.

BRIEF DESCRIPTION OF THE DRAWINGS

FIGS. 8 to 10 illustrate measured results of mRNA expression levels of CTGF and collagen types 1 and 3 at day 16 using RT-PCR; FIG. 11 illustrates comparison of skin irregularities and softness in images of wounded mouse skin between LEM-S401 treated group and the control (buffer, DEGRADABALL only, siCTGF only); FIG. 12 illustrates fluorescent images of skin sections treated with LEM-S401, free siCTGF, DEGRADABALL only and buffer, respectively, after tissue staining the skin sections with antibodies to recognize CTGF and collagen types 1 and 3, respectively, followed by treatment of the skin sections with secondary antibody (Scale bar: 100 μm); and FIGS. 13 to 15 illustrates quantitative analysis results of immunohistochemical data based on the images shown in FIG. 12 (* $P<0.05$,  $P<0.01$, * $P<0.005$).

FIGS. 17A and 17B are graphs illustrating results of treatment of A549 and HaCaT cells, respectively, with 2 ng/ml of TGF-ß for 24 hours, wherein cells were harvested at different time points, and CTGF expression levels were analyzed by RT-PCR.

FIGS. 18 to 20 illustrate measured results of mRNA expression levels of CTGF and collagen types 1 and 3 in the injection site by RT-PCR: FIG. 21 illustrates fluorescent images of CTGF and collagen types 1 and 3 of the obtained mouse skin, which were measured by an immunohistochemical method (Scale bar: 100 μm), and FIGS. 22 to 24 illustrate quantified results of immunohistochemical data ($P<0.05$,  $P<0.01$, * $P<0.005$).

FIGS. 26A to 27B are diagrams illustrating CTGF expression level inhibitory abilities in vivo in AT549 and HaCaT cells with regard to: siRNA (#1) comprised of a sense RNA having a sequence of SEQ ID NO: 1 and an antisense RNA having a sequence of SEQ ID NO: 2; siRNA (#2) comprised of a sense RNA having a sequence of SEQ ID NO: 4 and an antisense RNA having a sequence of SEQ ID NO: 5; siRNA (#3) comprised of a sense RNA having a sequence of SEQ ID NO: 7 and an antisense RNA having a sequence of SEQ ID NO:8, specifically: FIGS. 26A and 26B illustrate results of TGF-ß treatment, 12 hours after siRNA treatment; and FIGS. 27A and 27B illustrate results of siRNA treatment, 24 hours after TGF-ß treatment.

DDV (Degradable Delivery Vehicle) is the particles according to an embodiment, wherein the number in parenthesis means the diameter of the particle and the number of subscripts means the pore diameter. For example, DDV $200_{10}$ refers to a particle having a particle diameter (that is, particle size) of 200 nm and a pore diameter of 10 nm according to an embodiment.

Figure 33:
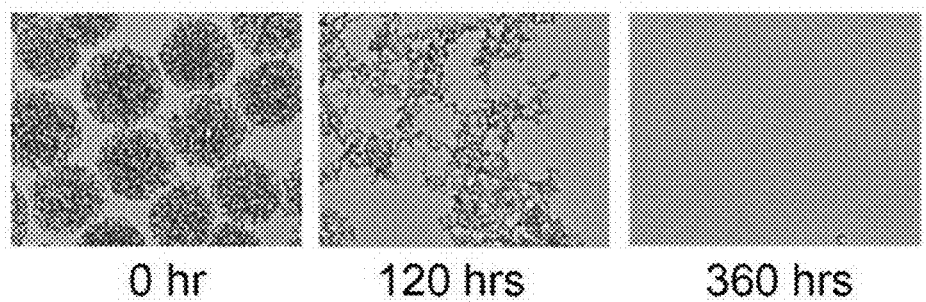

FIG. 33 is micrographs to identify biodegradability of the porous silica particles according to one embodiment of the present invention.

Figure 34:
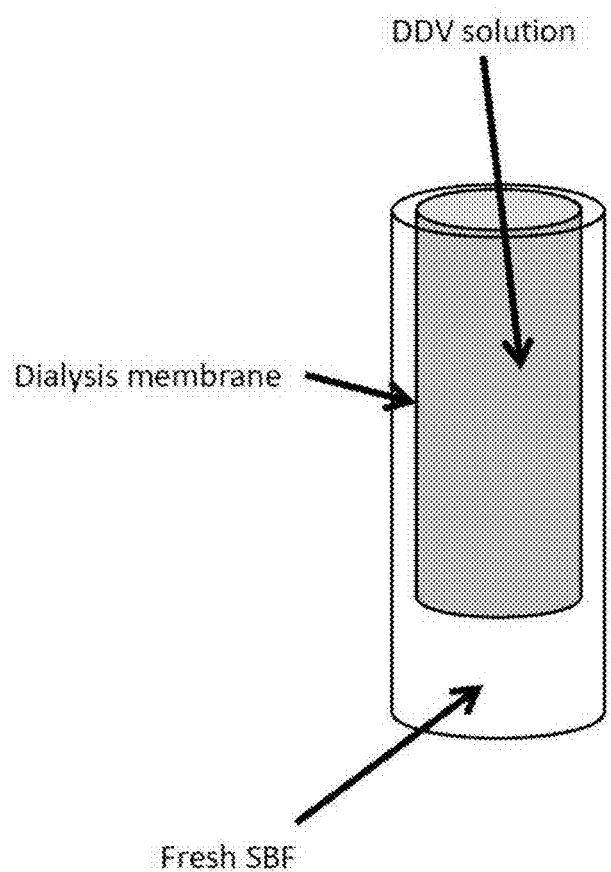

FIG. 34 is a view illustrating a tube having a cylindrical permeable membrane according to one illustrative example.

Figure 35:
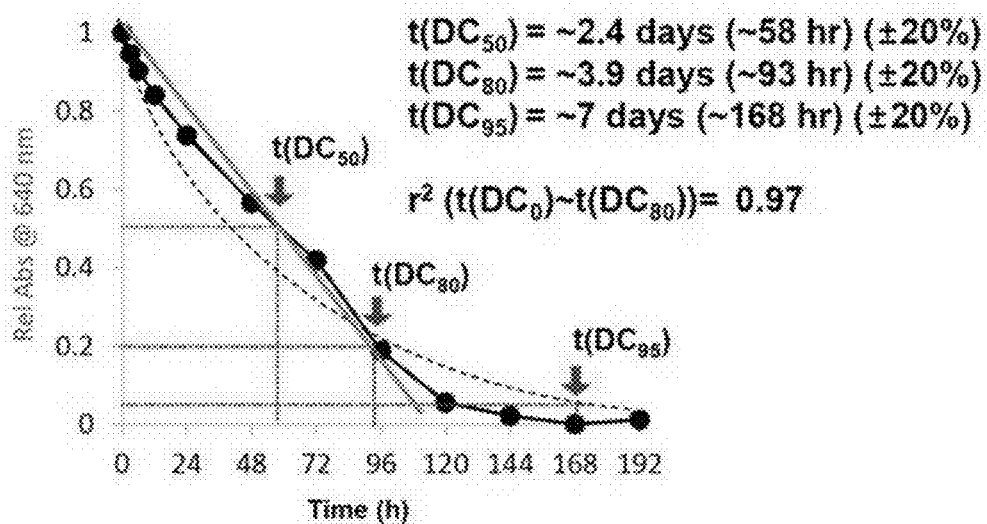

FIG. 35 is a graph illustrating results of decreasing absorbance of the porous silica particles over time according to one embodiment of the present invention.

Figure 36:
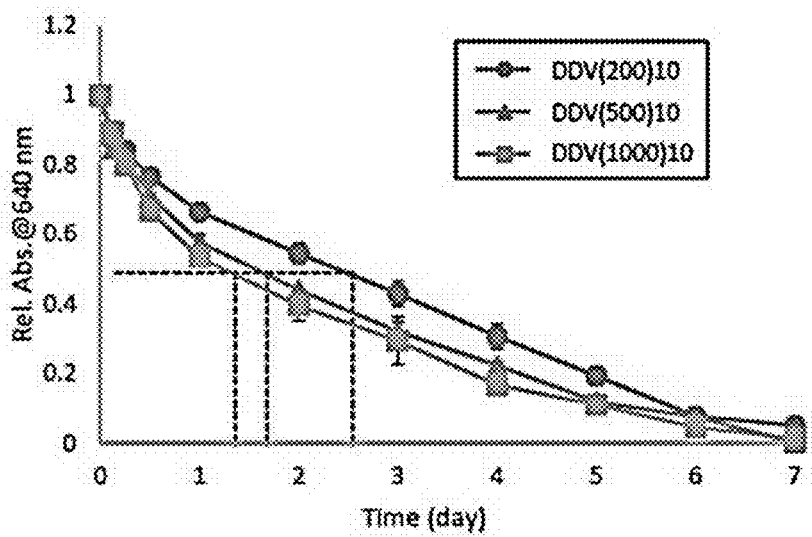

FIG. 36 is diagrams illustrating results of decreasing absorbance of the porous silica particles for each particle size over time according to one embodiment of the present invention.

Figure 37:
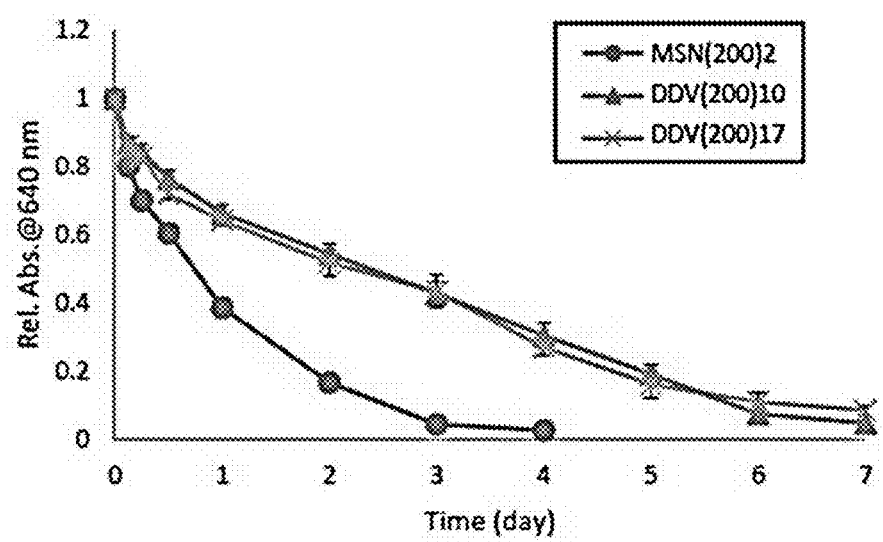

FIG. 37 is diagrams illustrating results of decreasing absorbance of the porous silica particles for each pore diameter over time according to one embodiment of the present invention.

Figure 38:
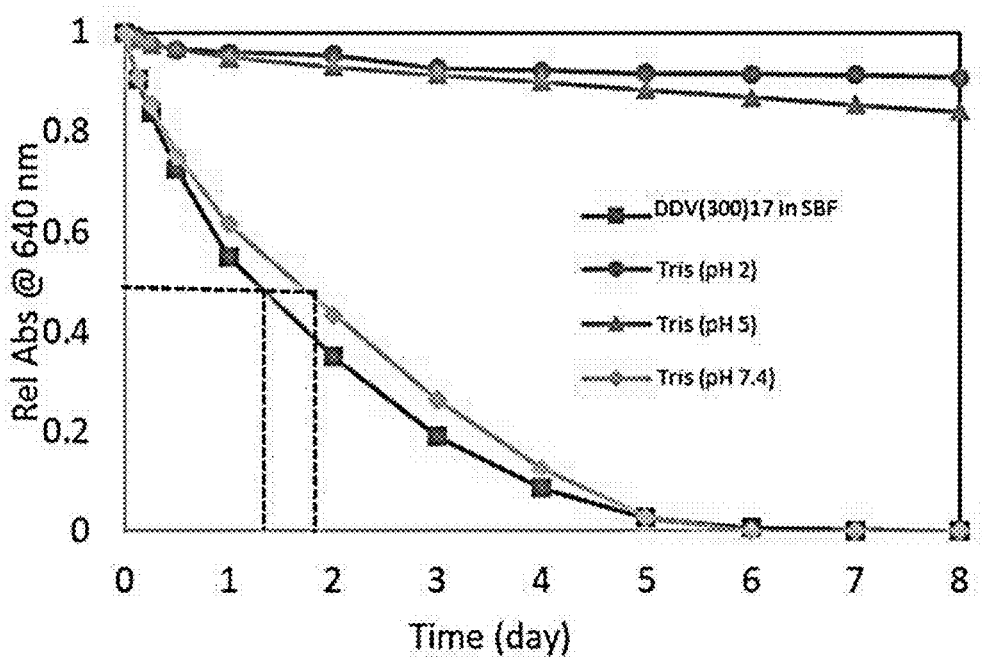

FIG. 38 is a graph illustrating results of decreasing absorbance of the porous silica particles for each pH of the environment over time according to one embodiment of the present invention.

Figure 39:
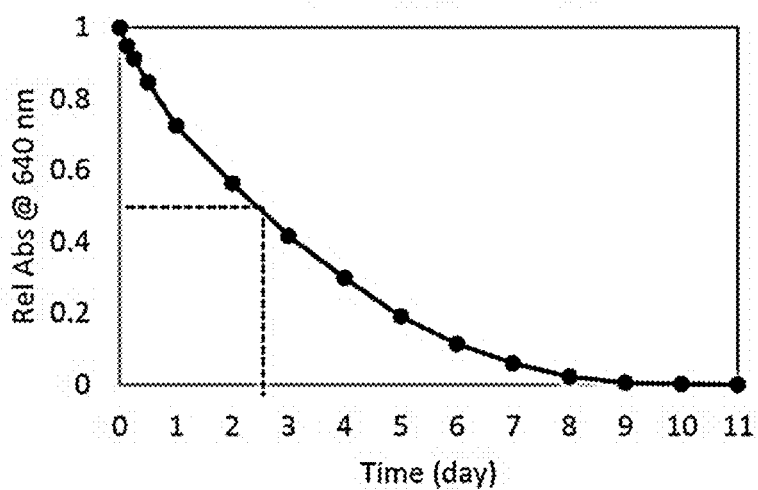

FIG. 39 is a graph illustrating results of decreasing absorbance of the porous silica particles over time according to one embodiment of the present invention.

Figure 40:
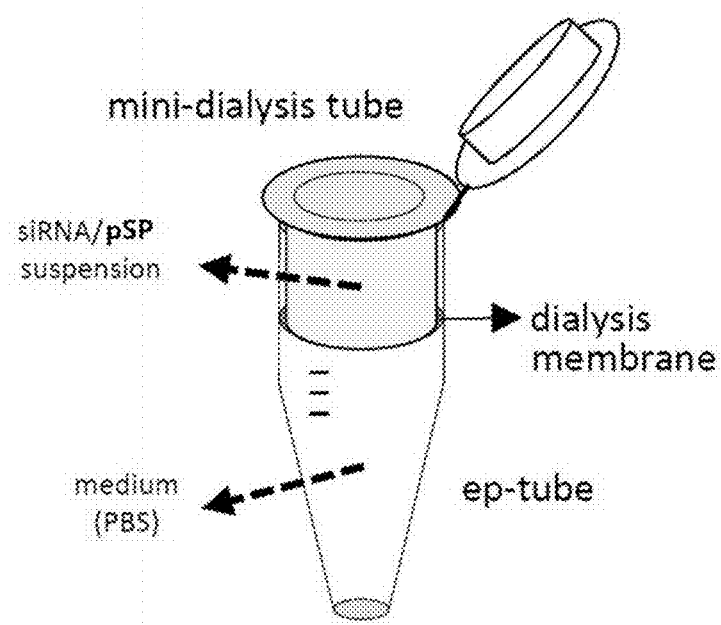

FIG. 40 is a view illustrating a tube to identify siRNA or dsRNA release according to one illustrative example.

Figure 41:
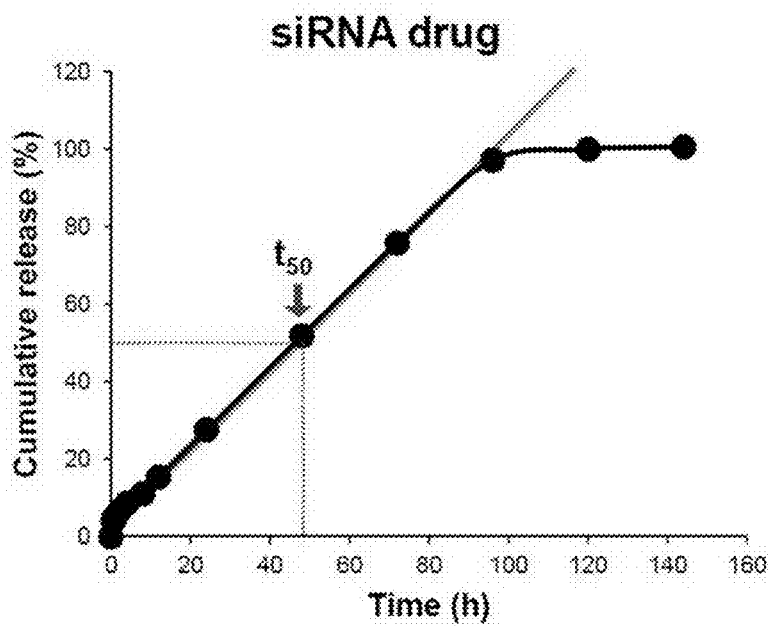

FIG. 41 is a graph illustrating a degree of release of siRNA supported in the porous silica particles over time according to one embodiment of the present invention.

DETAILED DESCRIPTION

In the detailed description of the present invention, specific meanings of terms are defined, however, substantially accepted as common meanings understood by those skilled in the art and not intended to be limited to the specific meanings defined below.

"siRNA" refers to a nucleic acid molecule capable of mediating RNA interference or gene silencing. siRNA can suppress expression of a target gene and thus is provided as an efficient gene knockdown method or gene therapy method. The siRNA molecule may have a structure in which a sense strand (a sequence corresponding to mRNA sequence of a target gene) and an antisense strand (a sequence complementary to the mRNA sequence of the target gene) are positioned opposite to each other to form a double-chain. Further, the siRNA molecule may have a single chain structure with self-complementary sense and antisense strands. siRNA is not limited to the complete pairing of double-stranded RNA portions wherein RNAs are paired, but may include impaired portions due to mismatch (the corresponding bases are not complementary), bulge (without bases corresponding to one chain), etc. The siRNA terminal structure may be either blunt or cohesive, as long as the expression of the target gene may be suppressed by RNAi (RNA interference) effects. The cohesive terminal structure may be both a 3'-terminal protrusion structure and a 5'-terminal protrusion structure. Further, the siRNA molecule may include a short nucleotide sequence (e.g., about 5-15 nt) inserted between self-complementary sense and antisense strands. In this case, the siRNA molecule formed by expression of the nucleotide sequence may form a hairpin structure by intramolecular hybridization and form a stem-and-loop structure as a whole. The stem-and-loop structure may be processed in vitro or in vivo to produce active siRNA molecules capable of mediating RNAi.

"dsRNA" is to a precursor molecule of siRNA, meets RISC complex containing DICER enzyme (Ribonuclease III) of a target cell, and is cleaved into siRNA. In this process, RNAi occurs. dsRNA has a sequence longer by several nucleotides than siRNA, and may have a structure in which a sense strand (a sequence corresponding to mRNA sequence of a target gene) and an antisense strand (a sequence complementary to the mRNA sequence of the target gene) are positioned opposite to each other to form a double-chain.

"PNA" is a synthetic polymer that has a structure similar to DNA or RNA, but is designed to have no charge unlike DNA or RNA thus to have a strong binding force, wherein the DNA and RNA have deoxyribose or ribose backbones, respectively, while a backbone of the PNA has a structure of repeated N-(2-aminoethyl)-glycine ((N-(2-aminoethyl)-glycine) units linked by peptide bonds. The above structure is a structure of purine and pyrimidine bases linked to the backbone by methylene (—$CH_2$—) and carbonyl groups (—C=O—), and has N-terminal and C-terminal at both ends thereof similar to peptide.

The term "nucleic acid" means inclusion of any PNA, DNA or RNA, for example, chromosomes, mitochondria, viruses and/or bacterial nucleic acids present in a tissue sample. One or both strands of a double-stranded nucleic acid molecule are included, and any fragment or portion of an intact nucleic acid molecule is also included.

The term "gene" refers to any nucleic acid sequence or a portion thereof that play a functional role in protein coding or transcription or in regulation of other gene expression. The gene may consist of any nucleic acid encoding a functional protein or only a portion of the nucleic acid encoding or expressing protein. A nucleic acid sequence may include gene abnormalities in exons, introns, initial or terminal regions, promoter sequences, other regulatory sequences, or unique sequences adjacent to genes.

The term "gene expression" generally refers to a cellular process in which biologically active polypeptide is produced from a DNA sequence and exhibits biological activity in a cell. In this meaning, the gene expression includes not only transcriptional and translational processes, but also posttranscriptional and post-translational processes that may possibly affect the biological activity of a gene or gene product. The processes include RNA synthesis, processing and transport, as well as polypeptide synthesis, transport and post-translational modifications of polypeptide, but it is not limited thereto. In the case of genes that do not encode protein products, such as siRNA genes, the term "gene expression" refers to a process by which precursor siRNAs are produced from a gene. Typically, this process is referred to as transcription although a transcription product of siRNA gene does not produce a protein by translation, which is different from transcription induced by RNA polymerase II with regard to a protein coding gene. Nevertheless, generation of mature siRNA from siRNA gene is encompassed by the term "gene expression" as that term is used herein.

The term "target gene" refers to a gene that is targeted to be regulated using the methods and compositions as the subject matters disclosed herein. Therefore, the target gene includes a nucleic acid sequence whose expression level is down regulated by siRNA to the mRNA or polypeptide level. Similarly, the term "target RNA" or "target mRNA" refers to the transcript of a target gene to which siRNA is bound to induce regulation of expression of the target gene.

The term "transcription" refers to a cellular process that involves interaction of an expression inducible gene as RNA of structural information present in a coding sequence of the gene with RNA polymerase.

The expression "down-regulation" refers to considerable reduction in expression of specific genes into mRNAs or proteins by intracellular gene transcription or gene translation in activated cells, as compared to normal tissue cells.

The term "treatment" means an approach to obtain beneficial or desirable clinical results. For the purposes of the present invention, beneficial or desirable clinical outcomes include, without limitation thereof, alleviation of symptoms, reduction of disease range, stabilization of disease state (i.e., not worsening), delayed or sustained disease progression, improvement or temporary mitigation and alleviation of disease state (partially or wholly), whether it is detectable or not detected. The term "treatment" may also mean increasing survival compared to expected survival when untreated. The treatment refers to both therapeutic treatment and prophylactic or preventive measures. Such treatment includes not only treatment of disorders to be prevented but also treatment required for already occurring disorders.

The term "prevention" means any action that inhibits or delays development of a relevant disease. It will be apparent to those skilled in the art that the composition of the present invention can prevent initial symptoms, or related diseases if administered before occurrence of the diseases.

Hereinafter, the present invention will be described in detail.

The present invention provides a composition for inhibiting CTGF gene expression, which includes a nucleic acid molecule consisting of a sequence complementary to a sequence of SEQ ID NO: 1 with complementarity of 10 nucleotides or more.

Complementarity with the sequence of SEQ ID NO: 1 may be 10 nucleotides (nt) or more, 11 nucleotides or more, 12 nucleotides or more, 13 nucleotides or more, 14 nucleotides or more, 15 nucleotides or more, 16 nucleotides or more, 17 nucleotides or more, or the entire of 18 nucleotides.

The nucleic acid molecule may be a single strand of siRNA, dsRNA, PNA or miRNA and, in this case, the siRNA, dsRNA, PNA or miRNA may inhibit expression of CTGF gene by RNAi (RNA interference). More specifically, among the mRNA sequences as a transcript of CTGF gene, the nucleic acid molecule may be complementarily bound to at least a portion of the region consisting of the sequence of SEQ ID NO: 1, thereby inhibiting CTGF gene expression.

When the nucleic acid molecule forms a single strand of siRNA, dsRNA, PNA or miRNA, it is obvious that the sequence conforms to conditions to be considered in the design of siRNA, dsRNA, PNA or miRNA in the level of those skilled in the art. In this case, it may be designed to avoid a palindrome sequence, which in turn prevents reduction of RNAi efficiency caused by a hairpin shape or a cross shape. Specifically, for example, siRNA or dsRNA of the present invention may be designed not to include a sequence of SEQ ID NO: 100 (5'-AACUUGAACU-3'). In the case of PNA of the present invention, it may be designed not to have C and G at both terminals, respectively, thereby avoiding a complementary relationship with each other. Further, it may be designed to maintain the entire sequence length of nucleic acid molecule more than a desired length, thereby having stable RNAi efficiency.

A total sequence length of the nucleic acid molecule may be 10 to 30, 11 to 29, 12 to 28, 13 to 27, 14 to 26, 15 to 25, 16 to 24, 16 to 23, 16 to 22, 16 to 21, or 16 to 20 nucleotides in length, but it is not necessarily limited thereto. In order to maintain a desirable length or more and thus achieve stable RNAi efficiency, the total sequence length preferably ranges from 16 to 20 nucleotides.

Specifically, the nucleic acid molecule may be any one of: an antisense RNA (sequence of SEQ ID NO: 2) that complementarily binds to the sense RNA having the sequence of SEQ ID NO: 1 to form a siRNA: a strand that complementarily binds to a strand consisting of a sequence of SEQ ID NO: 3 to form a dsRNA: an antisense RNA (sequence of SEQ ID NO: 53) that complementarily binds to the sense RNA having the sequence of SEQ ID NO: 1 to form a siRNA: a strand that complementarily binds to a strand consisting of a sequence of SEQ ID NO: 54 to form a dsRNA: an antisense RNA (sequence of SEQ ID NO: 56) that complementarily binds to a sense RNA having a sequence of SEQ ID NO: 55 to form a siRNA; a strand that complementarily binds to a strand consisting of a sequence of SEQ ID NO: 57 to form a dsRNA; an antisense RNA (sequence of SEQ ID NO: 59) that complementarily binds to a sense RNA having a sequence of SEQ ID NO: 58 to form a siRNA: a strand that complementarily binds to a strand consisting of a sequence of SEQ ID NO: 60 to form a dsRNA; an antisense RNA (sequence of SEQ ID NO: 62) that complementarily binds to a sense RNA having a sequence of SEQ ID NO: 61 to form a siRNA; a strand that complementarily binds to a strand consisting of a sequence of SEQ ID NO: 63 to form a dsRNA: an antisense RNA (sequence of SEQ ID NO: 65) that complementarily binds to a sense RNA having a sequence of SEQ ID NO: 64 to form a siRNA; a strand that complementarily binds to a strand consisting of a sequence of SEQ ID NO: 66 to form a dsRNA: an antisense RNA (sequence of SEQ ID NO: 68) that complementarily binds to a sense RNA having a sequence of SEQ ID NO: 67 to form a siRNA: a strand that complementarily binds to a strand consisting of a sequence of SEQ ID NO: 69 to form a dsRNA; an antisense RNA (sequence of SEQ ID NO: 71) that complementarily binds to a sense RNA having a sequence of SEQ ID NO: 70 to form a siRNA: or a strand that complementarily binds to a strand consisting of a sequence of SEQ ID NO: 72 to form a dsRNA.

Specifically, the nucleic acid molecule may be a PNA having one sequence selected from the group consisting of SEQ ID NO: 87 to SEQ ID NO: 99.

Detailed information of the above-mentioned sequences is specifically indicated in the attached sequence list and Table 1 below.

Nucleic acid molecules of the present invention may be derived from animals including human, for example, monkeys, pigs, horses, cows, sheep, dogs, cats, mice, rabbits, and the like, and preferably derived from human.

The nucleic acid molecule of the present invention has been modified by deletion, substitution or insertion of functional equivalents of the nucleic acid molecule to constitute the same, for example, some nucleotide sequences of the nucleic acid molecule according to the present invention. However, variants with the same functions as the nucleic acid molecule of the present invention may substantially belong to the same concept.

More specifically, when the nucleic acid molecule of the present invention forms a sense RNA or antisense RNA of siRNA, the sense RNA and antisense RNA sequence may further include a sequence of UU or dTdT at 3'-terminal thereof. In this case, the siRNA or dsRNA may have advantages such as improvement of structural stability of siRNA or dsRNA through an increase in resistance to nucleic acid hydrolase, improvement of RNAi efficiency of siRNA or dsRNA through induction of stable RISC and the like.

More specifically, when the nucleic acid molecule of the present invention forms a PNA, at least one terminal of the PNA may further bind to a peptide having at least one sequence selected from the group consisting of SEQ ID NO: 101 to SEQ ID NO: 107, or mPEG$_{5000}$, which preferably increases PNA solubility in a composition or penetration of PNA into a composition, or achieves an advantage of not requiring a separate linker in binding to C-terminal among both terminals (N-terminal or C-terminal).

Nucleic acid molecules of the present invention may be isolated or prepared using standard molecular biology techniques such as chemical synthesis or recombinant methods, or may be commercially available. Further, the composition of the present invention may include not only the nucleic acid molecule itself of the present invention but also other substances capable of increasing an expression rate of the nucleic acid molecule of the present invention in cells, for example, compounds, natural products, novel proteins and the like.

Meanwhile, the nucleic acid molecule of the present invention may be provided with being included in a vector for intracellular expression.

The nucleic acid molecules of the present invention may be introduced into cells using diverse transformation techniques, such as complexes of DNA and DEAE-dextran, complexes of DNA and nuclear proteins, complexes of DNA and lipids. For this purpose, the nucleic acid molecules of the present invention may be included within a carrier that allows for efficient introduction into a cell. The carrier is preferably a vector, and both viral and non-viral vectors may be used. Viral vectors may include, for example, lentivirus, retrovirus, adenovirus, herpesvirus, abipoxvirus vectors, and the like, and preferably a lentiviral vector, but it is not limited thereto. Lentiviruses are a type of retrovirus with features that can infect undivided cells as well as divided cells due to nucleophilicity of a pre-integrated complex (virus "shell") enabling active introduction into nucleopore or a complete nuclear membrane.

The vector containing the nucleic acid molecule of the present invention preferably further includes a selectable marker. The "selectable marker" is intended to facilitate selection of cells into which the nucleic acid molecule of the present invention is introduced. The selectable markers possibly used in the vector are not particularly limited as long as they are genes capable of easily detecting or determining whether to introduce the vector or not. However, representative selectable markers may include markers to confer selectable phenotypes, such as drug resistance, nutritional requirements, resistance to cytotoxic agents, or expression of surface proteins, for example, GFP (green fluorescent protein), puromycin, neomycin (Neo), hygromycin (Hyg), histidinol dehydrogenase gene (hisD) and guanine phosphoribosyltransferase (Gpt), and the like, and GFP (green fluorescent protein) and puromycin markers are preferably used.

The present invention provides a pharmaceutical composition for prevention or treatment of fibroproliferative diseases, which includes the composition described above.

The pharmaceutical composition of the present invention has prophylactic or therapeutic effects of fibroproliferative disease, which may be effects achieved by inhibiting CTGF gene expression of the nucleic acid molecule according to the present invention.

Examples of fibroproliferative diseases, which are diseases to be prevented or treated by the pharmaceutical composition of the present invention may include at least one selected from the group consisting of hypertrophic scar, keloid, fibrosis, pulmonary fibrosis, idiopathic pulmonary fibrosis, liver fibrosis, kidney fibrosis, cystic fibrosis, myelofibrosis, post-peritoneal fibrosis, scleroderma, diabetic retinopathy, Duken's muscular dystrophy, radiation-induced fibrosis, myocardial fibrosis, diabetic kidney disease, chronic renal failure, chronic viral hepatitis, biliary fibrosis, fatty hepatitis, alcoholic steatohepatitis, nonalcoholic steatohepatitis, proliferative vitreoretinopathy, musculoskeletal tumor, osteosarcoma, rhabdomyosarcoma, glioblastoma, lung cancer, ovarian cancer, esophageal cancer, colon cancer, pancreatic cancer, renal sclerosis, sarcoidosis, glaucoma, macular degeneration, subretinal fibrosis, choroidal angiogenesis, vitreoretinopathy, proliferative vitreoretinopathy, diabetic retinopathy, keratitis, pterygium, ophthalmology disease, scleroderma, uterine fibroids, systemic sclerosis, glomerulonephritis, human immuno-deficient viral renal disease, acute respiratory distress syndrome, chronic obstructive pulmonary disease, Raynaud's disease, rheumatoid arthritis, polymyositis, vascular stenosis, periodontitis and periodontal gingiva, but it is not necessarily limited thereto. Specifically, the disease is not particularly limited as long as it corresponds to any of diseases caused by overexpression of CTGF, collagen or the like.

The pharmaceutical composition of the present invention may further include a pharmaceutically acceptable carrier, and may be formulated along with such a carrier. As used herein, the term "pharmaceutically acceptable carrier" refers to a carrier or diluent that does not stimulate the organism and does not inhibit biological activities and properties of the administered compound. Pharmaceutical carriers acceptable in the composition formulated as a liquid solution are sterile and biocompatible, and may include saline, sterile water, Ringer's solution, buffered saline, albumin injectable solutions, dextrose solution, maltodextrin solution, glycerol, ethanol, and a mixture of one or more of these components. Further, if necessary, other typical additives such as antioxidants, buffers and bacteriostatic agents may be added. Diluents, dispersants, surfactants, binders and lubricants may also be added to formulate the pharmaceutical composition into injectable formulations, pills, capsules, granules or tablets such as aqueous solutions, suspensions, emulsions and the like.

The pharmaceutical composition of the present invention is applicable in a form of any formulation containing the nucleic acid molecule of the present invention as an active ingredient, and may be prepared in oral or parenteral formulations. The pharmaceutical formulations of the present invention may include forms suitable for oral, rectal, nasal, topical (including the cheek and sublingual), subcutaneous, vaginal or parenteral (intramuscular, subcutaneous) administration. Alternatively, forms suitable for administration by inhalation or insufflations may also be included.

The pharmaceutical composition of the present invention is administered in a pharmaceutically effective amount. Effective dose levels may be determined depending on types of disease of the patient, severity, activity of drug, sensitivity to drug, administration time, administration route and rate of release, duration of treatment, factors including concurrent medications, and other factors well known in the medical field. The pharmaceutical composition of the present invention may be administered as an individual therapeutic agent or in combination with other therapeutic agents, may be administered sequentially or simultaneously with conventional therapeutic agents, and may be administered in single or multiple doses. Taking all of the above factors into consideration, it is important to administer the pharmaceutical composition in an amount that can achieve maximum effects with a minimum amount without side effects, which may be easily determined by those skilled in the art.

The dosage of the pharmaceutical composition according to the present invention may vary widely depending on the weight, age, sex, health conditions or diet of a patient, administration time, administration method, excretion rate and severity of the disease, and the appropriate dosage depends on, for example, an amount of drug accumulated in the patient's body and/or specific efficacy of the nucleic acid molecules of the present invention used. Generally, the amount may be calculated on the basis of EC50, which is generally determined to be effective in in vivo animal models and in vitro, for example, from 0.01 µg to 1 g per kg of body weight. Further, the pharmaceutical composition of the present invention may be administered once or several times per unit time during unit periods of time such as daily, weekly, monthly or yearly, or may be continuously administered using an infusion pump for a long time. The number of repeated administration doses is determined in consideration of a residential time of drug in the body, a drug concentration in the body, etc. Even after treatment according to the course of disease treatment, the composition may be further administered for preventing recurrence, i.e., relapse of the disease.

The pharmaceutical composition of the present invention may further include a compound to maintain/increase one or more of active ingredients exhibiting the same or similar functions in relation to treatment of fibroproliferative diseases or the solubility and/or absorption of at least one active ingredient. Further, the composition may also optionally include chemotherapeutic agents, anti-inflammatory agents, antiviral agents and/or immunomodulators and the like.

Further, the pharmaceutical composition of the present invention may be formulated using any method known in the art to allow rapid, sustained or delayed release of the active ingredient after administration to a mammal. The formulation may be produced in a form of powders, granules, tablets, emulsions, syrups, aerosols, soft or hard gelatin capsules, sterile injectable solutions, sterile powders.

The composition of the present invention may be supported on a carrier having a nucleic acid molecule that complementarily binds to at least a portion of a transcript of CTGF gene. Types of the carrier are not particularly limited as long as it can support the nucleic acid molecule thereon and is known in the art. For example, the carrier may include at least one selected from the group consisting of liposomes, lipofectamine, dendrimers, micelles, porous silica particles, aminoclays and hydrogels, however, preferably porous silica particles having advantages such as high nucleic acid molecule loading rate, sustained release, biodegradability and the like.

The present invention provides a composition for inhibiting CTGF gene expression, including: porous silica particles carrying nucleic acid molecules that complementarily bind to at least a portion of a transcript of CTGF gene. The porous silica particles are particles based on silica ($SiO_2$) material and have a nano-scale particle size.

The porous silica nanoparticles of the present invention are porous particles, each of which has nano-scale pores and can carry a nucleic acid molecule complementarily bound to at least a portion of the transcript of CTGF gene (hereinafter, abbrev. to "CTGF gene transcript complementarily binding nucleic acid molecule") on the surface thereof and/or the inside of the pores.

The porous silica particles of the present invention are biodegradable particles, which carry CTGF gene transcript complementarily binding nucleic acid molecule, and can release the same, that is, CTGF gene transcript complementarily binding nucleic acid molecule while being biodegraded in the body when administered to the body. The porous silica particles of the present invention may be slowly degraded in the body to allow sustained release of the supported CTGF gene transcript complementarily binding nucleic acid molecule. For example, "t", at which a ratio of absorbance of the following Equation 1 becomes 1/2, is 24 or more:

$$A_t/A_0 \qquad \text{[Equation 1]}$$

wherein $A_0$ is absorbance of the porous silica particles measured by putting 5 ml of suspension containing 1 mg/ml of porous silica particles into a cylindrical permeable membrane having pores with a pore diameter of 50 kDa, 15 ml of the same solvent as the suspension comes into contact with an outside of the permeable membrane, and the inside/outside of the permeable membrane are horizontally stirred at 60 rpm and at 37° C., pH of the suspension is 7.4, and $A_t$ indicates absorbance of the porous silica particle measured after lapse of "t" hours since $A_o$ was measured.

The above Equation 1 means what a rate the porous silica particles are degraded in an environment similar to the body.

As shown in FIG. 34, for example, absorbances $A_0$ and $A_t$ in the above Equation 1 may be measured after placing porous silica particles and a suspension in a cylindrical permeable membrane and also placing the same suspension outside the permeable membrane.

The porous silica particles of the present invention are biodegradable, and may be slowly degraded in the suspension. The diameter of 50 kDa corresponds to about 5 nm, which allows biodegradable porous silica particles to pass through a permeable membrane having a diameter of 50 kDa, and a cylindrical permeable membrane is under horizontal agitation at 60 rpm to evenly blend the suspension, such that the degraded porous silica particles can come out of the permeable membrane.

The absorbance in the above Equation 1 may be measured, for example, under an environment in which the suspension outside the permeable membrane is replaced with a new suspension. The suspension may be continuously replaced, or replaced every period wherein the period is periodic or irregular. For example, the suspension may be replaced at 1 hour interval, 2 hours interval, 3 hours interval, 6 hours interval, 12 hours interval, 24 hours interval, 2 days interval, 3 days interval, 4 days interval, 7 days interval, etc., within a range of 1 hour to 1 week, but it is not limited thereto.

The absorbance ratio of 1/2 means that the absorbance is half of the initial absorbance after t hours, that is, that approximately half of the porous silica particles are degraded.

The suspension may be a buffer solution, for example, at least one selected from the group consisting of phosphate buffered saline (PBS) and simulated body fluid (SBF), and more specifically, PBS.

"t" in the above Equation 1 of the present invention, at which the absorbance ratio becomes 1/2, may be 24 or more, for example, t may range from 24 to 120. That is, within the above range, t may range from 24 to 96, 24 to 72, 30 to 70, 40 to 70, 50 to 65, etc., but it is not limited thereto.

With regard to the porous silica particles of the present invention, t at which the absorbance ratio in the above Equation 1 becomes 1/5 may range from 70 to 140. For example, t may range from 80 to 140, 80 to 120, 80 to 110, 70 to 140, 70 to 120, 70 to 110, etc. within the above range, but it is not limited thereto.

With regard to the porous silica particles of the present invention, t at which the absorbance ratio in the above Equation 1 becomes 1/20 may range from 130 to 220. For example, t may range from 130 to 200, 140 to 200, 140 to 180, 150 to 180, etc. within the above range, but it is not limited thereto.

With regard to the porous silica particles of the present invention, t at which the absorbance ratio in the above Equation 1 becomes 0.01 or less may be 250 or more. For example, t may be 300 or more, 350 or more, 400 or more, 500 or more, 1000 or more, etc. and the upper limit may be 2000, but it is not limited thereto.

With regard to the porous silica particles of the present invention, the absorbance ratio and t in the above Equation 1 have high positive correlation. For example, Pearson correlation coefficient may be 0.8 or more, and for example, 0.9 or more and 0.95 or more.

"t" in the above Equation 1 means how fast the porous silica particles are degraded under the environment similar to the body. That is, t may be regulated by adjusting, for example, a surface area, a particle size, a pore diameter, substituents on the surface of the porous silica particles and/or the inside of the pores, compactness of the surface and the like.

For example, the surface area of the particle may be increased to reduce t, or the surface area may be decreased to increase t. The surface area may be regulated by adjusting the particle size and the pore diameter of the particles. Further, if direct exposure of the porous silica particles to the environment (such as solvents) is reduced by placing substituents on the surface of the particles and/or the inside of the pores, t may be increased. Further, when the porous silica particles support or carry CTGF gene transcript complementarily binding nucleic acid molecules, and when increasing affinity between the CTGF gene transcript complementarily binding nucleic acid molecules and the porous silica particles, direct exposure of the porous silica particles to the environment may be reduced, thereby increasing t. In addition, t may be increased by preparing the particles with more compact surface. As described above, various examples of adjusting t in the above Equation 1 have been described, but it is not limited thereto.

The porous silica particles of the present invention may have a spherical shape, but it is not limited thereto.

The porous silica particles of the present invention may have an average diameter of, for example, 150 to 1000 nm. For example, the average diameter may range from 150 to 800 nm, 150 to 500 nm, 150 to 400 nm, 150 to 300 nm, and 150 to 200 nm, etc. within the above range, but it is not limited thereto.

The porous silica particles of the present invention may have an average pore diameter of, for example, 1 to 100 nm. For example, the pore diameter may range from 5 to 100 nm, 7 to 100 nm, 7 to 50 nm, 10 to 50 nm, 10 to 30 nm, 7 to 30 nm, etc., within the above range, but it is not limited thereto. The porous silica particles having a large diameter as described above may carry CTGF gene transcript complementarily binding nucleic acid molecules, and may further carry nucleic acid molecules that complementarily bind to at least a portion of the transcript of large-sized CTGF gene.

The porous silica particles of the present invention may have a BET surface area of, for example, 200 to 700 m$^2$/g. For example, the BET surface area may range from 200 to 700 m 2/g, 200 to 650 m$^2$/g, 250 to 650 m$^2$/g, 300 to 700 m$^2$/g, 300 to 650 m$^2$/g, 300 to 600 m$^2$/g, 300 to 550 m$^2$/g, 300 to 500 m$^2$/g, 300 to 450 m$^2$/g, etc. within the above range, but it is not limited thereto.

Porous silica nanoparticles of the present invention may have a volume per gram, for example, 0.7 to 2.2 ml. For example, the volume may range from 0.7 to 2.0 ml, 0.8 to 2.2 ml, 0.8 to 2.0 ml, 0.9 to 2.0 ml, 1.0 to 2.0 ml, etc. within the above range, but it is not limited thereto. If the volume per gram is too small, a degradation rate may be too high. Further, it is difficult to manufacture excessively large particles or particles having an intact shape.

The porous silica particles of the present invention may have hydrophilic substituents and/or hydrophobic substituents on an outer surface thereof and/or an inside of the pores. For example, only hydrophilic substituents or only hydrophobic substituents may exist on both the surface of the particles and inside of the pores, hydrophilic substituents or hydrophobic substituents may be present on either the surface of the particles or the inside of the pores, or hydrophilic substituents may be present on the surface of the particles while hydrophobic substituents may exist inside of the pores, or vice versa.

Release of the nucleic acid molecules complementarily bound to at least a portion of the transcript of CTGF gene (that is, CTGF gene transcript complementarily binding nucleic acid molecules) supported on the porous silica particles according to the present invention is mainly performed by degradation of nanoparticles. Specifically, interaction of the porous silica particles with the release environment of the CTGF gene transcript complementarily binding nucleic acid molecules is adjusted to regulate a degradation rate of the nanoparticles, so that a release rate of the CTGF gene transcript complementarily binding nucleic acid molecules may be regulated. Further, the CTGF gene transcript complementarily binding nucleic acid molecules may be diffused and released from the nanoparticles, wherein adjusting substituents may regulate a binding force of the CTGF gene transcript complementarily binding nucleic acid molecules to the nanoparticles, thereby controlling release of the CTGF gene transcript complementarily binding nucleic acid molecules.

Further, in order to increase a binding force of the silica particle to a nucleic acid molecule or material that complementarily binds to at least a portion of the transcript of poorly soluble (hydrophobic) CTGF gene, hydrophobic substituents may be present inside of the pores of the particle. Further, in aspects of easy use and formulation, the surface of the particles may also be treated to have hydrophilic substituents.

The hydrophilic substituents may include, for example, hydroxyl group, carboxy group, amino group, carbonyl group, sulfhydryl group, phosphate group, thiol group, ammonium group, ester group, imide group, thioimide group, keto group, ether group, indene group, sulfonyl group, polyethyleneglycol group and the like. Further, the hydrophobic substituent may include, for example, substituted or unsubstituted C1 to C30 alkyl group, substituted or unsubstituted C3 to C30 cycloalkyl group, substituted or unsubstituted C6 to C30 aryl group, substituted or unsubstituted C2 to C30 heteroaryl group, halogen group, C1 to C30 ester group, halogen-containing group and the like.

Further, the porous silica particles of the present invention may be positively charged, negatively charged and/or uncharged at an outer surface thereof and/or an inside of the pores. For example, both the surface of the particles and the inside of the pores may be positively charged or negatively charged, only the surface of the particles or the inside of the pores may be positively charged or negatively charged. Alternatively, the surface of the particles may be positively charged while the insider of the pore may be negatively charged or vice versa, which is similar to the case of being uncharged.

The charging may be performed, for example, by the presence of a nonionic substituent, a cationic substituent or an anionic substituent.

The cationic substituent may include, for example, amino group or any other nitrogen-containing group as a basic group, specifically, at least one functional group selected from the group consisting of amino group, aminoalkyl group, alkylamino group, a heterocyclic aromatic compound group containing a nitrogen atom, cyan group and guanidine group, but it is not limited thereto.

The anionic substituent may include, for example, carboxy group (—COOH), sulfonic acid group (—SO$_3$H), thiol group (—SH), etc. as an acidic group, but it is not limited thereto.

Likewise, when interaction of the porous silica particles with release environment of the CTGF gene transcript complementarily binding nucleic acid molecules is regulated by adjusting the substituents through charging, a degradation rate of nanoparticles may be regulated to control a release rate of the CTGF gene transcript complementarily binding nucleic acid molecules. Further, the CTGF gene transcript complementarily binding nucleic acid molecules may be diffused and released from the nanoparticles. In this regard, adjusting the substituents may regulate a binding force of the CTGF gene transcript complementarily binding nucleic acid molecules to the nanoparticles, thereby controlling release of the CTGF gene transcript complementarily binding nucleic acid molecules.

Further, the porous silica particles of the present invention may include substituents for the purposes of: supporting the CTGF gene transcript complementarily binding nucleic acid molecules on the surface of the particles and/or the inside of the pores: delivery of the CTGF gene transcript complementarily binding nucleic acid molecules into a target cell: supporting other substances for other purposes: or binding of additional substituents. Further, the porous silica particles may also include antibodies, ligands, cell permeable peptides, or aptamers bound thereto.

The substituents on the surface of the particles and/or the inside of the pores, charge, binders, etc. described above may be added by, for example, surface modification.

Surface modification may be performed, for example, by reacting a compound having a substituent to be introduced with the particles, wherein the compound may be, for example, alkoxysilane having C1 to C10 alkoxy group, but it is not limited thereto. The alkoxysilane has one or more alkoxy groups, for example, 1 to 3 alkoxy groups. Further, there may be a substituent to be introduced into a site where the alkoxy group is not bound, or a substituent substituted with the same.

The porous silica particles of the present invention may be manufactured, for example, through small pore particle preparation and pore expansion processes and, if necessary, may be manufactured further through calcination, or surface modification process and the like. If both the calcination and the surface modification processes have been implemented, the particles may be surface-modified after calcination.

The small pore particles may be, for example, particles having an average pore diameter of 1 to 5 nm.

The small pore particles may be harvested by adding a surfactant and a silica precursor in a solvent, followed by agitation and homogenization.

The solvent may be water and/or an organic solvent, and the organic solvent may include, for example: ethers such as 1,4-dioxane (particularly cyclic ethers); halogenated hydrocarbons such as chloroform, methylene chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methylisobutylketone, Y-butyrolactone, 1,3-dimethyl-imidazolidinone, methylethylketone, cyclohexanone, cyclopentanone, 4-hydroxy-4-methyl-2-pentanone, etc.; aromatic carbon-based materials such as benzene, toluene, xylene, tetramethylbenzene, etc.; alkyl amides such as N,N-dimethylformamide, N,N-dibutylformamide, N,N-dimethylacetamide, N-methylpyrrolidone, etc.; alcohols such as methanol, ethanol, propanol, butanol, etc.; glycol ethers (cellosolve) such as ethyleneglycol monoethyl ether, ethyleneglycol monomethyl ether, ethyleneglycol monobutyl ether, diethyleneglycol monoethyl ether, diethyleneglycol monomethyl ether, diethyleneglycol monobutyl ether, propyleneglycol monomethyl ether, propyleneglycol monoethyl ether, dipropyleneglycol diethyl ether, triethyleneglycol monoethyl ether, etc.; others such as dimethylacetamide (DMAc), N,N-diethylacetamide, dimethylformamide (DMF), diethylformamide (DEF), N,N-dimethylacetamide (DMAc), N-methylpyrrolidone (NMP), N-ethylpyrrolidone (NEP), 1,3-dimethyl-2-imidazolidinone, N,N-dimethylmethoxyacetamide, dimethyl sulfoxide, pyridine, dimethyl sulfone, hexamethylphosphoamide, tetramethylurea, N-methylcarrolactam, tetrahydrofuran, m-dioxane, P-dioxane, 1,2-dimethoxyethane and the like. Specifically, alcohol, more specifically methanol may be used, but it is not limited thereto. When using a mixed solvent of water and the organic solvent, a relative ratio of water and organic solvent may be, for example, in a volume ratio of 1:0.7 to 1.5, for example, 1:0.8 to 1.3, but it is not limited thereto.

The surfactant may include, for example, cetyltrimethylammonium bromide (CTAB), hexadecyltrimethylammonium bromide (TMABr), hexadecyltrimethylpyridinium chloride (TMPrCl), tetramethylammonium chloride (TMACl), etc., and specifically, CTAB may be used.

The surfactant may be added, for example, in an amount of 1 to 10 g, for example, 1 to 8 g, 2 to 8 g or 3 to 8 g per liter of solvent, but it is not limited thereto.

The silica precursor may be added after stirring with addition of a surfactant to the solvent. The silica precursor may be, for example, tetramethyl orthosilicate (TMOS), but it is not limited thereto.

The stirring may be conducted, for example, for 10 to 30 minutes, but it is not limited thereto.

The silica precursor may be added in an amount of 0.5 to 5 ml per liter of solvent, for example, 0.5 ml to 4 ml, 0.5 to 3 ml, 0.5 to 2 ml, 1 to 2 ml, etc. within the above range, but it is not limited thereto.

If necessary, sodium hydroxide may further be used as a catalyst, specifically, and may be added under stirring after addition of the surfactant and before addition of the silica precursor to the solvent.

The sodium hydroxide may be added in an amount of 0.5 to 8 ml per liter of solvent, for example, 0.5 to 5 ml, 0.5 to 4 ml, 1 to 4 ml, 1 to 3 ml, 2 to 3 ml, etc. within the above range with respect to 1 M aqueous sodium hydroxide solution, but it is not thereto.

After addition of the silica precursor, the solution may be reacted with stirring. The stirring may be conducted for 2 to 15 hours, for example, 3 to 15 hours, 4 to 15 hours, 4 to 13 hours, 5 to 12 hours, 6 to 12 hours, 6 to 10 hours, etc. within the above range, but it is not limited thereto. If the stirring time (reaction time) is too short, nucleation may be insufficient. After agitation, the solution may be aged. Aging may be performed for 8 to 24 hours, for example, for 8 to 20 hours, 8 to 18 hours, 8 to 16 hours, 8 to 14 hours, 10 to 16 hours, 10 to 14 hours, etc. within the above range, but it is not limited thereto.

Thereafter, the reaction product may be washed and dried to harvest porous silica particles and, if necessary, separation of unreacted material may proceed before washing.

Separation of the unreacted material may be implemented by separating the supernatant, for example, through centrifugation. For example, centrifugation may be conducted at 6,000 to 10,000 rpm, and the centrifugation time may range from 3 to 60 minutes, for example, 3 to 30 minutes, 3 to 30 minutes, 5 to 30 minutes, etc. within the above range, but it is not limited thereto.

The washing may be conducted with water and/or an organic solvent. Specifically, since different substances are dissolved in different solvents, water and the organic solvent may be used alternately once or several times, or the washing may be conducted with water or the organic solvent alone once or several times. The several times described above may be 2 times or more and 10 times or less, for example, 3 times or more and 10 times or less, 4 times or more and 8 times or less, 4 times or more and 6 times or less.

The organic solvent may include, for example: ethers such as 1,4-dioxane (particularly cyclic ethers): halogenated hydrocarbons such as chloroform, methylene chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methylisobutylketone, γ-butyrolactone, 1,3-dimethyl-imidazolidinone, methylethylketone, cyclohexanone, cyclopentanone, 4-hydroxy-4-methyl-2-pentanone, aromatic carbon-based materials such as benzene, toluene, xylene, tetramethylbenzene, etc.; alkyl amides such as N,N-dimethylformamide, N,N-dibutylformamide, N,N-dimethylacetamide, N-methylpyrrolidone, etc.; alcohols such as methanol, ethanol, propanol, butanol, etc.; glycol ethers (cellosolve) such as ethyleneglycol monoethyl ether, ethyleneglycol monomethyl ether, ethyleneglycol monobutyl ether, diethyleneglycol monoethyl ether, diethyleneglycol monomethyl ether, diethyleneglycol monobutyl ether, propyleneglycol monomethyl ether, propyleneglycol monoethyl ether, dipropyleneglycol diethyl ether, triethyleneglycol monoethyl ether, etc.; others such as dimethylacetamide (DMAc), N,N-diethylacetamide, dimethylformamide (DMF), diethylformamide (DEF), N, N-dimethylacetamide (DMAc), N-methylpyrrolidone (NMP), N-ethylpyrrolidone (NEP), 1,3-dimethyl-2-imidazolidinone, N,N-dimethylmethoxyacetamide, dimethyl sulfoxide, pyridine, dimethyl sulfone, hexamethylphosphoamide, tetramethylurea, N-methylcarrolactam, tetrahydrofuran, m-dioxane, P-dioxane, 1,2-dimethoxyethane and the like. Specifically, alcohol, more specifically methanol may be used, but it is not limited thereto. The washing may be conducted under centrifugation, for example, at 6,000 to 10,000 rpm, and the centrifugation time may range from 3 to 60 minutes, for example, 3 to 30 minutes, 5 to 30 minutes, etc. within the above range, but it is not limited thereto.

Alternatively, the washing may be conducted by filtering out particles through a filter without centrifugation. The filter may have pores in a size of less than or equal to the diameter of the porous silica particles. When filtering the reaction solution with such a filter as described above, only particles remain on the filter, which may be washed by pouring water and/or an organic solvent on the filter.

In the washing, water and the organic solvent may be used alternately once or several times, or the washing may be conducted with water or the organic solvent alone once or several times. The several times described above may be 2 times or more and 10 times or less, for example, 3 times or more and 10 times or less, 4 times or more and 8 times or less, 4 times or more and 6 times or less.

The drying may be conducted, for example, at 20 to 100° C., but it is not limited thereto, and may also be conducted in a vacuum state.

Thereafter, the pore of the harvested porous silica particles may be expanded, and such pore expansion may be conducted using a pore swelling agent.

The pore swelling agent may include, for example, trimethylbenzene, triethylbenzene, tripropylbenzene, tributylbenzene, tripentylbenzene, trihexylbenzene, toluene, benzene, etc., and specifically, trimethylbenzene may be used, but it is not limited thereto.

Further, the pore swelling agent used herein may be, for example, N, N-dimethylhexadecylamine (DMHA), but it is not limited thereto.

The pore expansion may be performed, for example, by mixing the porous silica particles in the solvent with a pore swelling agent and heating the mixture to induce reaction.

The solvent may be water and/or an organic solvent, and the organic solvent may include, for example: ethers such as 1,4-dioxane (particularly cyclic ethers): halogenated hydrocarbons such as chloroform, methylene chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methylisobutylketone, cyclohexanone, etc.; aromatic carbon-based materials such as benzene, toluene, xylene, etc.; alkyl amides such as N,N-dimethylformamide, N,N-dibutylformamide, N,N-dimethylacetamide, N-methylpyrrolidone, etc.; alcohols such as methanol, ethanol, propanol, butanol and the like. Specifically, alcohol, more specifically methanol may be used, but it is not limited thereto.

The porous silica particles may be added in a ratio of 10 to 200 g per liter of solvent, for example, 10 to 150 g, 10 to 100 g, 30 to 100 g, 40 to 100 g, 50 to 100 g, 50 to 80 g, 60 to 80 g, etc., within the above range, but it is not limited thereto.

The porous silica particles may be evenly dispersed in a solvent. For example, the porous silica particles may be added to the solvent and ultrasonically dispersed. In the case of using a mixed solvent, the porous silica particles may be dispersed in a first solvent, followed by adding a second solvent thereto.

The pore swelling agent may be added in a ratio of 10 to 200 parts by volume ("vol. parts") to 100 vol. parts of solvent, for example, 10 to 150 vol. parts, 10 to 100 vol. parts, 10 to 80 vol. parts, 30 to 80 vol. parts, 30 to 70 vol. parts, etc. within the above range, but it is not limited thereto.

The reaction may be carried out at 120 to 190° C., for example, 120 to 190° C., 120 to 180° C., 120 to 170° C., 130 to 170° C., 130 to 160° C., 130 to 150° C., 130 to 140° C., etc. within the above range, but it is not limited thereto.

The reaction may be carried out for 6 to 96 hours, for example, 30 to 96 hours, 30 to 96 hours, 30 to 80 hours, 30 to 72 hours, 24 to 80 hours, 24 to 72 hours, 36 to 96 hours, 36 to 80 hours, 36 to 72 hours, 36 to 66 hours, 36 to 60 hours, 48 to 96 hours, 48 to 88 hours, 48 to 80 hours, 48 to 72 hours, 6 to 96 hours, 7 to 96 hours, 8 to 80 hours, 9 to 72 hours, 9 to 80 hours, 6 to 72 hours, 9 to 96 hours, 10 to 80 hours, 10 to 72 hours, 12 to 66 hours, 13 to 60 hours, 14 to 96 hours, 15 to 88 hours, 16 to 80 hours, 17 to 72 hours, etc. within the above range, but it is not limited thereto.

The time and temperature may be desirably adjusted within the ranges exemplified above so that the reaction may be carried out sufficiently but not excessively. For example, when the reaction temperature is reduced, the reaction time may be increased, and when the reaction temperature is increased, the reaction time may be shortened. If the reaction is not sufficiently performed, pore expansion may be insufficient. On the other hand, if the reaction proceeds excessively, the particles may collapse due to overexpansion of the pores.

The reaction may be carried out, for example, by gradually raising the temperature. Specifically, the reaction may be carried out by gradually raising the temperature at a rate of 0.5 to 15° C./min from the room temperature to the above-defined temperature. For example, the temperature may be raised at a rate of 1 to 15° C./min, 3 to 15° C./min, 3 to 12° C./min, 3 to 10° C./min, etc., but it is not limited thereto.

The reaction may be carried out under stirring. For example, the stirring may be implemented at a speed of 100 rpm or more, and specifically, at a speed of 100 to 1000 rpm, but it is not limited thereto.

After the reaction, the reaction solution may be cooled slowly, for example, by gradually decreasing the temperature. Specifically, the reaction may be carried out by gradually decreasing the temperature at a rate of 0.5 to 20° C./min from the above-defined temperature to room temperature. For example, the temperature may be decreased at a rate of 1 to 20° C./min, 3 to 20° C./min, 3 to 12° C./min, 3 to 10° C./min, etc. within the above range, but it is not limited thereto.

After cooling, the reaction product may be washed and dried to harvest porous silica particles having expanded pores. If necessary, unreacted material may be first separated before washing.

Separation of the unreacted material may be implemented by separating the supernatant, for example, through centrifugation. Herein, centrifugation may be conducted, for example, at 6,000 to 10,000 rpm, and the centrifugation time may range from 3 minutes to 60 minutes. For example, the centrifugation may be conducted for 3 to 30 minutes, 5 to 30 minutes, etc. within the above range, but it is not limited thereto.

The washing may be conducted with water and/or an organic solvent. Specifically, since different substances are dissolved in different solvents, water and the organic solvent may be used alternately once or several times, or the washing may be conducted with water or the organic solvent alone once or several times. The several times described above may be 2 times or more and 10 times or less, for example, 3 times, 4 times, 5 times, 6 times, 7 times, 8 times, etc.

The organic solvent may include, for example: ethers such as 1,4-dioxane (particularly cyclic ethers); halogenated hydrocarbons such as chloroform, methylene chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methylisobutylketone, cyclohexanone, etc.; aromatic carbon-based materials such as benzene, toluene, xylene, etc.; alkyl amides such as N,N-dimethylformamide, N,N-dibutylformamide, N,N-dimethylacetamide, N-methylpyrrolidone, etc.; alcohols such as methanol, ethanol, propanol, butanol and the like. Specifically, alcohol, more specifically methanol may be used, but it is not limited thereto.

The washing may be conducted under centrifugation, for example, at 6,000 to 10,000 rpm, and the centrifugation time may range from 3 to 60 minutes, for example, 3 to 30 minutes, 5 to 30 minutes, etc. within the above range, but it is not limited thereto.

Alternatively, the washing may be conducted by filtering out particles through a filter without centrifugation. The filter may have pores in a size of less than or equal to the diameter of the porous silica particles. When filtering the reaction solution with such a filter as described above, only particles remain on the filter, which may be washed by pouring water and/or an organic solvent on the filter.

In the washing, water and the organic solvent may be used alternately once or several times, or the washing may be conducted with water or the organic solvent alone once or several times. The several times described above may be 2 times or more and 10 times or less, for example, 3 times or more and 10 times or less, 4 times or more and 8 times or less, 4 times or more and 6 times or less.

The drying may be conducted, for example, at 20 to 100° C., but it is not limited thereto, and may also be conducted in a vacuum state.

Thereafter, the harvested particles may be subjected to calcination, which is a process of heating the particles to remove silanol groups present on the surface of the particles and inside of the pores so as to reduce reactivity of the particles, provide a more compact structure, and remove organic matter filling the pores. For example, the particles may be heated to a temperature of 400° C. or higher. The upper limit of the temperature is not particularly limited but may be 1000° C., 900° C., 800° C., 700° C., etc. The heating may be conducted, for example, for 3 hours or more. The upper limit of the heating time is not particularly limited but may be 24 hours, 12 hours, 10 hours, 8 hours, 6 hours, etc. More particularly, the heating may be conducted at 400 to 700° C. for 3 to 8 hours or at 500 to 600° C. for 4 to 5 hours, but it is not limited thereto.

Removing the organic matter filling the pores can prevent some problems of cytotoxicity or foaming caused by the remaining organic matter.

Then, the harvested porous silica particles may be subjected to surface modification, and the surface modification may be performed on the surface of the particles and/or the inside of the pores. Both the particle surface and the inside of the pores may be surface-modified in the same manner, or may be surface-modified differently.

The particles may be charged or have hydrophilic and/or hydrophobic properties through surface modification.

More specifically, in order to effectively support the CTGF gene transcript complementarily binding nucleic acid molecules, surface modification of the porous silica particles may be performed by having at least one substituent selected from the group consisting of amino, aminoalkyl, alkylamino, heterocyclic aromatic compound group containing a nitrogen atom, cyan and guanidine groups.

Surface modification may be performed, for example, by reacting a compound having a hydrophilic, hydrophobic, cationic or anionic substituent to be introduced with the particles, wherein the compound may be, for example, alkoxysilane having a C1 to C10 alkoxy group, but it is not limited thereto.

The alkoxysilane has one or more alkoxy groups, for example, 1 to 3 alkoxy groups. Further, there may be a substituent to be introduced into a site where the alkoxy group is not bound, or a substituent substituted with the same.

When alkoxysilane reacts with the porous silica particles, a covalent bond is formed between a silicon atom and an oxygen atom so that the alkoxysilane may be bound to the surface of the silicone particles and/or the inside of the pores. Since the alkoxysilane has a substituent to be introduced, the corresponding substituent may be introduced into the surface of the porous silica particles and/or the inside of the pores.

The reaction may be carried out by reacting the porous silica particles dispersed in a solvent with alkoxysilane.

The solvent may be water and/or an organic solvent, and the organic solvent may include, for example: ethers such as 1,4-dioxane (particularly cyclic ethers); halogenated hydrocarbons such as chloroform, methylene chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methylisobutylketone, γ-butyrolactone, 1,3-dimethyl-imidazolidinone, methylethylketone, cyclohexanone, cyclopentanone, 4-hydroxy-4-methyl-2-pentanone, etc.; aromatic carbon-based materials such as benzene, toluene, xylene, tetramethylbenzene, etc.; alkyl amides such as N,N-dimethylformamide, N,N-dibutylformamide, N,N-dimethylacetamide, N-methylpyrrolidone, etc.; alcohols such as methanol, ethanol, propanol, butanol, etc.; glycol ethers (cellosolve) such as ethyleneglycol monoethyl ether, ethyleneglycol monomethyl ether, ethyleneglycol monobutyl ether, diethyleneglycol monoethyl ether, diethyleneglycol monomethyl ether, diethyleneglycol monobutyl ether, propyleneglycol monomethyl ether, propyleneglycol monoethyl ether, dipropyleneglycol diethyl ether, triethyleneglycol monoethyl ether, etc.; others such as dimethylacetamide (DMAc), N,N-diethylacetamide, dimethylformamide (DMF), diethylformamide (DEF), N,N-dimethylacetamide (DMAc), N-methylpyrrolidone (NMP), N-ethylpyrrolidone (NEP), 1,3-dimethyl-2-imidazolidinone, N,N-dimethylmethoxyacetamide, dimethyl sulfoxide, pyridine, dimethyl sulfone, hexamethylphosphoamide, tetramethylurea, N-methylcarrolactam, tetrahydrofuran, m-dioxane, P-dioxane, 1,2-dimethoxyethane and the like. Specifically, alcohol, more specifically methanol may be used, but it is not limited thereto.

The positively charging may be performed by reacting the porous silica particles with alkoxysilane having a basic group such as a nitrogen-containing group, for example, an amino group or an aminoalkyl group. Specifically, N-[3-(trimethoxysilyl)propyl]ethylenediamine, N1-(3-trimethoxysilylpropyl)diethylenetriamine, (3-aminopropyl)trimethoxysilane, N-[3-(trimethoxysilyl)propyl]aniline, trimethoxy[3-(methylamino)propyl]silane, 3-(2-aminoethylamino)propyldimethoxymethylsilane, etc. may be used, but it is not limited thereto.

The negatively charging may be performed by reacting the porous silica particles with alkoxysilane having an acidic group such as a carboxyl group, a sulfonic acid group, a thiol group, etc. Specifically, (3-Mercaptopropyl) trimethoxysilane may be used, but it is not limited thereto.

The charging to non-charge (in an uncharged state rather than positive or negative charge) may be performed by reacting the porous silica particles with alkoxysilane having a common functional group having no charge. It is possible to charge with no charge by appropriately combining the positively charging and the negatively charging to offset positive and negative charges, but it is not limited thereto.

The hydrophilic property may be obtained by reacting the porous silica particles with alkoxysilane having a hydrophilic group, for example, hydroxyl group, carboxy group, amino group, carbonyl group, sulfhydryl group, phosphate group, thiol group, ammonium group, ester group, imide group, thioimide group, keto group, ether group, indene group, sulfonyl group, polyethyleneglycol group and the like. Specifically, N-[3-(trimethoxysilyl)propyl]ethylenediamine, N1-(3-trimethoxysilylpropyl)diethylenetriamine, (3-aminopropyl)trimethoxysilane, (3-mercaptopropyl) trimethoxysilane, trimethoxy [3-(methylamino)propyl]silane, 3-(2-aminoethylamino)propyldimethoxymethylsilane may be used, but it is not limited thereto.

The hydrophobic property may be obtained by reacting the porous silica particles with alkoxysilane having a hydrophobic substituent, for example, substituted or unsubstituted C1 to C30 alkyl group, substituted or unsubstituted C3 to C30 cycloalkyl group, substituted or unsubstituted C6 to C30 aryl group, substituted or unsubstituted C2 to C30 heteroaryl group, halogen group, C1 to C30 ester group, halogen-containing group and the like. Specifically, trimethoxy(octadecyl)silane, trimethoxy-n-octylsilane, trimethoxy(propyl)silane, isobutyl(trimethoxy)silane, trimethoxy(7-octen-1-yl)silane, trimethoxy(3,3,3-trifluoropropyl)silane, trimethoxy(2-phenylethyl)silane, vinyltrimethoxysilane, cyanomethyl, 3-(trimethoxysilyl)propyl] trithiocarbonate, (3-bromopropyl)trimethoxysilane, etc. may be used, but it is not limited thereto.

Further, in order to improve a binding ability of the silica particles to a nucleic acid molecule or material that complementarily binds to at least a portion of the transcript of poorly soluble (hydrophobic) CTGF gene through surface modification, hydrophobic substituents may be present inside of the pores of the particle. Further, in aspects of easy use and formulation, the surface of the particles may also be treated to have hydrophilic substituents. In addition, there may be a substituent on the surface of the particles in order to bind a nucleic acid molecule or material complementarily to at least a portion of transcript of another CTGF gene.

Further, the surface modification may be performed in combination. For example, surface modification may be performed twice or more on the outer surface of the particles or the inside of the pores. As a specific example, a compound including a carboxyl group may be bound to silica particles having amino groups introduced therein through amide bond in order to change the positively-charged particles to have different surface properties, but it is not limited thereto.

The reaction of the porous silica particles with alkoxysilane may be carried out, for example, under heating. The heating may be conducted at 80 to 180° C., for example, 80 to 160° C., 80 to 150° C., 100 to 160° C., 100 to 150° C., 110 to 150° C., etc. within the above range, but it is not limited thereto.

The reaction of the porous silica particles with alkoxysilane may be carried out for 4 to 20 hours, for example, 4 to 18 hours, 4 to 16 hours, 6 to 18 hours, 6 to 16 hours, 8 to 18 hours, 8 to 16 hours, 8 to 14 hours, 10 to 14 hours, etc. within the above range, but it is not limited thereto.

The reaction temperature, time and an amount of the compound used for surface modification may be desirably selected according to an extent of surface modification, and reaction conditions will vary depending on hydrophilic property, hydrophobic property and a level of charge with regard to the nucleic acid molecules or materials of the present invention. By controlling the hydrophilic property, hydrophobic property and the level of charge of the porous silica particles, a release rate of CTGF gene transcript complementarily binding nucleic acid molecules or materials may be controlled. For example, if the CTGF gene transcript complementarily binding nucleic acid molecules or materials have strong negative charge at neutral pH, the reaction temperature may be raised, the reaction time may be extended or the amount of the treated compound may be increased so as to make the porous silica particles to have strong positive charge, but it is not limited thereto.

Further, the porous silica particles of the present invention may be manufactured through, for example, preparation of small pore particles, pore expansion, surface modification, and internal pore modification.

Preparation of small pore particles and pore expansion may be performed by the above-described processes and, after preparation of the small pore particles and after pore expansion, washing and drying processes may be implemented.

If necessary, unreacted materials may be separated before washing, and separation of the unreacted materials may be conducted by separating the supernatant through centrifugation.

Centrifugation may be conducted at 6,000 to 10,000 rpm, and the centrifugation time may range from 3 to 60 minutes, for example, 3 to 30 minutes, 3 to 30 minutes, 5 to 30 minutes, etc. within the above range, but it is not limited thereto.

The washing after preparation of small pore particles may be conducted by a method/condition within the above-described range, but it is not limited thereto.

The washing after pore expansion may be conducted under more moderate conditions than the above embodiments. For example, washing may be conducted three times or less, but it is not limited thereto.

The surface modification and internal pore modification may be performed by the above-described processes, respectively. Herein, surface modification and then internal pore modification may be performed in this order, and a washing process may be further conducted between the above two processes.

When the washing is conducted in more moderated conditions after preparation of small pore particles and pore expansion, a reaction solution such as a surfactant used for particle production and pore expansion is filled in the pores so that the inside of the pores is not modified during surface modification and, instead, only the surface of the particles may be modified. Thereafter, the reaction solution inside of the pores may be washed out and removed.

Particle washing between the surface modification and the internal pore modification processes may be carried out using water and/or an organic solvent. Specifically, since different substances are dissolved in different solvents, water and the organic solvent may be used alternately once or several times, or the washing may be conducted with water or the organic solvent alone once or several times. The several times described above may be 2 times or more and 10 times or less, for example, 3 times or more and 10 times or less, 4 times or more and 8 times or less, 4 times or more and 6 times or less.

The washing may be carried out under centrifugation, for example at 6,000 to 10,000 rpm, and the centrifugation time may range from 3 to 60 minutes, for example, 3 to 30 minutes, 3 to 30 minutes, 5 to 30 minutes, etc. within the above range, but it is not limited thereto.

Alternatively, the washing may be conducted by filtering out particles through a filter without centrifugation. The filter may have pores in a size of less than or equal to the diameter of the porous silica particles. When filtering the reaction solution with such a filter as described above, only particles remain on the filter, which may be washed by pouring water and/or an organic solvent on the filter.

In the washing, water and the organic solvent may be used alternately once or several times, or the washing may be conducted with water or the organic solvent alone once or several times. The several times described above may be 2 times or more and 10 times or less, for example, 3 times or more and 10 times or less, 4 times or more and 8 times or less, 4 times or more and 6 times or less.

The drying may be conducted, for example, at 20 to 100° C., but it is not limited thereto, and may also be conducted in a vacuum state.

The CTGF gene transcript complementarily binding nucleic acid molecules may be supported on the surface of the porous silica particles and/or the inside of the pores. Herein, the supporting may be performed, for example, by mixing porous silica particles in a solvent with the CTGF gene transcript complementarily binding nucleic acid molecules.

The solvent may be water and/or an organic solvent, and the solvent may include, for example: ethers such as 1,4-dioxane (particularly cyclic ethers); halogenated hydrocarbons such as chloroform, methylene chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methylisobutylketone, cyclohexanone, etc.; aromatic carbon-based materials such as benzene, toluene, xylene, etc.; alkyl amides such as N,N-dimethylformamide, N,N-dibutylformamide, N,N-dimethylacetamide, N-methylpyrrolidone, etc.; alcohols such as methanol, ethanol, propanol, butanol and the like. Specifically, alcohol, more specifically methanol may be used, but it is not limited thereto.

Further, PBS (phosphate buffered saline solution), SBF (simulated body fluid), borate-buffered saline, tris-buffered saline may be used as the solvent.

A relative ratio of the porous silica particles to the nucleic acid molecules in the present invention is not particularly limited but may be 1:0.05 to 0.8 in weight ratio, for example, 1:0.05 to 0.7, 1:0.05 to 0.6, 1:0.1 to 0.8, 1:0.1 to 0.6, 1:0.2 to 0.8, 1:0.2 to 0.6, etc. within the above range.

The CTGF gene transcript complementarily binding nucleic acid molecules supported on the porous silica particles may be gradually released over an extended time. Such sustained release may be continuous or discontinuous, or linear or nonlinear. Further, the release may vary depending upon characteristics of the porous silica particles and/or interaction between the porous silica particles and the CTGF gene transcript complementarily binding nucleic acid molecules.

The CTGF gene transcript complementarily binding nucleic acid molecules supported on the porous silica particles are released when the porous silica particles are biodegraded. Specifically, the porous silica particles according to the present invention are slowly degraded to allow release of the CTGF gene transcript complementarily binding nucleic acid molecules in a sustained manner. Such release may be controlled by, for example, adjusting surface area, particle size, pore diameter, substituents on the surface of the particles and/or the inside of the pores, surface compactness, etc. with regard to the porous silica particles, but it is not limited thereto.

The CTGF gene transcript complementarily binding nucleic acid molecules supported on the porous silica particles may be released while being separated and diffused from the porous silica particles. Such release is influenced by correlations between the porous silica particles, the CTGF gene transcript complementarily binding nucleic acid molecules and release environment of the same. Therefore, regulating the correlations may control the release of the CTGF gene transcript complementarily binding nucleic acid molecules. For example, by enhancing or weakening a binding force of the porous silica particles to the CTGF gene transcript complementarily binding nucleic acid molecules through surface modification, the release of the CTGF gene transcript complementarily binding nucleic acid molecules may be controlled.

More specifically, in the case where the supported nucleic acid molecule or material that complementarily bind to at least a portion of the transcript of CTGF gene are poorly soluble (hydrophobic), the surface of the particles and/or the inside of the pores have hydrophobic substituents so as to increase a binding force of the porous silica particles to the CTGF gene transcript complementarily binding nucleic acid molecule or material, whereby the CTGF gene transcript complementarily binding nucleic acid molecule or material may be released in a sustained manner. For example, the porous silica particles may be surface-modified with alkoxysilane having a hydrophobic substituent.

As used herein, the term "poorly soluble" means to be insoluble, practically insoluble or only slightly soluble (in water), which is a word defined in "Pharmaceutical Science" 18$^{th}$ Edition (issued by U.S.P., Remington, Mack Publishing Company).

The poorly soluble material may have, for example, water solubility of less than 10 g/L, specifically, less than 5 g/L, and more specifically, less than 1 g/L at 1 atmosphere and 25° C., but it is not limited thereto.

When the supported CTGF gene transcript complementarily binding nucleic acid molecule or material is water-soluble (hydrophilic), the surface of the particles and/or the inside of the pores have hydrophilic substituents so as to increase a binding force of the porous silica particles to the CTGF gene transcript complementarily binding nucleic acid molecule or material, whereby the CTGF gene transcript complementarily binding nucleic acid CTGF gene transcript complementarily binding nucleic acid or material may be released in a sustained manner. For example, the porous silica particles may be surface-modified with alkoxysilane having a hydrophilic substituent.

For example, the water-soluble material may have a water solubility of 10 g/L or more at 1 atmosphere and 25° C., but it is not limited thereto.

In the case where the supported CTGF gene transcript complementarily binding nucleic acid molecule or material is charged, the surface of the particles and/or the inside of the pores are charged with opposite charges, so as to increase the binding force of the porous silica particles to the CTGF gene transcript complementarily binding nucleic acid molecule or material, whereby the CTGF gene transcript complementarily binding nucleic acid molecules may be released in a sustained manner. For example, the porous silica particles may be surface-modified with alkoxysilane having an acidic group or a basic group.

Specifically, if the CTGF gene transcript complementarily binding nucleic acid molecule or material is positively charged at neutral pH, the surface of the particles and/or the inside of the pores may be negatively charged at neutral pH so as to increase a binding force of the porous silica particles to the CTGF gene transcript complementarily binding nucleic acid molecule or material, whereby the CTGF gene transcript complementarily binding nucleic acid molecule or material may be released in a sustained manner. For example, the porous silica particles may be surface-modified with alkoxysilane having an acidic group such as a carboxyl group (—COOH), a sulfonic acid group (—SO$_3$H), etc.

Further, if the CTGF gene transcript complementarily binding nucleic acid molecule or material is negatively charged at neutral pH, the surface of the particles and/or the inside of the pores may be positively charged at neutral pH, so as to increase a binding force of the porous silica particles to the CTGF gene transcript complementarily binding nucleic acid molecule or material, whereby the CTGF gene transcript complementarily binding nucleic acid molecule or material may be released in a sustained manner. For example, the porous silica particles may be surface-modified with alkoxysilane having a basic group such as an amino group or any other nitrogen-containing group.

The CTGF gene transcript complementarily binding nucleic acid molecule or material may be released for a period of, for example, 7 days to 1 year or more, depending upon types of treatment to be required, release environments and types of porous silica particles to be used.

Further, since the porous silica particles of the present invention are 100% biodegradable, the CTGF gene transcript complementarily binding nucleic acid molecule or material may be 100% released.

As described above, the CTGF gene transcript complementarily binding nucleic acid molecule or material may have complementarity with the sequence of SEQ ID NO: 1, in an extent of 10 nucleotides (nt) or more, at least 11 nucleotides or more, 12 nucleotides or more, 13 nucleotides or more, 14 nucleotides or more, 15 nucleotides or more, 16 nucleotides or more, 17 nucleotides or more, or the entire 18 nucleotides. A detailed description thereof is as mentioned above.

The present invention provides a pharmaceutical composition for preventing or treating fibroproliferative diseases, including: a composition of inhibiting CTGF gene expression which includes porous silica particles carrying nucleic acid molecules complementarily bound to at least a portion of the transcript of CTGF gene described above.

Detailed descriptions of the nucleic acid molecules, porous silica particles, inhibition of CTGF gene expression, fibroproliferative diseases, various formulations of the pharmaceutical composition, and the like, are as mentioned above.

Hereinafter, the present invention will be described in detail with reference to the following examples.

Hereinafter, siRNA used in the present invention may be abbreviated as 'siCTGF'. Likewise, porous silica particles of the present invention may be abbreviated as 'DEGRADABALL or DDV', and DEGRADABALL carrying siCTGF may be abbreviated as 'LEM-S401'.

Experimental Procedure

1. Experimental Materials

DEGRADABALL and TAMRA-combined DEGRADABALL were provided by Lemonex, Inc. (Seoul, Korea), and cell counting kit-8 was purchased from Dojindo molecular technologies, Inc. (Maryland, USA). TGF-ß was purchased from Peprotech (New Jersey, USA), and 10% phosphate buffered saline (PBS), Dulbecco's Modified Eagle's Medium (DMEM), fetal bovine serum (FBS), Roswell Park Memorial Laboratory 1640 (RPMI 1640), penicillin-streptomycin and 0.05% trypsin-EDTA were purchased from WelGene (Korea). All nucleic acid molecules were synthesized by Lemonex (Seoul, Korea), and their sequences and nucleic acid molecule sequences used throughout the present specification are shown in Table 1 below. All PCR primers were purchased from Cosmogenetech (Seoul, Korea). Anti-mouse CTGF antibodies were purchased from Abcam (Cambridge, UK) and anti-mouse collagen 1 and 3 antibodies were purchased from Invitrogen (Carlsbad, CA, USA). Trizol cell lysis solution was purchased from Molecular Probes Invitrogen (Carlsbad, CA, USA) and all PCR reagents were purchased from TaKaRa Bio Inc. (Shiga, Japan). All chemicals were used as received.

TABLE 1

| | |
|---|---|
| Target sequence 1:<br>5'-CTC ATT AGA CTG GAA CTT-3' (SEQ ID NO: 108)<br>(Position in gene sequence: 1280) | siRNA GC content: 38.9%<br>siRNA Sense strand: SEQ ID NO: 1<br>5'-CUCAUUAGACUGGAACUU-3'<br>siRNA Antisense strand: SEQ ID NO: 2<br>5'-AAGUUCCAGUCUAAUGAG-3'<br>dsRNA: SEQ ID NO: 3<br>5'- CUCAUUAGACUGGAACUU UU UCU AAA G-3'<br>antisense PNA: SEQ ID NO: 87<br>5'-TTA GAC TGG AAC TTG A-3'<br>antisense PNA: SEQ ID NO: 88<br>5'-CAT TAG ACT GGA ACT T-3' |
| Target sequence 2:<br>5'-G GAA CTT GAA CTG ATT CA-3' (SEQ ID NO: 109)<br>(Position in gene sequence: 1291) | siRNA GC content: 38.9%<br>siRNA Sense strand: SEQ ID NO: 4<br>5'-GGAACUUGAACUGAUUCA-3'<br>siRNA Antisense strand: SEQ ID NO: 5<br>5'-UGAAUCAGUUCAAGUUCC-3'<br>dsRNA: SEQ ID NO: 6<br>5'-GGAACUUGAACUGAUUCAUU CCU UUC UAA AG-3' |
| Target sequence 3:<br>5'-CTG AGT GAC TCT ATA TAG CT-3' (SEQ ID NO: 110)<br>(Position in gene sequence: 2185) | siRNA GC content: 40.0%<br>siRNA Sense strand: SEQ ID NO: 7<br>5'-CUGAGUGACUCUAUAUAGCU-3'<br>siRNA Antisense strand: SEQ ID NO: 8<br>5'-AGCUAUAUAGAGUCACUCAG-3'<br>dsRNA: SEQ ID NO: 9<br>5'-CUGAGUGACUCUAUAUAGCU UU UCU AAA G-3' |
| Target sequence 4:<br>5'-GCA TGA AGA CAT ACC GAG C-3' (SEQ ID NO: 111)<br>(Position in gene sequence: 1030) | siRNA GC content: 52.6%<br>siRNA Sense strand: SEQ ID NO: 10<br>5'-GCAUGAAGACAUACCGAGC-3'<br>siRNA Antisense strand: SEQ ID NO: 11<br>5'-GCUCGGUAUGUCUUCAUGC-3'<br>dsRNA: SEQ ID NO: 12<br>5'-GCAUGAAGACAUACCGAGC UU UCU AAA G-3' |
| Target sequence 5:<br>5'-ATG TTT GCA CCT TTC TAG-3' (SEQ ID NO: 112)<br>(Position in gene sequence: 2296) | siRNA GC content: 38.9%<br>siRNA Sense strand: SEQ ID NO: 13<br>5'-AUGUUUGCACCUUUCUAG-3'<br>siRNA Antisense strand: SEQ ID NO: 14<br>5'-CUAGAAAGGUGCAAACAU-3'<br>dsRNA: SEQ ID NO: 15<br>5'-AUGUUUGCACCUUUCUAGUU CCU UUC UAA AG-3' |
| Target sequence 6:<br>5'-TG AGA GGA GAC AGC CAG T-3' (SEQ ID NO: 113)<br>(Position in gene sequence: 26) | siRNA GC content: 55.6%<br>siRNA Sense strand: SEQ ID NO: 16<br>5'-UGAGAGGAGACAGCCAGU-3'<br>siRNA Antisense strand: SEQ ID NO: 17<br>5'-ACUGGCUGUCUCCUCUCA-3'<br>dsRNA: SEQ ID NO: 18<br>5'-UGAGAGGAGACAGCCAGUUU CCU UUC UAA AG-3' |

TABLE 1-continued

| Target sequence 7:<br>5'-TTC GGT GGT ACG GTG TAC -3'(SEQ ID NO: 114)<br>(Position in gene sequence: 518) | siRNA GC content: 55.6%<br>siRNA Sense strand: SEQ ID NO: 19<br>5'-UUCGGUGGUACGGUGUAC-3'<br>siRNA Antisense strand: SEQ ID NO: 20<br>5'-GUACACCGUACCACCGAA-3'<br>dsRNA: SEQ ID NO: 21<br>5'-UUCGGUGGUACGGUGUACUU CCU UUC UAA AG-3' |
|---|---|
| Target sequence 8:<br>5'-TCC TTC CAG AGC AGC TGC AA-3'(SEQ ID NO: 115)<br>(Position in gene sequence: 549) | siRNA GC content: 55.0%<br>siRNA Sense strand: SEQ ID NO: 22<br>5'-UCCUUCCAGAGCAGCUGCAA-3'<br>siRNA Antisense strand: SEQ ID NO: 23<br>5'-UUGCAGCUGCUCUGGAAGGA-3'<br>dsRNA: SEQ ID NO: 24<br>5'-UCCUUCCAGAGCAGCUGCAA UU UCU AAA G-3' |
| Target sequence 9:<br>5'-TG TGT GAC GAG CCC AAG GA-3'(SEQ ID NO: 116)<br>(Position in gene sequence: 699) | siRNA GC content: 57.9%<br>siRNA Sense strand: SEQ ID NO: 25<br>5'-UGUGUGACGAGCCCAAGGA-3'<br>siRNA Antisense strand: SEQ ID NO: 26<br>5'-UCCUUGGGCUCGUCACACA-3'<br>dsRNA: SEQ ID NO: 27<br>5'-UGUGUGACGAGCCCAAGGA UU UCU AAA G-3' |
| Target sequence 10:<br>5'-TGC CTG GTC CAG ACC ACA GA-3'(SEQ ID NO: 117)<br>(Position in gene sequence: 801) | siRNA GC content: 60.0%<br>siRNA Sense strand: SEQ ID NO: 28<br>5'-UGCCUGGUCCAGACCACAGA-3'<br>siRNA Antisense strand: SEQ ID NO: 29<br>5'-UCUGUGGUCUGGACCAGGCA-3'<br>dsRNA: SEQ ID NO: 30<br>5'-UGCCUGGUCCAGACCACAGAUU CCU UUC UAA AG-3' |
| Target sequence 11:<br>5'-CAG GCT AGA GAA GCA GAG-3'(SEQ ID NO: 118)<br>(Position in gene sequence: 890) | siRNA GC content: 55.6%<br>siRNA Sense strand: SEQ ID NO: 31<br>5'-CAGGCUAGAGAAGCAGAG-3'<br>siRNA Antisense strand: SEQ ID NO: 32<br>5'-CUCUGCUUCUCUAGCCUG-3'<br>dsRNA: SEQ ID NO: 33<br>5'-CAGGCUAGAGAAGCAGAG UU UCU AAA G-3' |
| Target sequence 12:<br>5'-TGT GCA TGG TCA GGC CTT-3'(SEQ ID NO: 119)<br>(Position in gene sequence: 913) | siRNA GC content: 55.6%<br>siRNA Sense strand: SEQ ID NO: 34<br>5'-UGUGCAUGGUCAGGCCUU-3'<br>siRNA Antisense strand: SEQ ID NO: 35<br>5'-AAGGCCUGACCAUGCACA-3'<br>dsRNA: SEQ ID NO: 36<br>5'-UGUGCAUGGUCAGGCCUUUU CCU UUC UAA AG-3' |
| Target sequence 13:<br>5'-TGA TTT CAG TAG CAC AAG-3'(SEQ ID NO: 120)<br>(Position in gene sequence: 1330) | siRNA GC content: 38.9%<br>siRNA Sense strand: SEQ ID NO: 37<br>5'-UGAUUUCAGUAGCACAAG-3'<br>siRNA Antisense strand: SEQ ID NO: 38<br>5'-CUUGUGCUACUGAAAUCA-3'<br>dsRNA: SEQ ID NO: 39<br>5'-UGAUUUCAGUAGCACAAGUU CCU UUC UAA AG-3' |
| Target sequence 14:<br>5'-TAG CGT GCT CAC TGA CCT-3'(SEQ ID NO: 121)<br>(Position in gene sequence: 1623) | siRNA GC content: 55.6%<br>siRNA Sense strand: SEQ ID NO: 40<br>5'-UAGCGUGCUCACUGACCU-3'<br>siRNA Antisense strand: SEQ ID NO: 41<br>5'-AGGUCAGUGAGCACGCUA-3'<br>dsRNA: SEQ ID NO: 42<br>5'-UAGCGUGCUCACUGACCUUU CCU UUC UAA AG-3' |
| Target sequence 15:<br>5'-CTG ATT CGA ATG ACA CTG TT-3'(SEQ | siRNA GC content: 40.0%<br>siRNA Sense strand: SEQ ID NO: 43<br>5'-CUGAUUCGAAUGACACUGUU-3'<br>siRNA Antisense strand: SEQ ID NO: 44<br>5'-AACAGUGUCAUUCGAAUCAG-3' |

TABLE 1-continued

| | |
|---|---|
| ID NO: 122)<br>(Position in gene sequence: 1742) | dsRNA: SEQ ID NO: 45<br>5'-CUGAUUCGAAUGACACUGUUUU CCU UUC UAA AG-3' |
| Target sequence 16:<br>5'-CAG ATT GTT TGC AAA GGG-3'(SEQ ID NO: 123)<br>(Position in gene sequence: 2081) | siRNA GC content: 44.4%<br>siRNA Sense strand: SEQ ID NO: 46<br>5'-CAGAUUGUUUGCAAAGGG-3'<br>siRNA Antisense strand: SEQ ID NO: 47<br>5'-CCCUUUGCAAACAAUCUG-3'<br>dsRNA: SEQ ID NO: 48<br>5'-CAGAUUGUUUGCAAAGGGUU CCU UUC UAA AG-3' |
| Target sequence 17:<br>5'-GCA TCA GTG TCC TTG GCA-3'(SEQ ID NO: 124)<br>(Position in gene sequence: 2102) | siRNA GC content: 55.6%<br>siRNA Sense strand: SEQ ID NO: 49<br>5'-GCAUCAGUGUCCUUGGCA-3'<br>siRNA Antisense strand: SEQ ID NO: 50<br>5'-UGCCAAGGACACUGAUGC-3'<br>dsRNA: SEQ ID NO: 51<br>5'-GCAUCAGUGUCCUUGGCAUU CCU UUC UAA AG-3' |
| Target sequence 18:<br>5'-GAC ATT AAC TCA TTA GAC-3'(SEQ ID NO: 125)<br>(Position in gene sequence: 1272) | siRNA GC content: 33.3%<br>siRNA Sense strand: SEQ ID NO: 52<br>5'-GACAUUAACUCAUUAGAC-3'<br>siRNA Antisense strand: SEQ ID NO: 53<br>5'-GUCUAAUGAGUUAAUGUC-3'<br>dsRNA: SEQ ID NO: 54<br>5'-GACAUUAACUCAUUAGAC UU UCU AAA G-3' |
| Target sequence 19:<br>5'-AAC TCA TTA GAC TGG AAC-3'(SEQ ID NO: 126)<br>(Position in gene sequence: 1278) | siRNA GC content: 38.9%<br>siRNA Sense strand: SEQ ID NO: 55<br>5'-AACUCAUUAGACUGGAAC-3'<br>siRNA Antisense strand: SEQ ID NO: 56<br>5'-GUUCCAGUCUAAUGA GUU-3'<br>dsRNA: SEQ ID NO: 57<br>5'-AACUCAUUAGACUGGAAC UU UCU AAA G-3'<br>antisense PNA: SEQ ID NO: 89<br>5'-TCC AGT CTA ATG AGT-3'<br>antisense PNA: SEQ ID NO: 90<br>5'-TTC CAG TCT AAT GAG T-3' |
| Target sequence 20:<br>5'-ACT CAT TAG ACT GGA ACT-3'(SEQ ID NO: 127)<br>(Position in gene sequence: 1279) | siRNA GC content: 38.9%<br>siRNA Sense strand: SEQ ID NO: 58<br>5'-ACUCAUUAGACUGGAACU-3'<br>siRNA Antisense strand: SEQ ID NO: 59<br>5'-AGUUCCAGUCUAAUGAGU-3'<br>dsRNA: SEQ ID NO: 60<br>5'-ACUCAUUAGACUGGAACU UU UCU AAA G-3'<br>antisense PNA: SEQ ID NO: 91<br>5'-AGT TCC AGT CTA ATG A-3' |
| Target sequence 21:<br>5'-TTA GAC TGG AAC TTG AAC-3'(SEQ ID NO: 128)<br>(Position in gene sequence: 1284) | siRNA GC content: 38.9%<br>siRNA Sense strand: SEQ ID NO: 61<br>5'-UUAGACUGGAACUUGAAC-3'<br>siRNA Antisense strand: SEQ ID NO: 62<br>5'-GUUCAAGUUCCAGUCUAA-3'<br>dsRNA: SEQ ID NO: 63<br>5'-UUAGACUGGAACUUGAACUU UCU AAA G-3'<br>antisense PNA: SEQ ID NO: 92<br>5'-TCA AGT TCC AGT CTA A-3'<br>antisense PNA: SEQ ID NO: 93<br>5'-TTC AAG TTC CAG TCT A-3' |
| Target sequence 22:<br>5'-ATT AGA CTG GAA CTT GAA-3'(SEQ ID NO: 129)<br>(Position in gene sequence: 1283) | siRNA GC content: 33.3%<br>siRNA Sense strand: SEQ ID NO: 64<br>5'-AUUAGACUGGAACUUGAA-3'<br>siRNA Antisense strand: SEQ ID NO: 65<br>5'-UUCAAGUUCCAGUCUAAU-3'<br>dsRNA: SEQ ID NO: 66<br>5'-AUUAGACUGGAACUUGAAUU UCU AAA G-3'<br>antisense PNA: SEQ ID NO: 94<br>5'-CAA GTT CCA GTC TAA T-3'<br>antisense PNA: SEQ ID NO: 95<br>5'-TTC AAG TTC CAG TCT A-3' |
| Target sequence 23:<br>5'-CAT TAG | siRNA GC content: 38.9%<br>siRNA Sense strand: SEQ ID NO: 67<br>5'-CAUUAGACUGGAACUUGA-3' |

TABLE 1-continued

| | |
|---|---|
| ACT GGA ACT TGA-3' (SEQ ID NO: 130) (Position in gene sequence: 1282) | siRNA Antisense strand: SEQ ID NO: 68<br>5'-UCAAGUUCCAGUCUAAUG-3'<br>dsRNA: SEQ ID NO: 69<br>5'-CAUUAGACUGGAACUUGAUU UCU AAA G-3'<br>antisense PNA: SEQ ID NO: 96<br>5'-CAA GTT CCA GTC TAA T-3'<br>antisense PNA: SEQ ID NO: 97<br>5'-TCA AGT TCC AGT CTA A-3' |
| Target sequence 24:<br>5'-TCA TTA GAC TGG AAC TTG-3' (SEQ ID NO: 131) (Position in gene sequence: 1281) | siRNA GC content: 38.9%<br>siRNA Sense strand: SEQ ID NO: 70<br>5'-UCAUUAGACUGGAACUUG-3'<br>siRNA Antisense strand: SEQ ID NO: 71<br>5'-CAAGUUCCAGUCUAAUGA-3'<br>dsRNA: SEQ ID NO: 72<br>5'-UCAUUAGACUGGAACUUGUU UCU AAA G-3'<br>antisense PNA: SEQ ID NO: 98<br>5'-AGT TCC AGT CTA ATG A-3'<br>antisense PNA: SEQ ID NO: 99<br>5'-CAA GTT CCA GTC TAA T-3' |
| Mouse CTGF siRNA | siRNA Sense strand: SEQ ID NO: 73<br>5'-gcaccagugu gaagacaua-3'<br>siRNA Antisense strand: SEQ ID NO: 74<br>5'-uaugucuuca cacugguge-3' |
| Human β-actin Primer | Forward: SEQ ID NO: 75<br>5' gctcgtcgac aagggctc-3'<br>Reverse: SEQ ID NO: 76<br>5'-caaacatgat ctgggtca-3' |
| Human CTGF Primer | Forward: SEQ ID NO: 77<br>5'-caagggcctc ttctgtgact-3'<br>Reverse: SEQ ID NO: 78<br>5'-ccgtcggtac atactccaca-3' |
| Mouse β-actin Primer | Forward: SEQ ID NO: 79<br>5'-gcctcccttc ttgggtatgg aa-3'<br>Reverse: SEQ ID NO: 80<br>5'-cagctcagta acagtccgcc-3' |
| Mouse CTGF Primer | Forward: SEQ ID NO: 81<br>5'-gggcctcttc tgcgatttc-3'<br>Reverse: SEQ ID NO: 82<br>5'-atccaggcaa gtgcattggt a-3' |
| Mouse Collagen 1 Primer | Forward: SEQ ID NO: 83<br>5'-gagcggagag tactggatcg-3'<br>Reverse: SEQ ID NO: 84<br>5'-gttcgggctg atgtaccagt-3' |
| Mouse Collagen 3 Primer | Forward: SEQ ID NO: 85<br>5'-agctttgtgc aaagtggaac ctgg-3'<br>Reverse: SEQ ID NO: 86<br>5'-caaggtggct gcatcccaat tcat-3' |

2. Animal Model

All animal experiments were performed in compliance with the Institutional Animal Care and Use Committees (IACUC) of Seoul National University, and C57BL/6 male rats (5 weeks) were purchased from ORIENT BIO (Seongnam, Korea).

3. Measurement of Cell Viability

A549 and HaCaT cells were seeded in 96-well culture plates with 100 μl of growth medium (50-70% confluency) at a density of 10,000 cells per well. Cells were treated with an appropriate concentration of DEGRADABALL in a serum-containing medium and incubated at 37° C. for 24 hours. After incubation, the cells were washed twice with 1×PBS, and then 100 μl of serum-free medium containing 10 μl of CCK-8 was added, followed by further incubation for 1 hour. The optical density of each well in the culture plate was measured at 450 nm wavelength. Mean and standard deviation of the deviation of triplicates were calculated and plotted.

4. Cell-Based CTGF Knockdown Assay

In order to demonstrate CTGF gene silencing efficiency of LEM-S401 in vitro, 500 μl of LEM-S401 (12.5, 25, 50, and 100 nM) in a serum-free medium was used to treat A549 and HaCaT cells in the plates, which were inoculated with 25,000 cells of confluency per well. After 6 hours of incubation in a humidified 5% $CO_2$ incubator at 37° C., the serum-free culture was removed and washed twice with 1×PBS, followed by replacing the medium with a serum-containing cell medium. After 6 hours again, the serum-containing culture medium was removed and washed with 1×PBS. 500 μl of TGF-ß (2 ng/ml) was used to treat cells in the serum-containing medium and, after 12 hours of culture for CTGF induction, total RNA was extracted using Trizol.

In order to determine a duration of CTGF knockdown by LEM-S401. A549 and HaCaT cells were treated with 500 μl of LEM-S401 (50 nM siCTGF) containing LNP and siCTGF (50 nM) in a serum-free medium. After 6 hours of incubation at 37° C. in a humidified 5% CO$_2$ incubator, the serum-free culture was removed and washed twice with 1×PBS, followed by replacing the medium with a serum-containing cell medium. After incubation for the indicated time, cells were treated with 500 μl of TGF-ß (2 ng/ml) in the serum-containing culture medium, and cells were further incubated for 24 hours for CTGF induction. Total RNA was extracted using Trizol.

5. RT-PCR

All RNAs extracted in vitro and in vivo were used for thermal cycling using the following reaction conditions. cDNA synthesis: 1 cycle of inactivation for 5 minutes at 65° C., 2 minutes at 42° C., 50 minutes at 42° C., and 15 minutes at 70° C., amplification process: 30 cycles for 30 seconds at 95° C., 60 seconds at 55° C. and 30 seconds at 72° C.

6. In Vivo Imaging of siCTGF and Porous Silica Particles

30 μl of LEM-S401 (33 mM) (FITC-conjugated siCTGF and TAMRA-conjugated DEGRADABALL) were injected into the mouse skin at seven different sites. After sacrifice, fluorescence images of the excised mouse skin were taken using a FOBI in vivo imaging device (NeoScience Co., Ltd., Seoul, Korea). The obtained skin sample was placed in 4% PFA solution. The sample was inserted into paraffin and cut to 10 μm thickness. After dehydration, the sections were stained with DAPI Samples were observed with a BX71 microscope equipped with a 20× objective lens (Olympus, Tokyo, Japan).

7. In Vivo Experiment Using Mouse Skin Wound Model

Mouse skin was punctured to injure using a biopsy punch (4 mm). Over time, silicone splints (outer 15 mm, inner 8 mm) were sutured around the wound using a black silk thread in order to clearly observe the wound. 30 μL of LEM-S401 (3 mM) in 1×PBS was injected subcutaneously every 4 days (4 days, 8 days, and 12 days) at 4 different sites around the wound. The wounds were managed with changing Tegaderm and bandages every other day, and 16 days later, mice were sacrificed.

In order to demonstrate that LEM-S401 can inhibit CTGF expression during tissue remodeling, a hole was penetrated in the mouse skin, wounded using a biopsy punch (4 mm) and wrapped with a band. After the wound was completely closed, 30 μl of LEM-S401 (33 mM) in 1×PBS was injected subcutaneously into the wound site at 4 different sites every 4 days (day 10, day 14, day 18, and day 22), and mice were sacrificed on day 26.

8. Immunohistochemistry

Mouse skin sample was incubated in 4% PFA solution for 24 hours at 4° C. The sample was then inserted into paraffin and sections were prepared with 10 μm thickness. The sectioned samples were dehydrated and incubated twice for 10 minutes each in a permeate solution (0.2% tween 20 in 1×PBS). Then, the samples were incubated for 45 minutes in a humidified atmospheric blocking solution (5% normal goat serum, 0.2% tween 20 in 1×PBS). The samples were incubated in a humidification chamber at room temperature for 3 hours together with a primary antibody solution containing 0.2% tween 20 that has a 1:100 dilution of 2% normal goat serum and antibody in PBS. The samples were rinsed three times for 10 minutes each in a permeate solution and incubated at room temperature for 2 hours together with a secondary antibody dilution solution containing 2% normal goat serum and 0.2% tween 20 in 1×PBS. The samples were washed with a permeate solution and stained with DAPI. The samples were observed under a BX71 microscope equipped with a 20× objective lens (Olympus, Tokyo, Japan).

9. Porous Silica Particles (DDV or DEGRADABALL)

9-1. Preparation of Porous Silica Particles (1) Preparation of Porous Silica Particles 1) Preparation of Small Pore Particles 960 mL of distilled water (DW) and 810 mL of MeOH were put into a 2 L round bottom flask. 7.88 g of CTAB was added to the flask, followed by rapid addition of 4.52 mL of 1 M NaOH under stirring. After adding a homogeneous mixture while stirring for 10 minutes, 2.6 mL of TMOS was further added. After stirring for 6 hours to mix uniformly, the reaction solution was aged for 24 hours.

Then, the reaction solution was centrifuged at 8000 rpm and 25° C. for 10 minutes to remove the supernatant, centrifuged at 8000 rpm and 25° C. for 10 minutes, and washed five times with ethanol and distilled water alternately.

Thereafter, the resultant product was dried in an oven at 70° C. to harvest 1.5 g of powdery microporous silica particles (pore average diameter of 2 nm and particle size of 200 nm).

2) Pore Expansion 1.5 g of microporous silica particle powder was added to 10 ml of ethanol and subjected to ultrasonic dispersion, and 10 ml of water and 10 ml of TMB (trimethyl benzene) were further added, followed by ultrasonic dispersion.

Thereafter, the dispersion was placed in an autoclave and reacted at 160° C. for 48 hours.

The reaction was initiated at 25° C. and performed while raising the temperature at a rate of 10° C./min, then slowly cooled in an autoclave at a rate of 1 to 10° C./min.

The cooled reaction solution was centrifuged at 8000 rpm for 10 minutes at 25° C. to remove the supernatant, and centrifuged at 8000 rpm for 10 minutes at 25° C. and washed five times with ethanol and distilled water alternately.

Then, the product was dried in an oven at 70° C. to harvest powdery porous silica particles (pore diameter of 10 to 15 nm, and particle size of 200 nm).

3) Calcination

The porous silica particles prepared in 2) were put in a glass vial, heated at 550° C. for 5 hours, and cooled slowly to room temperature after completing the reaction to prepare particles.

(2) Preparation of Porous Silica Particles

Porous silica particles were prepared by the same method as 9-1-(1), except that the reaction conditions at the time of pore expansion were changed to 140° C. and 72 hours.

(3) Preparation of Porous Silica Particles (10 L Scale)

Porous silica particles were prepared by the same method as Example 9-1-(1), except that a 5 times larger container was used and each material was used in a 5 times capacity.

(4) Preparation of Porous Silica Particles (Particle Size of 300 nm)

Porous silica particles were prepared by the same method as 9-1-(1), except that 920 ml of distilled water and 850 ml of methanol were used to prepare the small pore particles.

(5) Preparation of Porous Silica Particles (Particle Size of 500 nm)

Porous silica particles were prepared by the same method as 9-1-(1), except that 800 ml of distilled water, 1010 ml of methanol, and 10.6 g of CTAB were used to prepare the small pore particles.

(6) Preparation of Porous Silica Particles (Particle Size of 1000 nm)

Porous silica particles were prepared by the same method as 9-1-(1), except that 620 ml of distilled water. 1380 ml of methanol, and 7.88 g of CTAB were used to prepare the small pore particles.

(7) Preparation of Porous Silica Particles (Pore Diameter of 4 nm)

Porous silica particles were prepared by the same method as 9-1-(1), except that 2.5 ml of TMB was used for pore expansion.

(8) Preparation of Porous Silica Particles (Pore Diameter of 7 nm)

Porous silica particles were prepared by the same method as 9-1-(1), except that 4.5 mL of TMB was used for pore expansion.

(9) Preparation of Porous Silica Particles (Pore Diameter of 17 nm)

Porous silica particles were prepared by the same method as 9-1-(1), except that 11 mL of TMB was used for pore expansion.

(10) Preparation of Porous Silica Particles (Pore Diameter of 23 nm)

Porous silica particles were prepared by the same method as 9-1-(1), except that 12.5 ml of TMB was used for pore expansion.

(11) Preparation of Porous Silica Particles (Dual Modification)

1) Preparation of Small Pore Particles

Small pore particles were prepared by the same method as Example 9-1-(1)-1).

2) Pore Expansion

Small pore particles were reacted with TMB, cooled and centrifuged by the same method as Example 9-1-(1)-2) to remove the supernatant. Thereafter, the remaining solution was centrifuged under the same conditions as Example 9-1-(1)-2), washed three times with ethanol and distilled water alternately, and then dried under the same conditions as Example 9-1-(1)-2), thereby harvesting powdery porous silica particles (pore diameter 10 to 15 nm, and particle size of 200 nm).

3) Surface Modification

After dispersing 0.8 g to 1 g of porous silica particles having expanded pores in 50 ml of toluene, 5 mL of (3-aminopropyl)triethoxysilane was added thereto, followed by heating under reflux at 120° C. for 12 hours. The procedure is followed by the washing and drying procedures described above, followed by 1 mL of triethylene glycol (PEG3, 2-[2-(2-methoxyethoxy)ethoxy] acetic acid) and 100 mg of EDC (1-ethyl-3-(3-dimethylaminopropyl)carbodiimide) and 200 mg of N-hydroxysuccinimide (NHS) were dispersed in 30 ml of PBS and allowed to react at room temperature for 12 hours under stirring. The product was then washed and dried.

Since the reaction solution of the previous step remained inside of the pores, the inside of the pores was not modified.

4) Washing Inside Pores 800 mg of surface-modified particle powder was dissolved in 40 ml of 2M HCl/ethanol and refluxed under vigorous stirring for 12 hours.

Thereafter, the cooled reaction solution was centrifuged at 8000 rpm for 10 minutes to remove the supernatant, centrifuged at 8000 rpm and 25° C. for 10 minutes, and washed five times with ethanol and distilled water alternately.

Thereafter, the product was dried in an oven at 70° C., thereby harvesting powdery porous silica particles.

5) Modifying Inside Pores (i) A propyl group was introduced into the pore by the same method as Example 9-2-(2)-1) described below.

(ii) An octyl group was introduced into the pore by the same method as Example 9-2-(2)-2) described below.

9-2. Surface Modification of Porous Silica Particles (1) Positively Charging

1) Particles with Particle Size of 300 nm

The porous silica particles of Example 9-1-(4) were reacted with (3-aminopropyl)triethoxysilane (APTES) to be positively charged.

Specifically, 100 mg of porous silica particles were dispersed in a 10 mL toluene in a 100 mL round bottom flask with a bath sonicator. Then, 1 mL of APTES was added and stirred at 400 rpm and 130° C. for 12 hours.

After the reaction, the product was slowly cooled to room temperature and centrifuged at 8000 rpm for 10 minutes to remove the supernatant, further centrifuged at 8000 rpm and 25° C. for 10 minutes, and then washed five times with ethanol and distilled water alternately.

Thereafter, the product was dried in an oven at 70° C. to harvest powdery porous silica particles having an amino group on the surface thereof and inside of the pores.

2) Particles with Particle Size of 200 nm (i) The porous silica particles of Example 9-1-(1) were positively charged by reacting the particles with (3-aminopropyl) triethoxysilane (APTES), and were modified by the same method as 9-2-(1)-1), except that 0.4 ml of APTES was added and the reaction time was 3 hours.

(ii) The porous silica particles of Example 9-1-(9) were positively charged by reacting the particles with (3-aminopropyl) triethoxysilane (APTES), and were modified by the same method as 9-2-(1)-1).

(iii) The porous silica particles of Example 9-1-(10) were positively charged by reacting the particles with (3-aminopropyl) triethoxysilane (APTES), and were modified by the same method as 9-2-(1)-1).

(2) Introduction of Hydrophobic Groups

1) Propyl Group

The porous silica particles of Example 9-1-(1) were reacted with trimethoxy(propyl)silane to introduce propyl groups into the surface of the particles and inside of the pores, and were subjected to modification by the same method as Example 9-2-(1), except that 0.35 ml of trimethoxy(propyl)silane was added instead of APTES, followed by 12 hours of reaction.

2) Octyl Group

The porous silica particles of Example 9-1-(1) were reacted with trimethoxy-n-octylsilane to introduce propyl groups on the surface of the particles and inside of the pores, and were subjected to modification by the same method as Example 9-2-(1), except that 0.5 ml of trimethoxy-n-octylsilane was added instead of APTES, followed by 12 hours of reaction.

(3) Negatively Charging

1) Carboxyl Group

The porous silica particles of Example 9-1-(1) were negatively charged by reacting the particles with succinic anhydride.

Further, the charged particles were subjected to modification by the same method as Example 9-2-(1)-1), except that DMSO (dimethyl sulfoxide) was used instead of toluene, 80 mg of succinic anhydride was added instead of APTES to allow reaction at room temperature for 24 hours under stirring, and DMSO was used instead of distilled water.

2) Thiol Group

The particles were subjected to modification by the same method as Example 9-2-(1)-1), except that 1.1 mL of MPTES was used instead of APTES.

3) Sulfonic Acid Group 100 mg of the porous silica nanoparticles of Example 9-2-(3)-2) were dispersed in 1 ml of 1 M aqueous sulfuric acid solution and 20 ml of 30% hydrogen peroxide solution, and stirred at room temperature to induce oxidation, thereby oxidizing a thiol group into a sulfonic acid group. Thereafter, the product was washed and dried by the same method as Example 9-2-(1)-1).

9-3. Support of Nucleic Acid Molecules

10 μg of porous silica particles of Example 9-2-(1)-2)-② and 50 pmol of nucleic acid molecules were mixed under 1×PBS conditions, and then placed at room temperature for 30 minutes to complete loading.

Experimental Results

1. Analysis of CTGF Expression Inhibition by Inventive Nucleic Acid Molecules

According to the above examples, inhibition rates of CTGF expression of the prepared nucleic acid molecules (PNA, siRNA or dsRNA; see Table 1) are shown in Tables 2 and 3 below.

Referring to Tables 1 and 2 below, nucleic acid molecules including a strand having complementarity of at least 10 nucleotides with the sequence of SEQ ID NO: 1 (that is: siRNA comprised of a sense RNA having the sequence of SEQ ID NO: 1 and an antisense RNA having the sequence of SEQ ID NO: 2; dsRNA comprised of a strand having a sequence of SEQ ID NO: 3 and another strand complementary thereto; siRNA comprised of a sense RNA having a sequence of SEQ ID NO: 52 and an antisense RNA having a sequence of SEQ ID NO: 53; dsRNA comprised of a strand having a sequence of SEQ ID NO: 54 and another strand complementary thereto; siRNA comprised of a sense RNA having a sequence of SEQ ID NO: 55 and an antisense RNA having a sequence of SEQ ID NO: 56, dsRNA comprised of a strand having a sequence of SEQ ID NO: 57 and another strand complementary thereto; siRNA comprised of a sense RNA having a sequence of SEQ ID NO: 58 and an antisense RNA having a sequence of SEQ ID NO: 59, dsRNA comprised of a strand having a sequence of SEQ ID NO: 60 and another strand complementary thereto; siRNA comprised of a sense RNA having a sequence of SEQ ID NO: 61 and an antisense RNA having a sequence of SEQ ID NO: 62; dsRNA comprised of a strand having a sequence of SEQ ID NO: 63 and another strand complementary thereto, siRNA comprised of a sense RNA having a sequence of SEQ ID NO: 64 and an antisense RNA having a sequence of SEQ ID NO: 65; dsRNA comprised of a strand having a sequence of SEQ ID NO: 66 and another strand complementary thereto; siRNA comprised of a sense RNA having a sequence of SEQ ID NO: 67 and an antisense RNA having a sequence of SEQ ID NO: 68; dsRNA comprised of a strand having a sequence of SEQ ID NO: 69 and another strand complementary thereto; siRNA comprised of a sense RNA having a sequence of SEQ ID NO: 70 and an antisense RNA having a sequence of SEQ ID NO: 71; dsRNA comprised of a strand having a sequence of SEQ ID NO: 72 and another strand complementary thereto; and an antisense PNA comprised of one sequence selected from the group consisting of sequences of SEQ ID NO: 87 to SEQ ID NO: 99) exhibited a inhibition rate of more than 90%. On the other hand, it could be seen that other nucleic acid molecules not satisfying the above configurations showed low inhibition rate of less than 75%.

In particular, the nucleic acid molecule with a strand having complementarity of only 7 nucleotides (that is: siRNA comprised of a sense RNA having the sequence of SEQ ID NO: 4 and an antisense RNA having the sequence of SEQ ID NO: 5; dsRNA comprised of a strand having the sequence of SEQ ID NO: 6 and another strand complementary thereto) exhibited considerably lower expression inhibitory ability such as an inhibition rate of about 60%, suggesting that technical significance is achieved when the complementarity with the sequence of SEQ ID NO: 1 is 10 nucleotides or more.

Among them, siRNA comprised of a sense RNA having the sequence of SEQ ID NO: 1 and an antisense RNA having the sequence of SEQ ID NO: 2, which includes the strand complementary to the sequence of SEQ ID NO: 1 with the complementarity of all 18 nucleotides as well as the highest expression inhibitory ability, or dsRNA comprised of a strand having the sequence of SEQ ID NO: 3 and another strand complementary thereto was selected and used in the following experiments.

TABLE 2

| Sequence number ("/" means pair between sense strand and antisense strand) | Expression inhibition rate (%) | Sequence number | Expression inhibition rate (%) |
|---|---|---|---|
| 1/2 or 3 | 93.7 | 37/38 or 39 | 74.6 |
| 4/5 or 6 | 62.4 | 40/41 or 42 | 71.8 |
| 7/8 or 9 | 67.2 | 43/44 or 45 | 63.5 |
| 10/11 or 12 | 72.6 | 46/47 or 48 | 74.2 |
| 13/14 or 15 | 74.1 | 49/50 or 51 | 71.6 |
| 16/17 or 18 | 61.3 | 52/53 or 54 | 90.3 |
| 19/20 or 21 | 74.7 | 55/56 or 57 | 90.1 |
| 22/23 or 24 | 72.3 | 58/59 or 60 | 91.9 |
| 25/26 or 27 | 67.8 | 61/62 or 63 | 92.2 |
| 28/29 or 30 | 63.5 | 64/65 or 66 | 91.5 |
| 31/32 or 33 | 71.6 | 67/68 or 69 | 92.8 |
| 34/35 or 36 | 72.9 | 70/71 or 72 | 91.6 |

TABLE 3

| PNA Sequence number | Expression inhibition rate (%) | PNA Sequence number | Expression inhibition rate (%) |
|---|---|---|---|
| 87 | 90.3 | 94 | 92.1 |
| 88 | 90.1 | 95 | 90.5 |
| 89 | 91.2 | 96 | 91.7 |
| 90 | 90.7 | 97 | 90.4 |
| 91 | 91.5 | 98 | 90.2 |
| 92 | 90.2 | 99 | 91.4 |
| 93 | 91.3 | | |

2. Porous Silica Particles (DDV or DEGRADABALL)

2-1. Identification of Particle Formation and Pore Expansion

Small pore particles and porous silica particles prepared in Experimental Examples 9-1-(1) to (3) were observed under a microscope to determine whether the small pore particles were uniformly formed or the pores were sufficiently expanded to uniformly form the porous silica particles (FIGS. 28 to 31).

Figure 28:
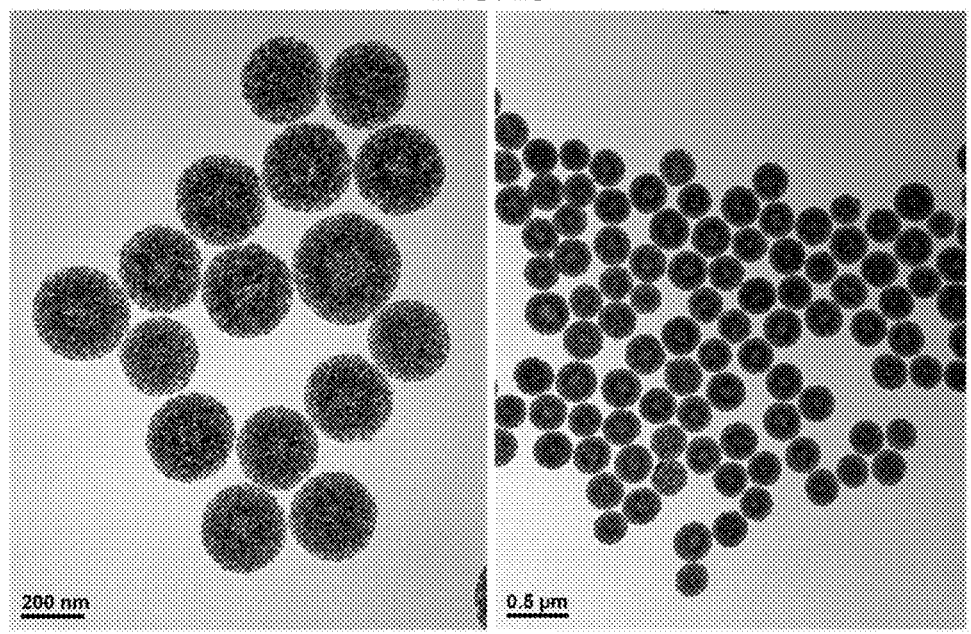
FIG. 28 is micrographs of porous silica particles according to one embodiment of the present invention.
Figure 29:
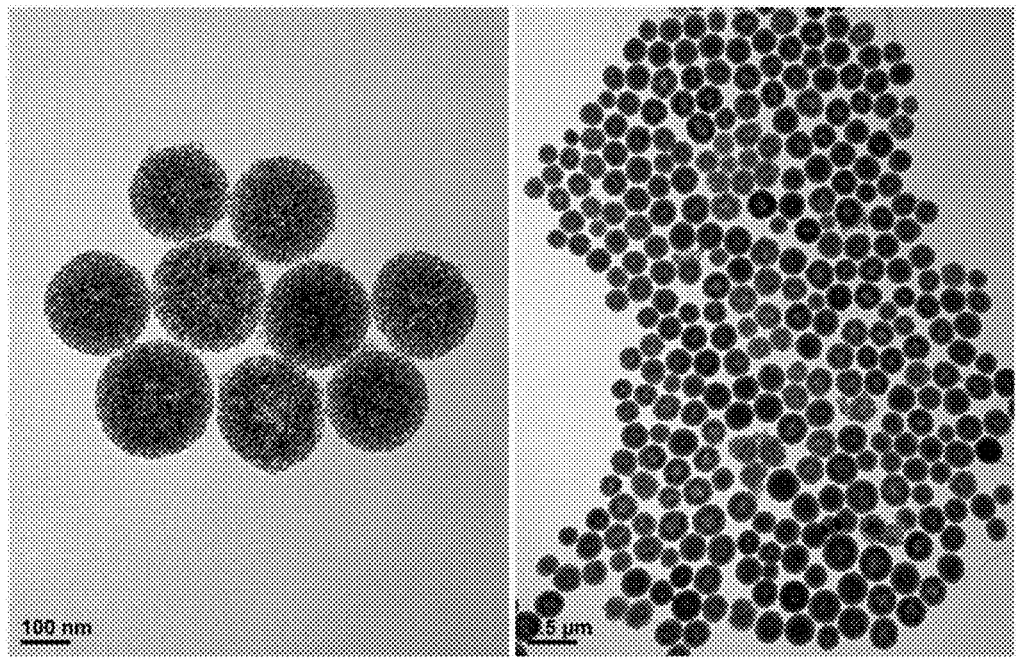
FIG. 29 is micrographs of porous silica particles according one embodiment of the present invention.

FIG. 28 is photographs of the porous silica particles in Experimental Example 9-1-(1), FIG. 29 is photographs of the porous silica particles in Experimental Example 9-1-(2), and from these drawings, it can be seen that spherical porous silica particles having sufficiently expanded pores were formed evenly.

Figure 30:
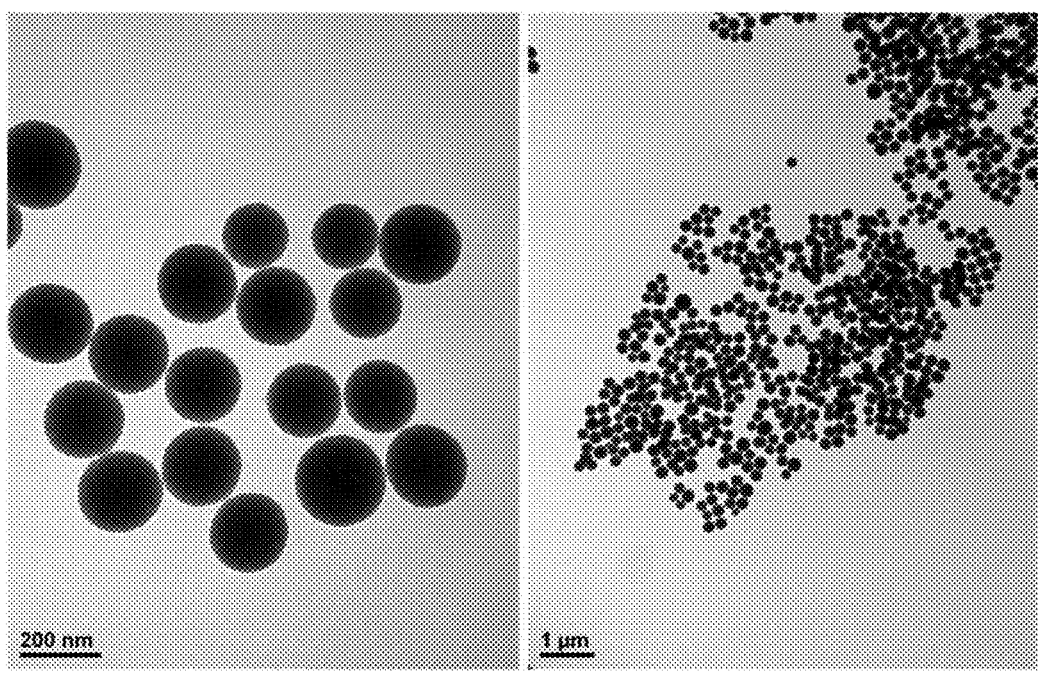
FIG. 30 is micrographs of small pore particles obtained in a manufacturing process of the porous silica particles according to one embodiment of the present invention.
Figure 31:
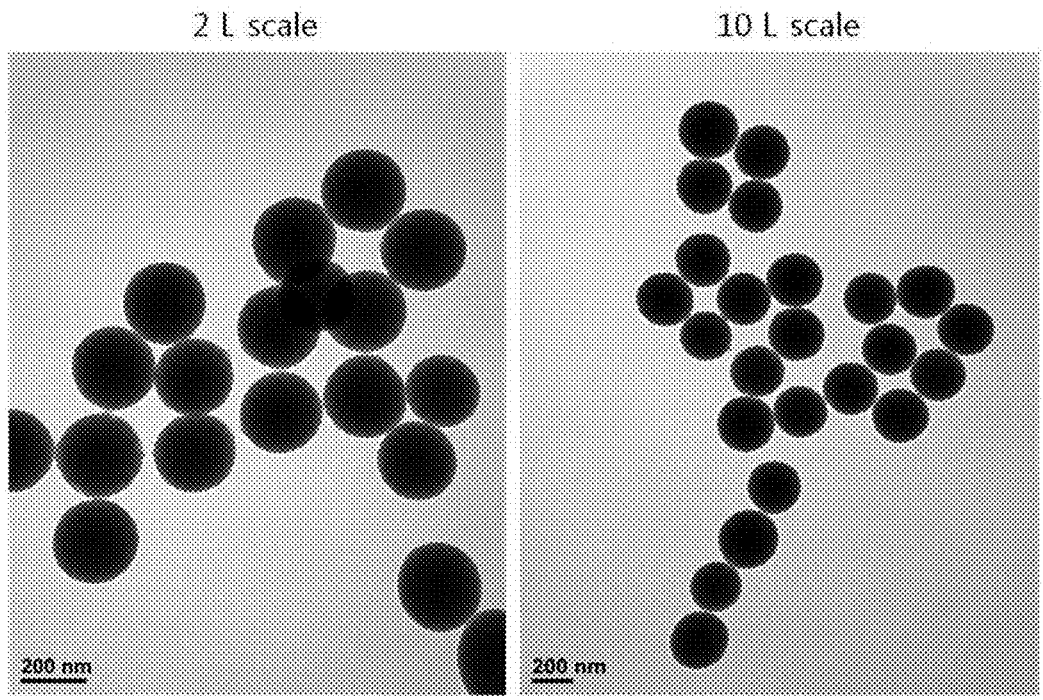
FIG. 31 is micrographs of the small pore particles according to one embodiment of the present invention.

FIG. 30 is photographs of the small pore particles in Experimental Example 9-1-(1), FIG. 31 is comparative photographs of the small pore particles in Experimental Examples 9-1-(1) and 9-1-(3), and from these drawings, it can be seen that spherical small pore particles were formed evenly.

2-2. Calculation of BET Surface Area and Pore Volume

Surface areas and pore volumes of the small pore particles in Experimental Example 9-1-(1) and the porous silica particles of Experimental Examples 9-1-(1), (7), (8) and (10) were calculated. The surface areas were calculated by Brunauer-Emmett-Teller (BET) method, and the pore size distributions were calculated by Barrett-Joyner-Halenda (BJH) method.

Figure 32:
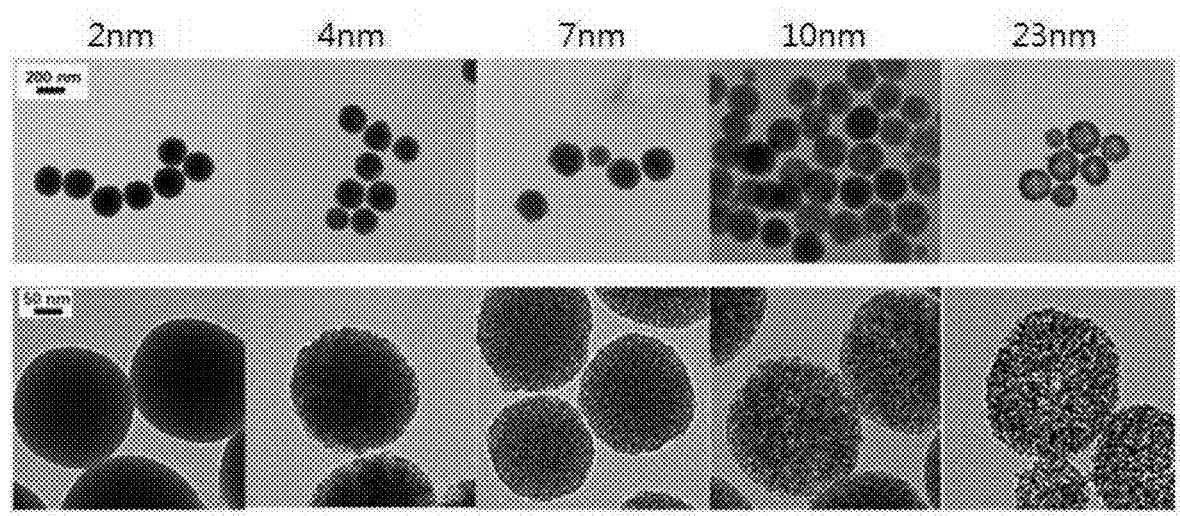
FIG. 32 is micrographs of the porous silica particles for each pore diameter according to one embodiment of the present invention.

Micrographs of the respective particles are shown in FIG. 32, and the calculation results are shown in Table 4 below.

TABLE 4

| Section | Pore diameter (nm) | BET surface area (m$^2$/g) | Pore volume (mL/g) |
|---|---|---|---|
| Small pore particle in Example 9-1-(1) | 2.1 | 1337 | 0.69 |
| Example 9-1-(7) | 4.3 | 630 | 0.72 |
| Example 9-1-(8) | 6.9 | 521 | 0.79 |
| Example 9-1-(1) | 10.4 | 486 | 0.82 |
| Example 9-1-(10) | 23 | 395 | 0.97 |

2-3. Identification of Biodegradability

In order to identify biodegradability of the porous silica particles in Experimental Example 9-1-(1), biodegradability at 37° C. in SBF (pH 7.4) was observed under a microscope at 0 hours, 120 hours and 360 hours, and results thereof are shown in FIG. 33.

Referring to FIG. 33, it can be seen that the porous silica particles are biodegraded and almost degraded after 360 hours.

2-4. Measurement of Absorbance Ratio

Absorbance ratio over time was measured according to Equation 1 below.

$$A_t/A_0 \quad \text{[Equation 1]}$$

wherein $A_0$ is absorbance of the porous silica particles measured by putting 5 ml of suspension containing 1 mg/ml of the porous silica particles into a cylindrical permeable membrane having pores with a pore diameter of 50 kDa, 15 ml of the same solvent as the suspension comes into contact with an outside of the permeable membrane, and the inside/outside of the permeable membrane are horizontally stirred at 60 rpm and 37° C., and $A_t$ indicates absorbance of the porous silica particles measured after lapse of "t" hours since $A_o$ was measured.

Specifically, 5 mg of porous silica particle powder was dissolved in 5 ml of SBF (pH 7.4). Thereafter, 5 ml of porous silica particle solution was placed in a permeable membrane having pores with a pore diameter of 50 kDa shown in FIG. 34. 15 ml of SBF was added to the outer membrane, and the SBF on the outer membrane was replaced every 12 hours. Degradation of the porous silica particles was performed at 37° C. under horizontal stirring at 60 rpm.

Then, the absorbance was measured by UV-vis spectroscopy and analyzed at λ=640 nm.

(1) Measurement of Absorbance Ratio

The absorbance ratio of the porous silica particles in Experimental Example 9-1-(1) was measured according to the above method, and results thereof are shown in FIG. 35.

Referring to FIG. 35, it can be seen that t, at which the absorbance ratio becomes 1/2, is about 58 hours to demonstrate very slow degradation.

(2) Particle Size

Absorbances of the porous silica particles in Experimental Examples 9-1-(1), (5), and (6) were measured according to Equation 1 above, and results thereof are shown in FIG. 36 (SBF used as the suspension and the solvent).

Referring to FIG. 36, it can be seen that t is decreased as the particle size is increased.

(3) Average Pore Diameter

Absorbances of the porous silica particles in Experimental Examples 9-1-(1) and (9) and the microporous silica particles in Experimental Example 9-1-(1) as a control were measured according to Equation 1 above, and results thereof are shown in FIG. 37 (SBF used as the suspension and the solvent).

Referring to FIG. 37, it can be seen that the porous silica particles of the inventive example have a significantly larger t than the control.

(4) pH

Absorbance of the porous silica particles in Experimental Example 9-1-(4) for each pH was measured. The absorbance was measured in SBF and in Tris at pH 2, 5, and 7.4, and results thereof are shown in FIG. 38.

Referring to FIG. 38, it could be seen that, although there is a difference in t in relation to pH, t at which all absorbance ratio becomes 1/2 was 24 or more.

(5) Charging

Absorbance of the porous silica particles in Experimental Example 9-2-(1)-1) was measured, and results thereof are shown in FIG. 39 (Tris (pH 7.4) used as the suspension and the solvent).

Referring to FIG. 39, it could be seen that t at which the absorbance ratio of the positively charged particles becomes 1/2 was 24 or more.

2-5. Release of Supported Nucleic Acid Molecules

10 µl of porous silica particles loaded with Cy5-siRNA were resuspended in SBF (pH 7.4, 37° C.) and put into a permeable membrane with a pore diameter of 20 kDa (a tube in FIG. 40).

Thereafter, the permeation tube was immersed in 1.5 ml of SBF.

Release of siRNA was performed at 37° C. under 60 rpm horizontal stirring.

Before 24 hours, the discharged solvent was recovered at 0.5, 1, 2, 4, 8, 12, and 24 hours lapse, and thereafter, 0.5 ml of the discharged solvent was recovered at 24 hours interval for fluorescence measurement, followed by adding equal amount of SBF.

Fluorescence intensity of Cy5-siRNA was measured at 670 nm wavelength ($\lambda_{ex}$=647 nm) to determine a degree of emission of siRNA, and results thereof are shown in FIG. 41.

Referring to FIG. 41, it can be seen that a time of 50% siRNA release is about 48 hours.

3. In Vitro Identification of Effective Induction of CTGF mRNA Knockdown of LEM-S401

Figure 1:
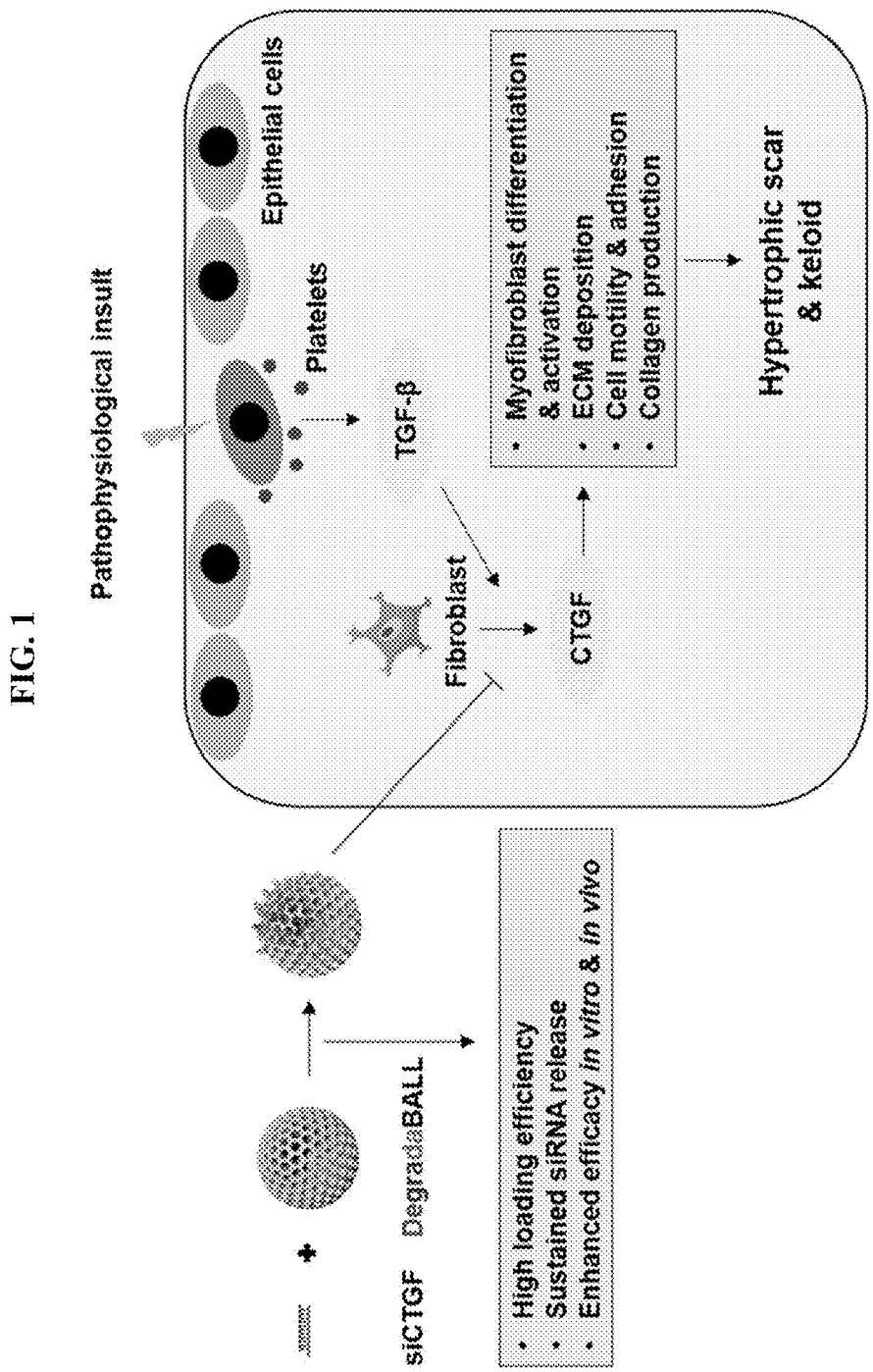
FIG. 1 is a diagram schematically illustrating a cellular mechanism of hypertrophic scars and keloids due to overexpression of CTGF induced through a pathological pathway and a principle for effective inhibition of CTGF expression by LEM-S401.

In order to determine target gene knockdown efficiency of LEM-S401, A549 cell (human lung cancer non-small cell) and HaCaT cell (human keratinocyte cell) were treated with DEGRADABALL (LEM-S401) carrying siCTGF. Because both cell-lines have functionally active CTGF transcription pathways, A549 and HaCaT cells are widely used as in vitro model cells in fibrosis studies. First, A549 cells were treated with various concentrations of LEM-S401 (12.5, 25, 50 and 100 nM) and then incubated with 2 ng/ml of TGF-ß in order to induce CTGF expression (FIG. 1). Previous studies have shown that TGF-ß induces CTGF expression in vitro, and it was identified that CTGF expression was significantly increased by treating A549 and HaCaT cells with TGF-ß

Figure 2:
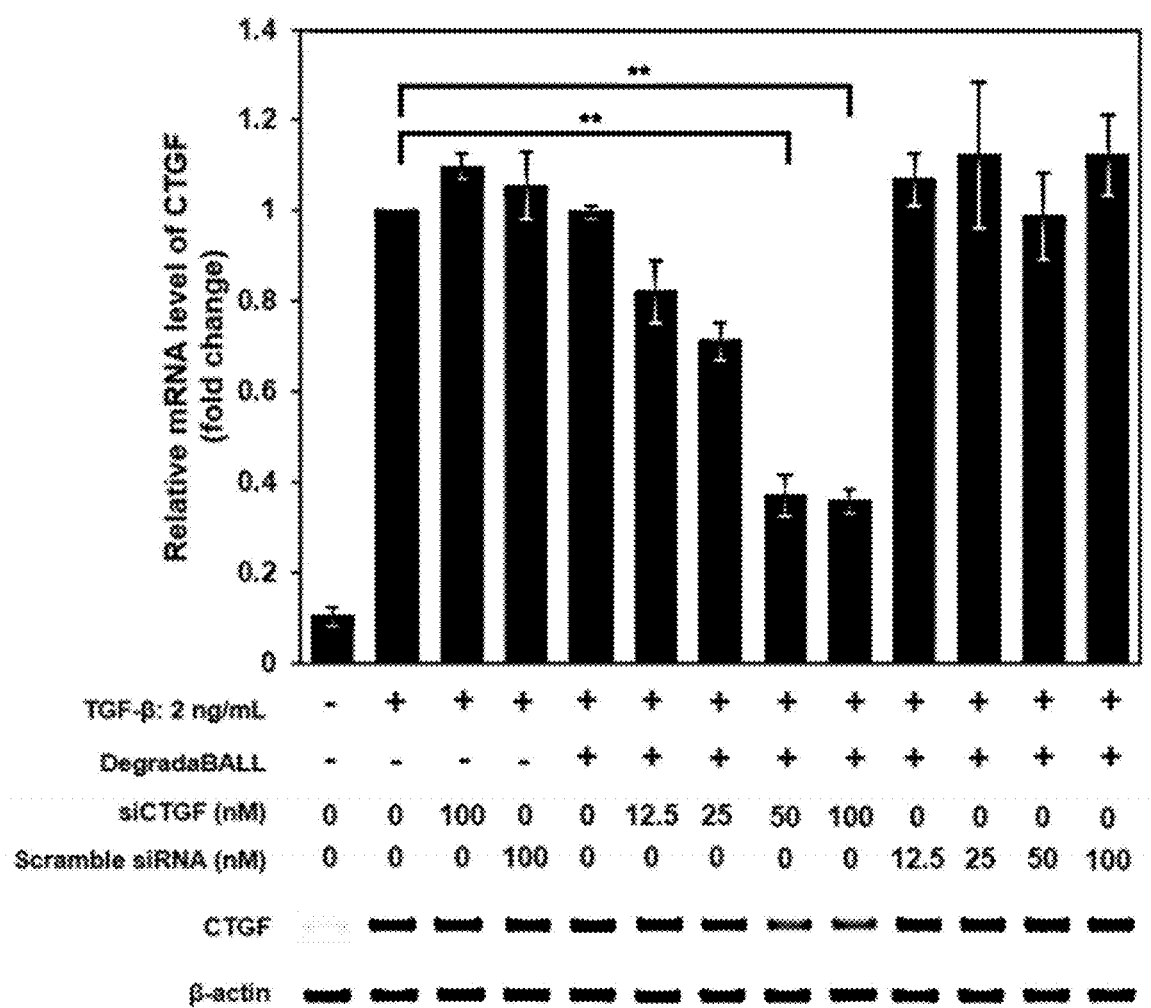
FIGS. 2 and 3 are graphs illustrating induction of CTGF expression by 12 ng/ml of TGF-β after treating A549 (FIG. 2) and HaCaT (FIG. 3) cells, respectively, with different doses of LEM-S401 (12.5, 25, 50, 100 nM) for 6 hours, as well as comparison of CTGF mRNA expression levels with the control (untreated, siCTGF only, DEGRADABALL only, and scrambled siRNA treatments) using RT-PCR (* $P<0.05$,  $P<0.01$, * $P<0.005$).
Figure 3:
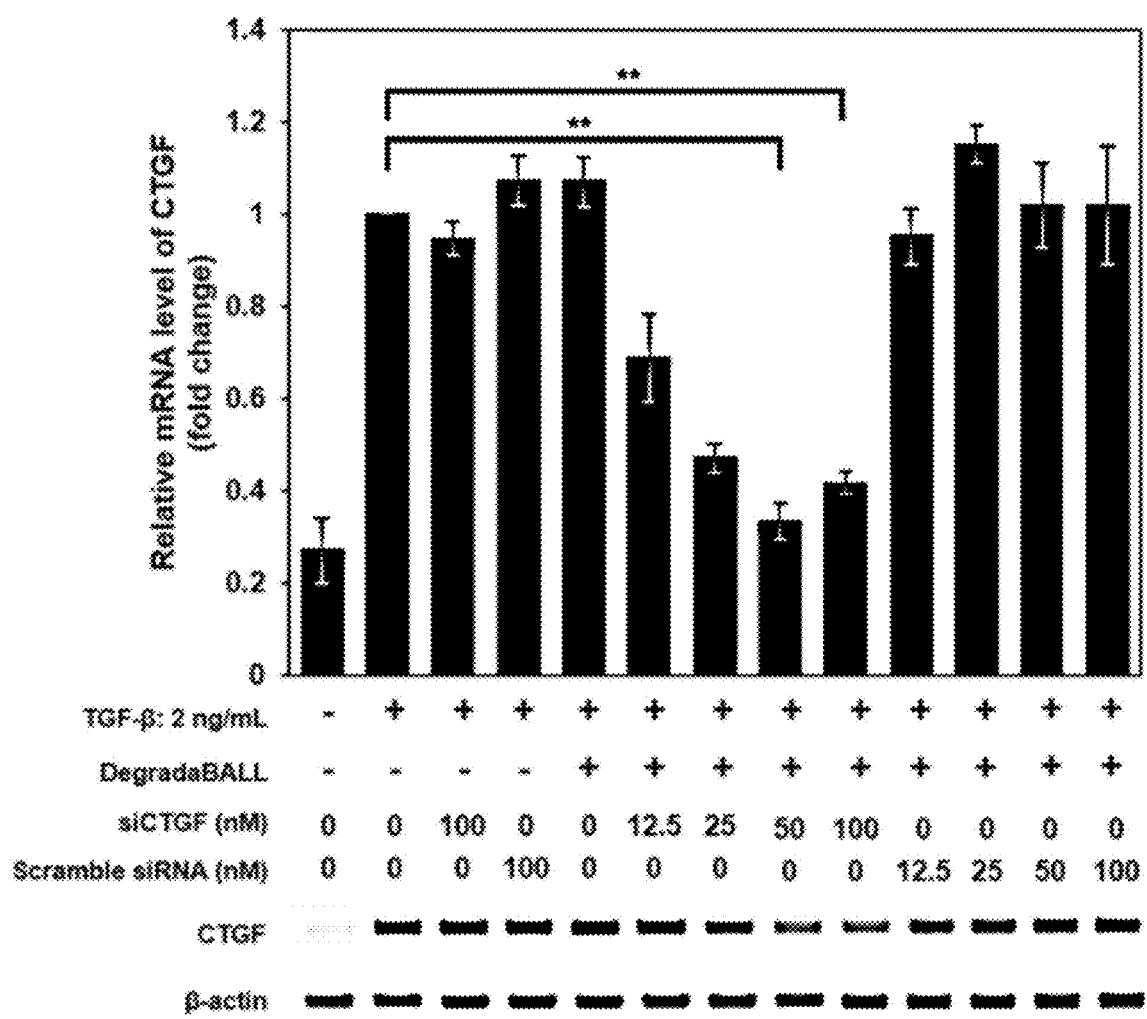

(FIGS. 17A and 17B). Treatment of LEM-S401 on cell-lines reduced mRNA expression levels of CTGF in a concentration dependent manner. On the other hand, the control (siCTGF only, scrambled siRNA and vehicle (DEGRADABALL) only) did not show significant differences in mRNA level of CTGF in both A549 and HaCaT cells (FIGS. 2 and 3). These results indicate that LEM-S401 efficiently transfected siCTGF into cells and induced knockdown of CTGF gene.

4. In Vitro Sustained siCTGF Release of LEM-S401

Figure 4:
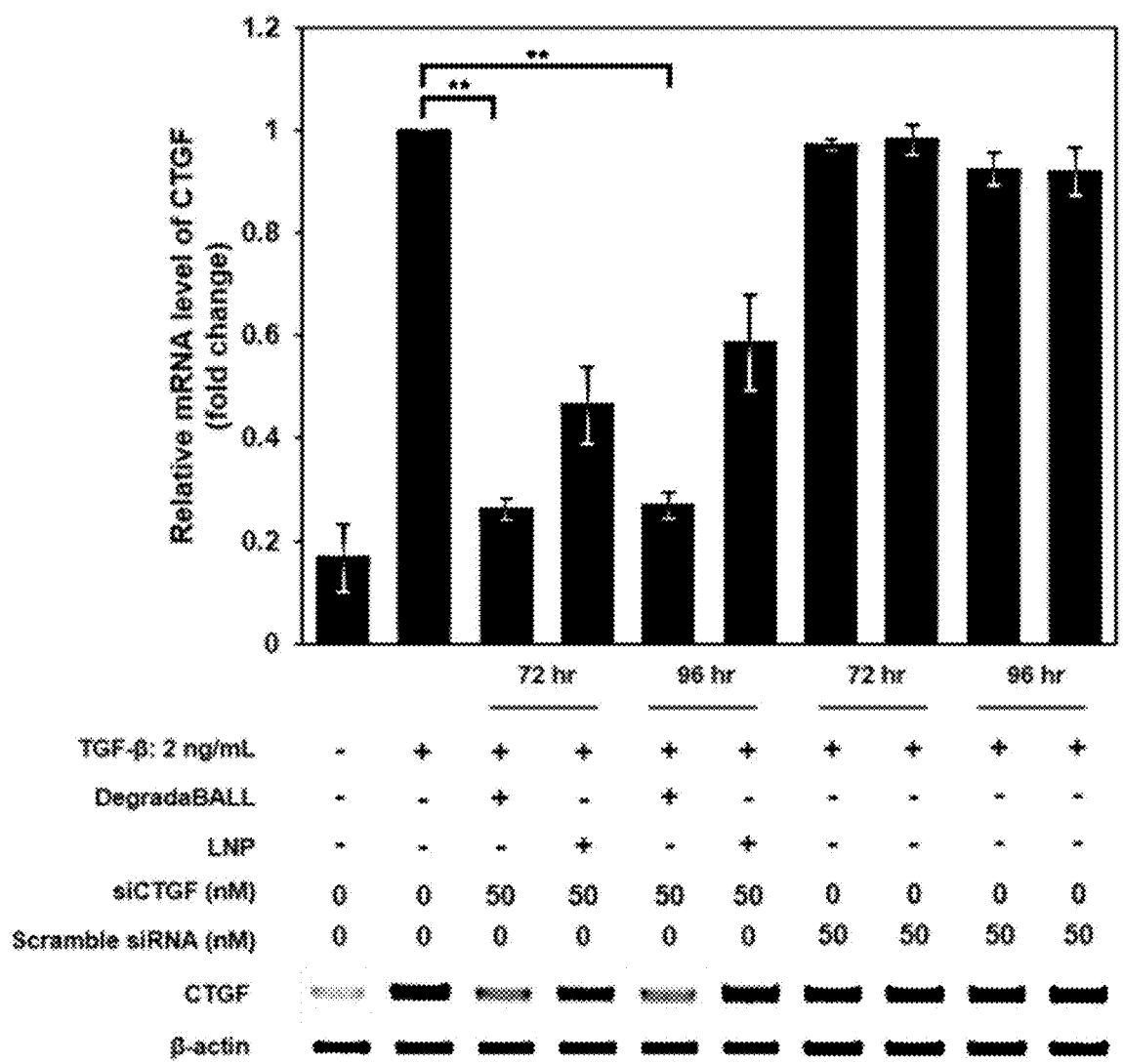
FIGS. 4 and 5 are graphs illustrating comparison of A549 (FIG. 4) and HaCaT (FIG. 5) cells after treating these cells with lipid nanoparticles (LNPs) carrying LEM-S401 and siCTGF, respectively, wherein the cells were incubated for 72 and 96 hours, followed by treatment thereof using TGF-β, 12 hours before harvesting the cells (* $P<0.05$,  $P<0.01$, * $P<0.005$).
Figure 5:
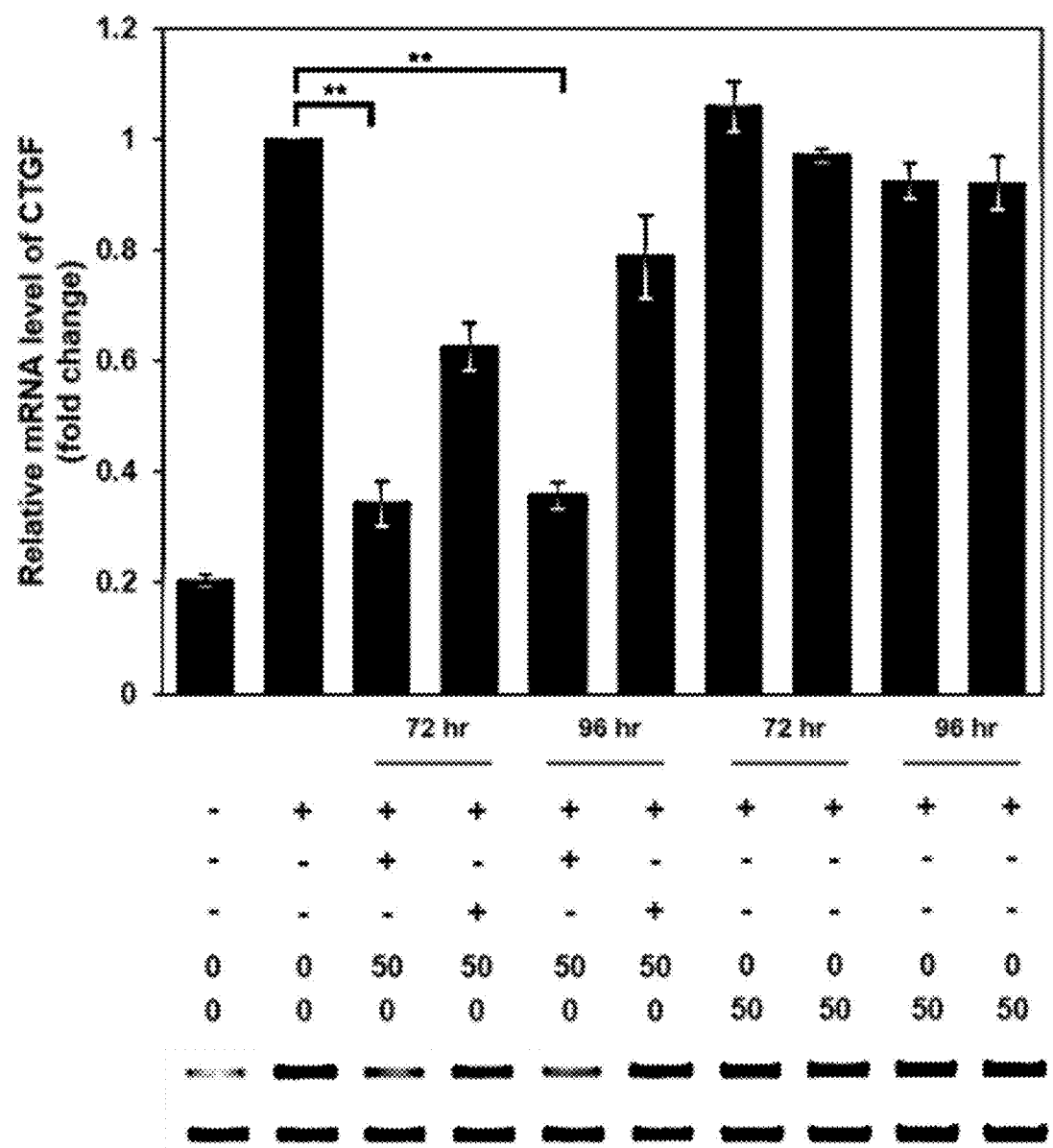

In the present experiment, LEM-S401 maintained a longer CTGF knockdown effect than LNP in A549 and HaCaT cells. A549 and HaCaT cells were treated with siCTGF supported on LEM-S401 (50 nM) and LNP (50 nM), respectively, followed by inducing CTGF expression through TGF-ß treatment. Downregulation of CTGF in A549 cells lasted up to 96 hours after LEM-S401 treatment (CTGF expression level, 72 hours: 26.3%, 96 hours: 26.9%). However, the knockdown efficiency of siCTGF supported on LNP was not high at both 72 and 96 hours (CTGF expression level. 72 hours: 46.4%, 96 hours: 58.6%). In addition, knockdown efficiency of LEM-S401 in HaCaT cells (CTGF expression level, 72 hours: 34.3%, 96 hours: 35.8%) was determined to be more consistent and superior over siCTGF supported on LNP (CTGF expression level, 72 hours: 62.5%, 96 hours: 78.8%) (FIGS. 4, 5). Taken together, it can be seen that LEM-S401 inhibits the target mRNA expression level in cells for a longer time period than siCTGF supported on LNP.

5. Identification of CTGF Expression and Hypertrophy Scar Formation Inhibitory Ability of LEM-S401 in Mouse Skin Wound Model Next, experiments were conducted to determine if LEM-S401 could downregulate CTGF expression in vivo. Prior to measuring gene knockdown efficacy in vivo. C57BL/6 mice were injected with fluorescent label LEM-S401 consisting of FITC-conjugated siCTGF supported on TAMRA-conjugated DEGRADABALL.

Figure 6B:
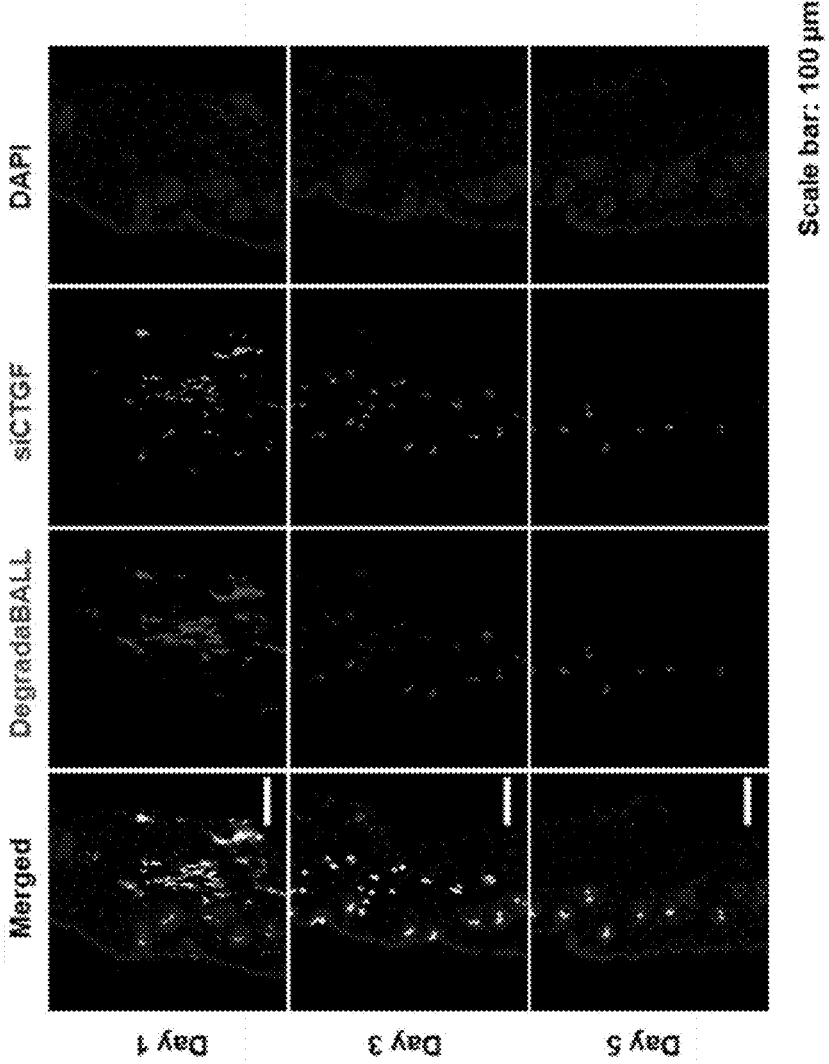
FIGS. 6A and 6B illustrate fluorescence images of the excised mouse skin taken at different time points (day 1, 3, 5) to measure skin retention time of siCTGF and DEGRADABALL at LEM-S401 injection site (left, Scale bar: 25 mm) after subcutaneous injection of LEM-S401 into the mouse skin; and fluorescence images of the skin section treated by the same method as described above after DAPI staining (right, Scale bar: 100 μm).
Figure 6A:
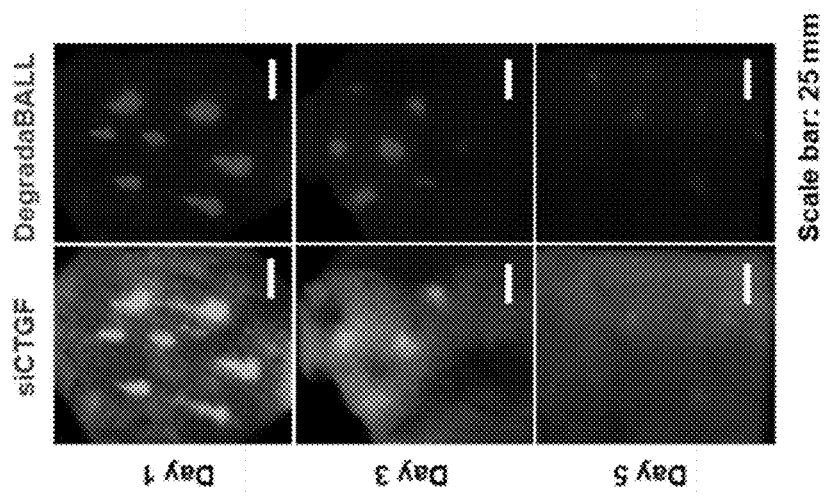
Figure 7B:
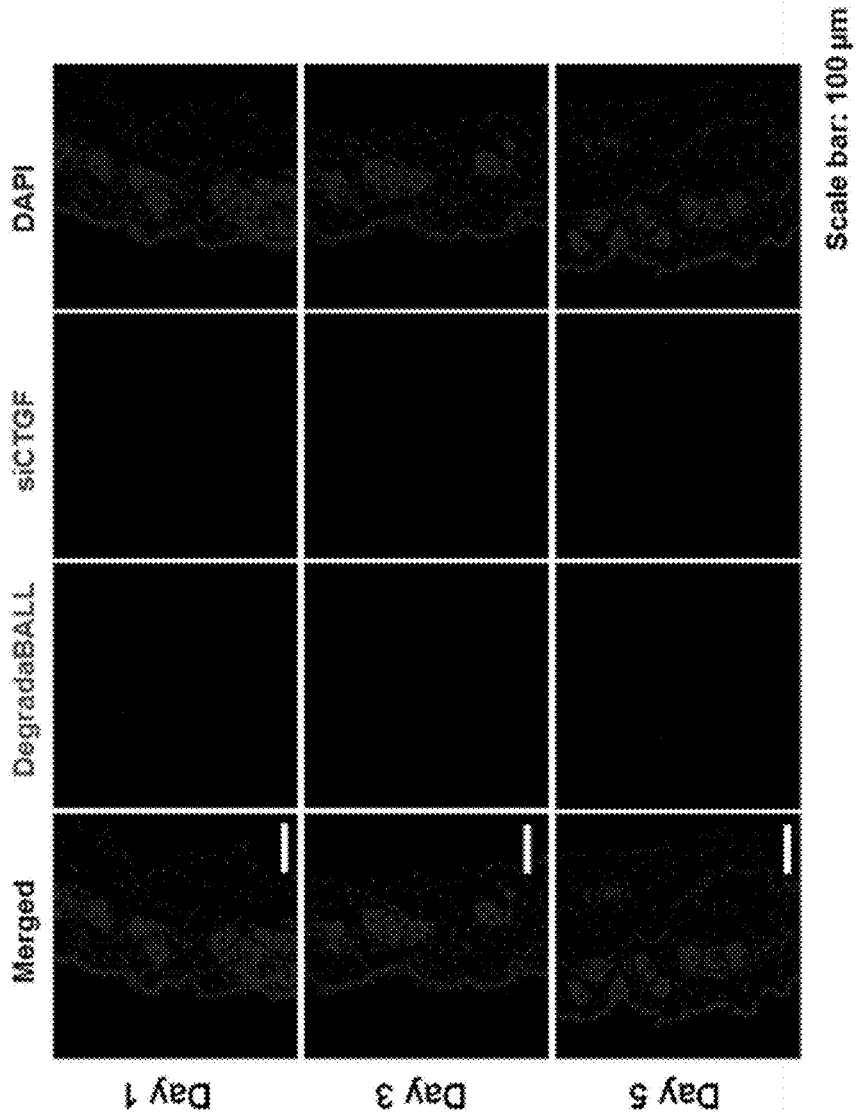
FIGS. 7A and 7B illustrate fluorescence images of resected skin subcutaneously injected with FITC-conjugated siCTGF unsupported in DEGRADABALL, which were taken at different time points (left); and fluorescence images of the skin section treated by the same method as described above after DAPI staining (Scale bar: 100 μm).
Figure 7A:
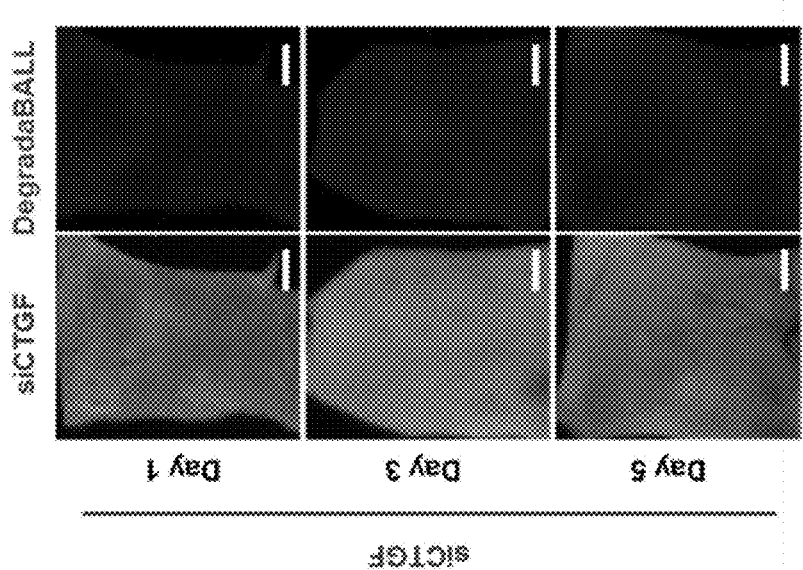
Figure 8:
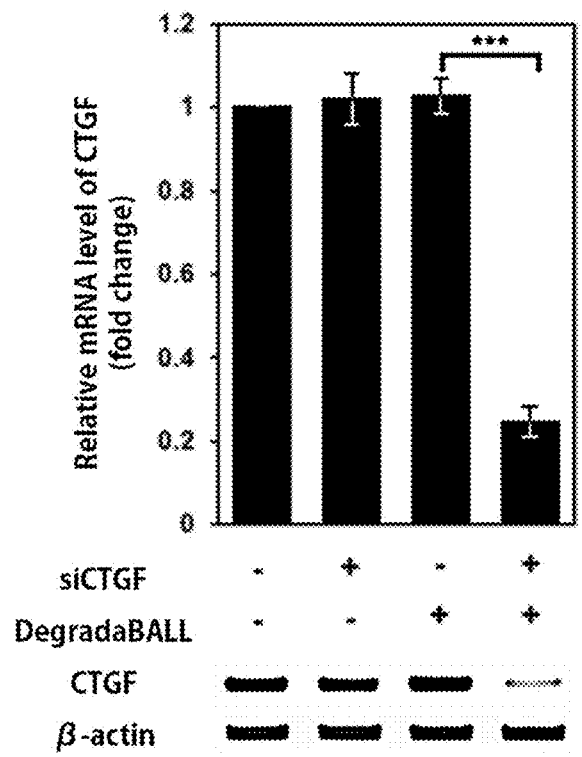
FIGS. 8 to 15 are diagrams illustrating results of subcutaneous injection of LEM-S401 (1 nmol) around mouse skin wound on day 0, 4, 8, 12, specifically.
Figure 9:
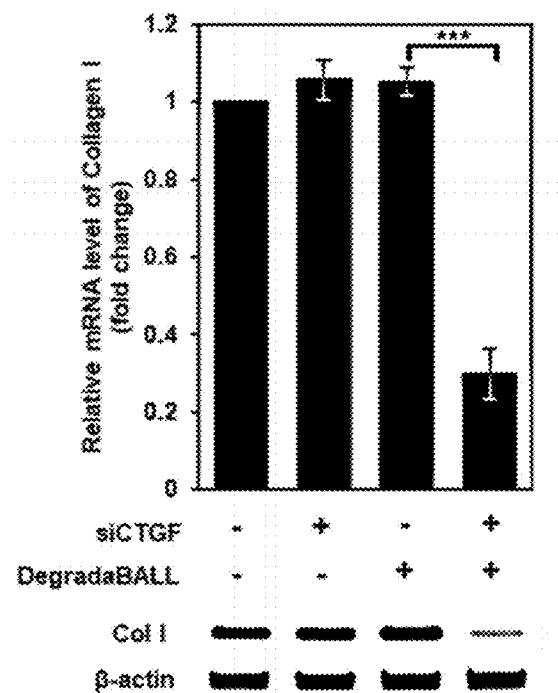
Figure 10:
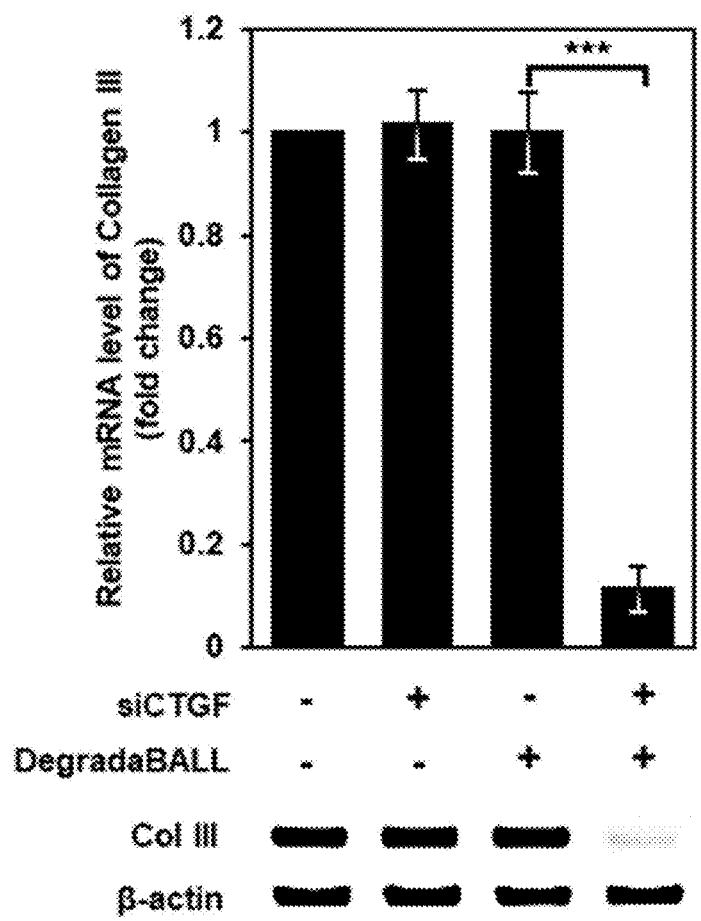

On the other hand, only unsupported (free) FITC-conjugated siCTGF was injected into the mice through a subcutaneous injection route. Then, it was attempted to compare durations of both LEM-S401 and free siCTGF at the injection sites. Therefore, fluorescent images of resected mouse skin and sectioned skin were analyzed on day 1, 3 and 5 after the injection. TAMRA-DEGRADABALL carrying FITC-siCTGF showed strong fluorescent emission at the injection site on day 1. Further, the fluorescence was gradually decreased over time, but was maintained at the injection site until S days after the injection (FIGS. 6A and 6B). A tendency of decreasing fluorescence at the injection site over time has followed a skin section sliding tendency (FIGS. 6A and 6B). On the other hand, no fluorescence signal was observed in the excised skin or fragmented skin slides from mice injected with only unsupported free FITC-siCTGF, suggesting that the free siCTGF is rapidly dispersed in the body or degraded into small fragments, which in turn induce very rapid diffusion (FIGS. 7A and 7B). The above data demonstrated that LEM-S401 can maintain significantly higher concentration of siCTGF than free siCTGF in the skin, specifically, up to at least day 3 after the injection. Next, it was demonstrated in the mouse skin wound model that LEM-S401 could induce CTGF gene knockdown, and reduce collagen overproduction. After forming a wound hole by a biopsy punch in the rat's back skin (day 0), silicone splints were sutured around the wound for management and observation. LEM-S401 was injected subcutaneously around the wound at days 0, 4, 8 and 12. The mouse was sacrificed on day 16, and CTGF expression level in the skin was analyzed by RT-PCR. The CTGF expression level was significantly decreased in the LEM-S401 treated group, whereas no change was observed in the group treated with siCTGF or DEGRADABALL alone. In addition, collagen types 1 and 3 expression levels were also significantly downregulated in the LEM-S401 treated group (FIGS. 8 to 10). Collagen types 1 and 3 known to be induced by CTGF are the major components of hypertrophic scars and keloids. Therefore, it can be assured that CTGF with expression inhibited by LEM-S401 has influenced the expression level of collagen types 1 and 3.

Figure 11:
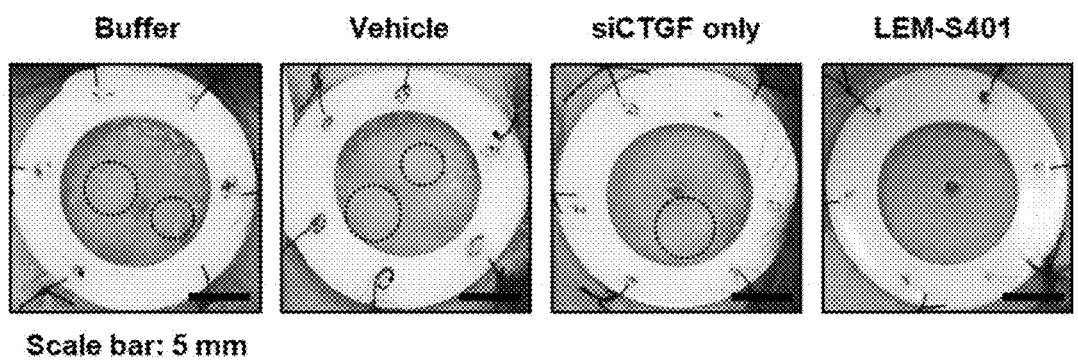
Figure 12:
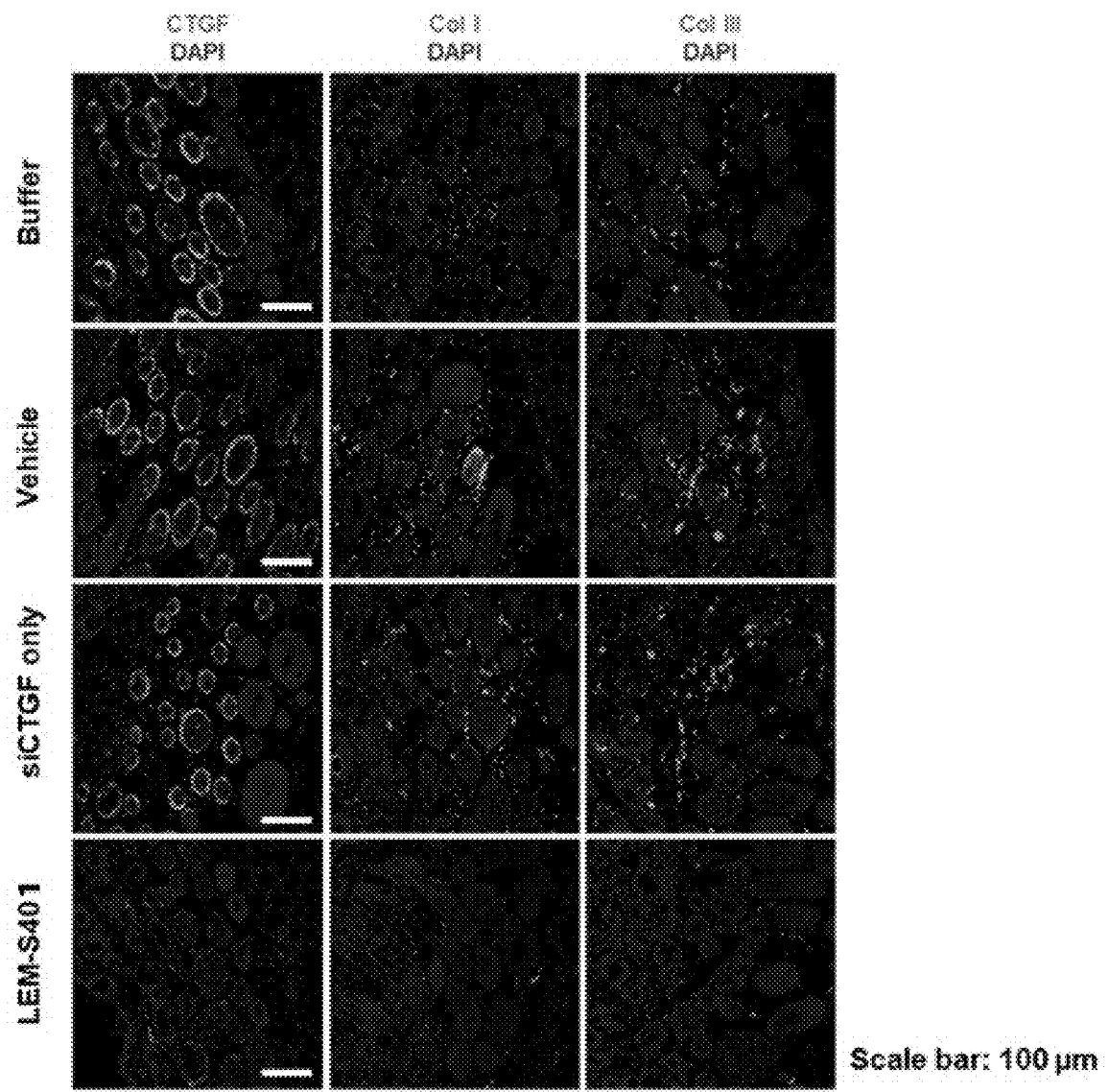
Figure 13:
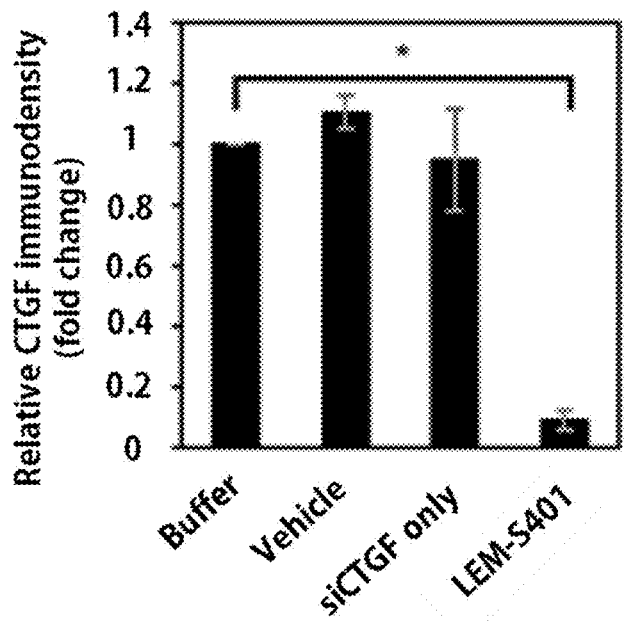
Figure 14:
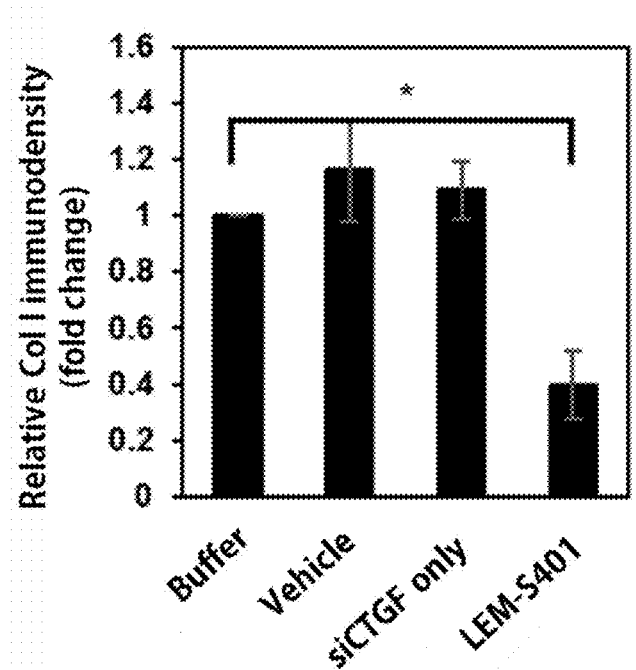
Figure 15:
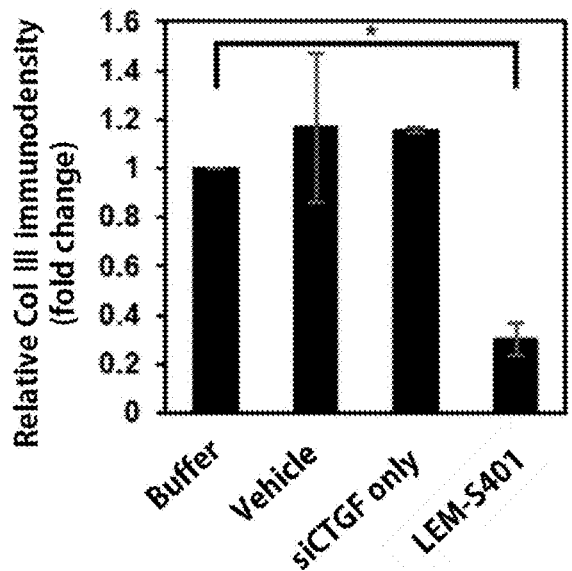
Figure 16:
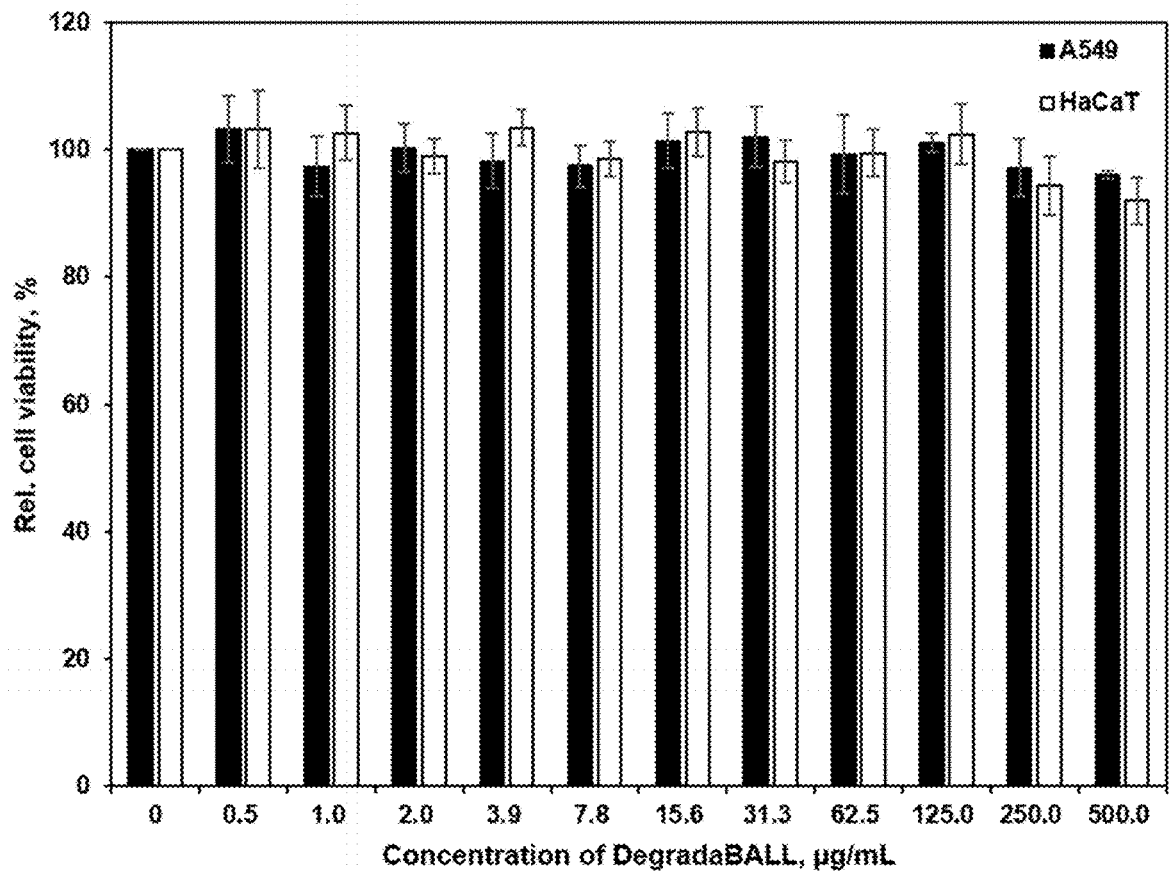
FIG. 16 is a graph illustrating measured results of toxicity in A549 and HaCaT cells by CCK-8 analysis as the concentration of DEGRADABALL is increased.
Figure 18:
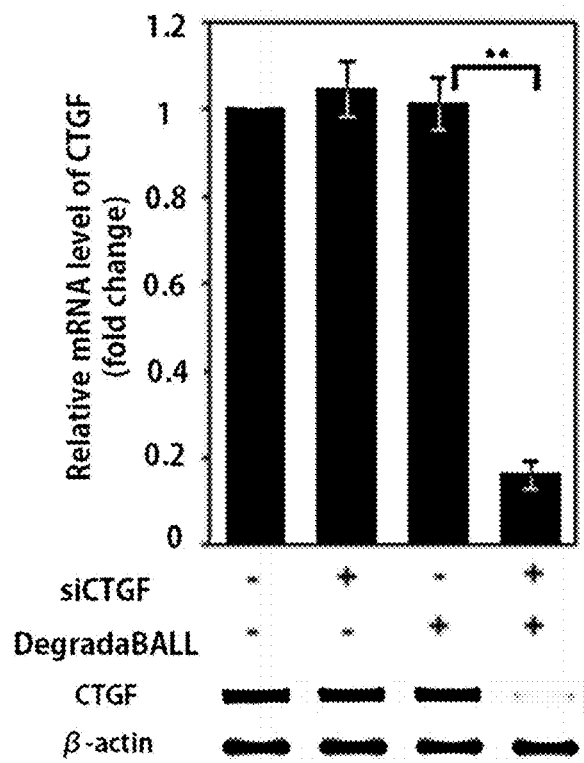
FIGS. 18 to 24 are diagrams illustrating results of subcutaneous injection of LEM-S401 into the wound site, 10, 14, 18 and 22 days after the wound formation, specifically.
Figure 19:
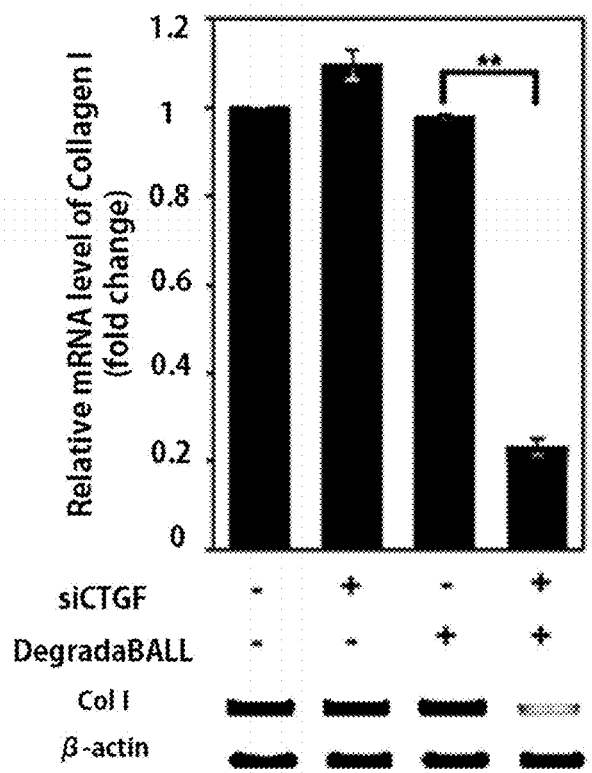
Figure 20:
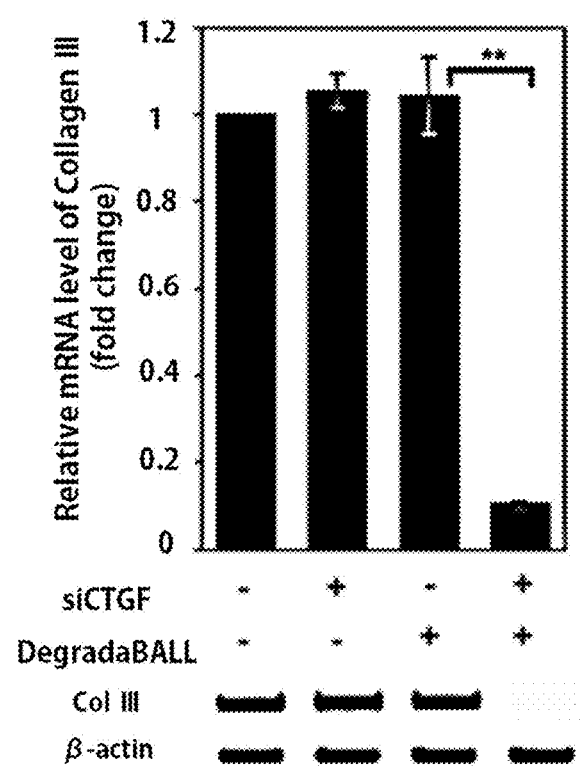
Figure 21:
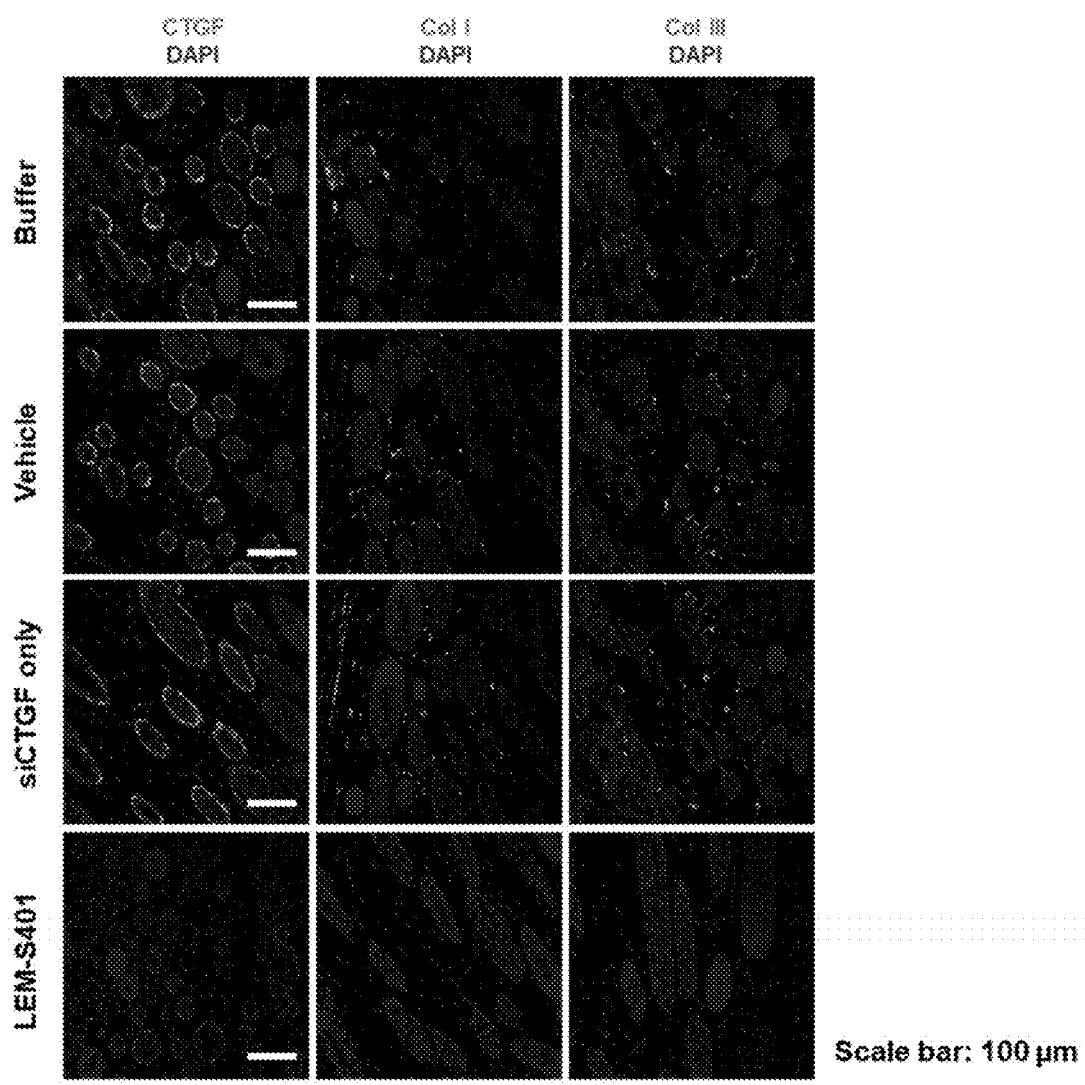
Figure 22:
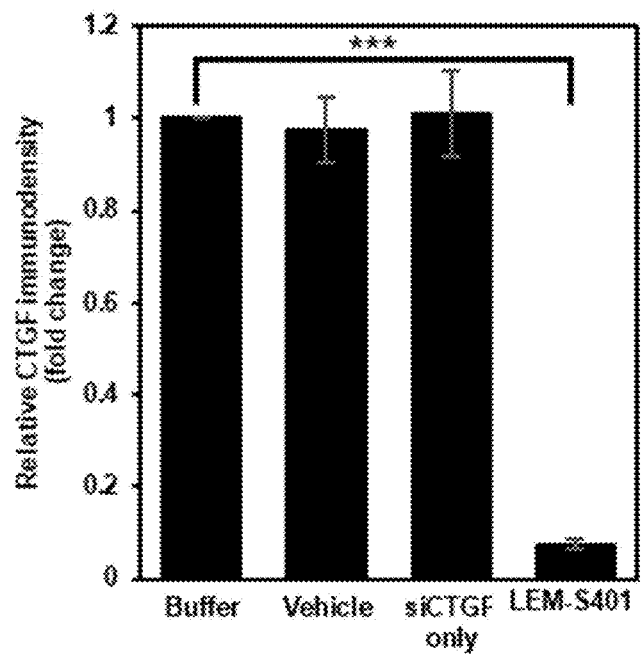
Figure 23:
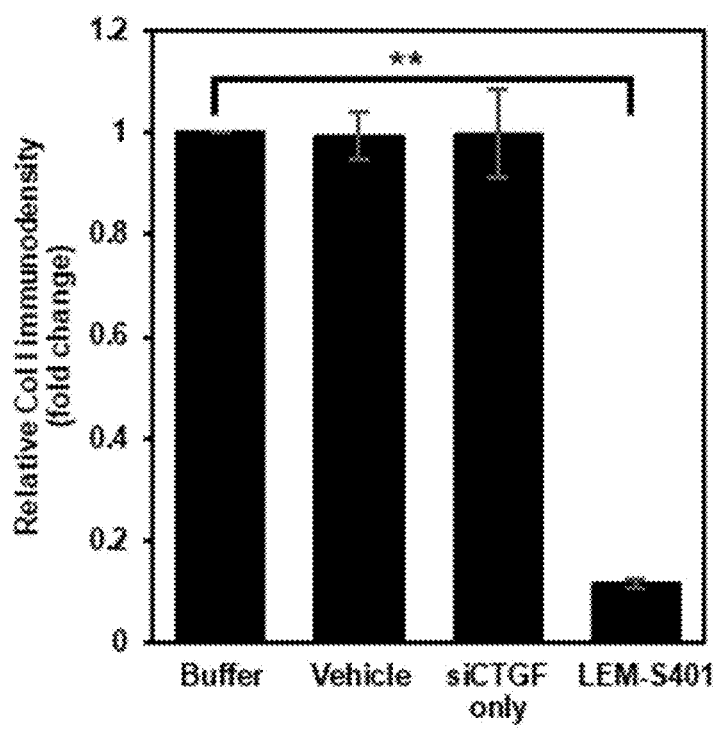
Figure 24:
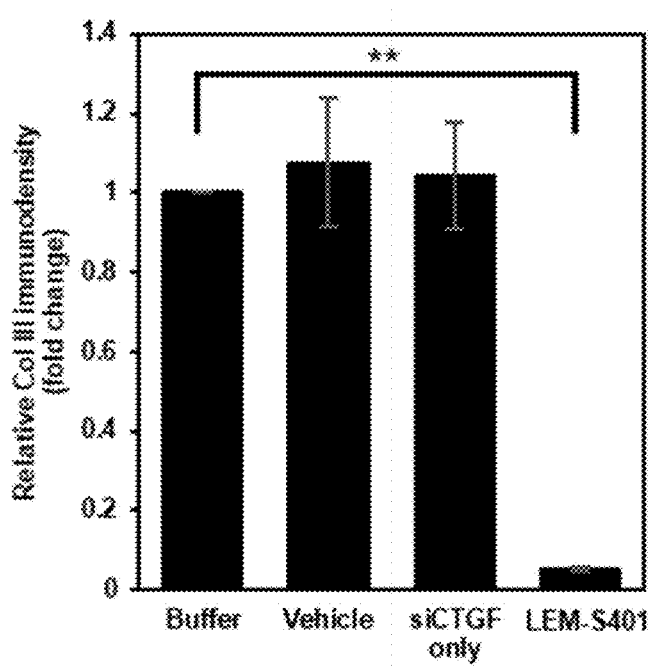
Figure 25:
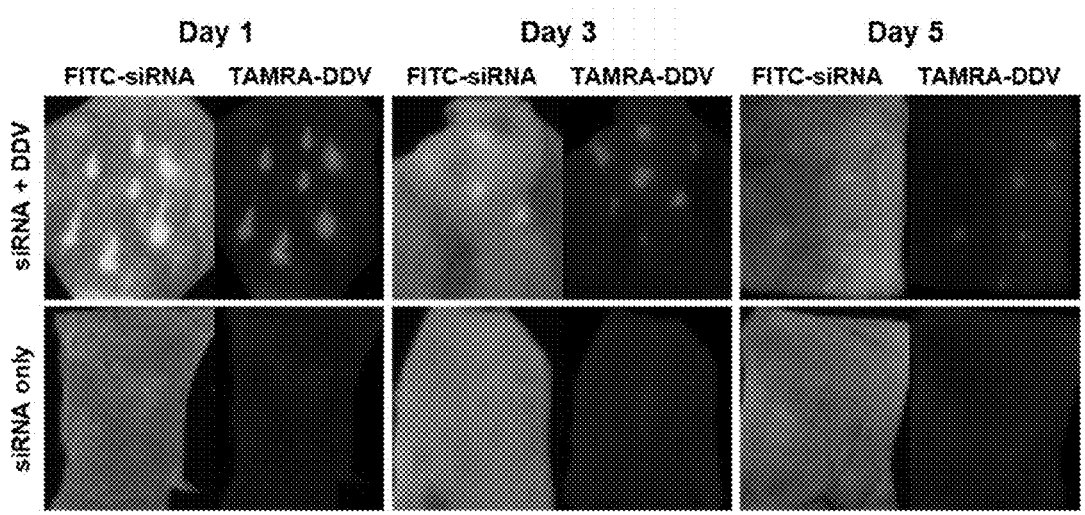
FIG. 25 illustrates detection and comparison results of fluorescent images in vivo between subcutaneous injection of siRNA supported in DDV (porous silica particles, DEGRADABALL) into a mouse and subcutaneous injection of free-siRNA into a mouse.
Figure 26A:
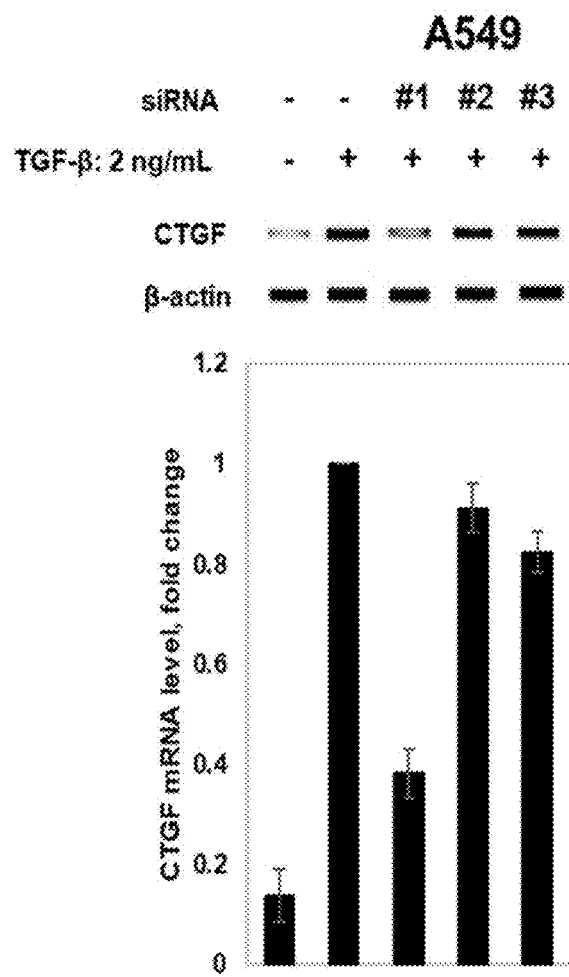
Figure 26B:
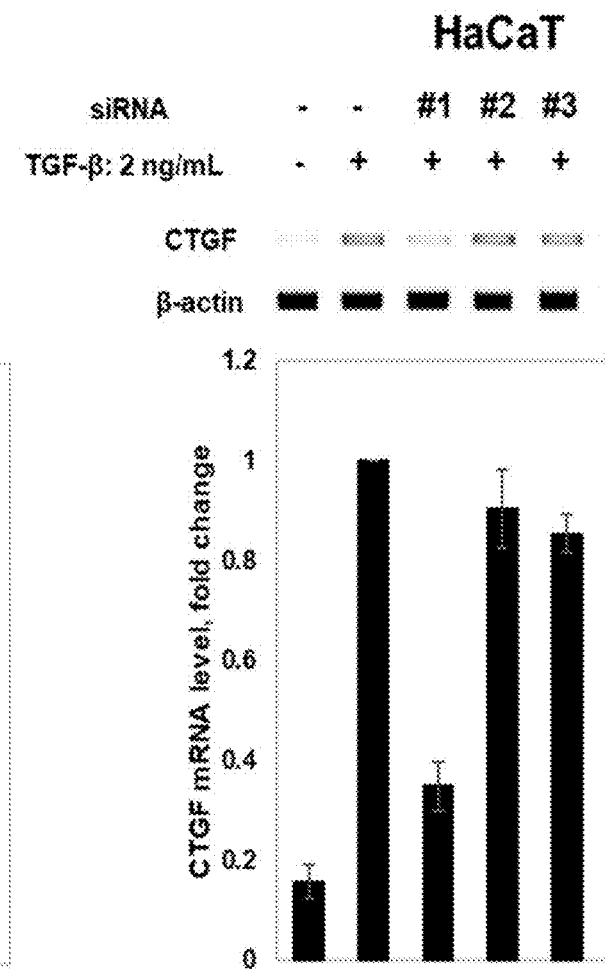
Figure 27A:
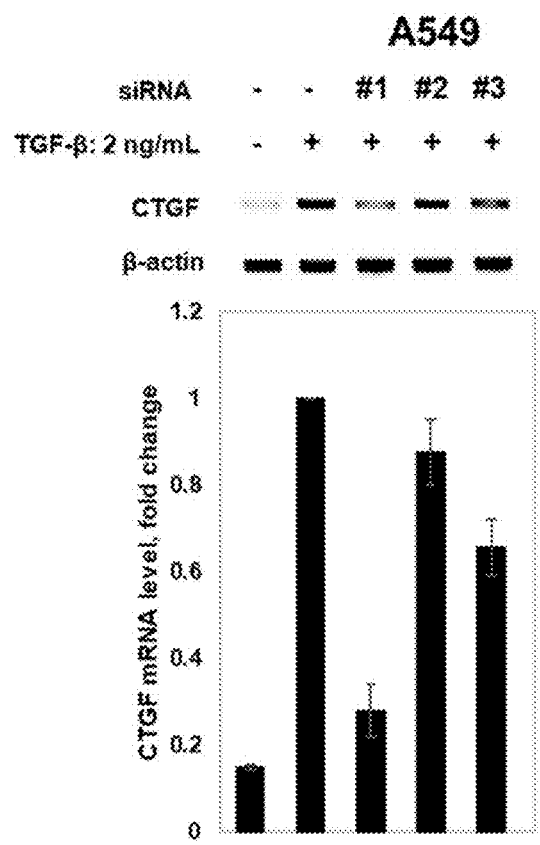
Figure 27B:
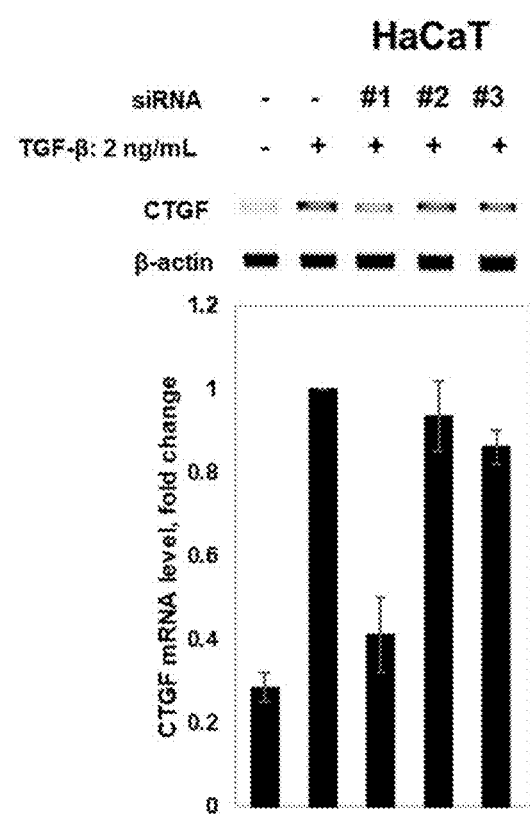

Uneven, bumpy and irregular skin surfaces caused by overgrowth of wound connective tissues are major features of hypertrophic scars and keloids. Wounded skin pictures on day 10 showed irregular features in the control, but skin pictures of the LEM-S401 treated group appeared regular and smooth (FIG. 11). These results demonstrate that LEM-S401 suppresses uncontrolled and uneven skin formation and prevents hypertrophic scar formation. Immunohistochemical analysis results also showed that the expressions of CTGF and collagen types 1 and 3 were significantly lower in the LEM-S401 treated group than the control (FIGS. 12 to 15). In a process of healing skin wounds, tissue remodeling occurs in the dermis after the recovery of epidermis. In this process, the expression of collagen fibers is increased, which in turn may lead to hypertrophic scars or keloids if collagen formation is uncontrollable. Therefore, in order to identify whether LEM-S401 can suppress the expression of CTGF and collagen during tissue remodeling. LEM-S401 was injected after the epidermis was recovered. Specifically, a biopsy punch was used to puncture the mouse skin (day 0), and on 10, 14, 18 and 22 days after the epidermis is completely healed, LEM-S401 was injected into the wound site. Typically, in the mouse wound model, 10 days was sufficient to completely heal the epidermis after the wound formation. After sacrifice on day 26, expression levels of CTGF and collagen types 1 and 3 were analyzed by RT-PCR. The expression levels of CTGF and collagen in the LEM-$401 treated group were significantly lower than those in the control (FIGS. 18 to 20). Immunohistochemical analysis results showed that CTGF and collagen types 1 and 3 protein expression levels were significantly reduced in the LEM-S401 treated group (FIGS. 21 to 24).

What is claimed is:

1. A composition comprising: a nucleic acid molecule comprising at least one selected from the group consisting of:
   (i) siRNA comprised of a sense RNA having the sequence of SEQ ID NO: 1 and an antisense RNA having the sequence of SEQ ID NO: 2; (ii) dsRNA comprised of a strand having a sequence of SEQ ID NO: 3 and another strand complementary thereto; (iii) dsRNA comprised of a strand having a sequence of SEQ ID NO: 57 and another strand complementary thereto; (iv) dsRNA comprised of a strand having a sequence of SEQ ID NO: 60 and another strand complementary thereto; and
   a porous silica particle,
   wherein the nucleic acid molecule is loaded on a surface or inside the pores of the porous silica particle; and
   the porous silica particle is characterized in that an average pore diameter ranges from 5 to 100 nm, and t, at which an absorbance ratio in the following Equation 1 becomes 1/2, is 24 or more:

$$A_t/A_o \quad \text{[Equation 1]}$$

wherein Ao is absorbance of the porous silica particle measured by putting 5 ml of suspension containing 1 mg/ml of porous silica particle into a cylindrical permeable membrane having pores with a pore diameter of 50 kDa:
   15 ml of the same solvent as the suspension comes into contact with an outside of the permeable membrane, and the inside/outside of the permeable membrane are horizontally stirred at 60 rpm and at 37° C.;
   pH of the suspension is 7.4; and
   $A_t$ indicates absorbance of the porous silica particle measured after lapse of "t" hours since Ao was measured.

2. The composition of claim 1, wherein the nucleic acid molecule comprises siRNA comprised of a sense RNA having the sequence of SEQ ID NO: 1 and an antisense RNA having the sequence of SEQ ID NO: 2; or dsRNA comprised of a strand having a sequence of SEQ ID NO: 3 and another strand complementary thereto.

3. The composition of claim 1, wherein each of the sense RNA and the antisense RNA further comprises a sequence of UU or dTdT at 3'-terminals of the sense RNA and the antisense RNA sequence.

4. The composition of claim 1, wherein the porous silica particle is positively charged or uncharged at neutral pH on an outer surface thereof or an inside of the pores.

5. The composition of claim 1, wherein the porous silica particle has hydrophilic or hydrophobic functional groups.

6. The composition of claim 1, wherein the nucleic acid molecule is siRNA comprised of a sense RNA having the sequence of SEQ ID NO: 1 and an antisense RNA having the sequence of SEQ ID NO: 2.

7. The composition of claim 1, wherein the nucleic acid molecule is dsRNA comprised of a strand having a sequence of SEQ ID NO: 3 and another strand complementary thereto.

8. The composition of claim 1, wherein the nucleic acid molecule is at least one selected from the group consisting of (i) dsRNA comprised of a strand having a sequence of SEQ ID NO: 57 and another strand complementary thereto, and (ii) dsRNA comprised of a strand having a sequence of SEQ ID NO: 60 and another strand complementary thereto.

9. A method for treating a fibroproliferative disease, the method comprising administering the composition of claim 1 to subject in need thereof.

10. The method of claim 9, wherein the fibroproliferative disease is at least one selected from the group consisting of hypertrophic scar, keloid, pulmonary fibrosis, liver fibrosis, kidney fibrosis, cystic fibrosis, myelofibrosis, post-peritoneal fibrosis, scleroderma, systemic sclerosis, radiation-induced fibrosis, myocardial fibrosis, biliary fibrosis, renal sclerosis, subretinal fibrosis, diabetic retinopathy, Duken's muscular dystrophy, diabetic kidney disease, chronic renal failure, fatty hepatitis, proliferative vitreoretinopathy, musculoskeletal tumor, osteosarcoma, rhabdomyosarcoma, colorectal cancer, pancreatic cancer, sarcoidosis, macular degeneration, vitreoretinopathy, keratitis, pterygium, ophthalmology disease, uterine fibroids, glomerulonephritis, human immuno-deficient viral renal disease, acute respiratory distress syndrome, chronic obstructive pulmonary disease, rheumatoid arthritis, polymyositis and vascular stenosis.

* * * * *

SEQUENCE LISTING

<160> NUMBER OF SEQ ID NOS: 131

<210> SEQ ID NO 1
<211> LENGTH: 18
<212> TYPE: RNA
<213> ORGANISM: Artificial Sequence
<220> FEATURE:
<223> OTHER INFORMATION: siRNA sense strand

```
<400> SEQUENCE: 1
cucauuagac uggaacuu                                                 18

<210> SEQ ID NO 2
<211> LENGTH: 18
<212> TYPE: RNA
<213> ORGANISM: Artificial Sequence
<220> FEATURE:
<223> OTHER INFORMATION: target 1: siRNA antisense strand

<400> SEQUENCE: 2
aaguuccagu cuaaugag                                                 18

<210> SEQ ID NO 3
<211> LENGTH: 27
<212> TYPE: RNA
<213> ORGANISM: Artificial Sequence
<220> FEATURE:
<223> OTHER INFORMATION: target 1: dsRNA

<400> SEQUENCE: 3
cucauuagac uggaacuuuu ucuaaag                                       27

<210> SEQ ID NO 4
<211> LENGTH: 18
<212> TYPE: RNA
<213> ORGANISM: Artificial Sequence
<220> FEATURE:
<223> OTHER INFORMATION: target 2: siRNA sense strand

<400> SEQUENCE: 4
ggaacuugaa cugauuca                                                 18

<210> SEQ ID NO 5
<211> LENGTH: 18
<212> TYPE: RNA
<213> ORGANISM: Artificial Sequence
<220> FEATURE:
<223> OTHER INFORMATION: target 2: siRNA antisense strand

<400> SEQUENCE: 5
ugaaucaguu caaguucc                                                 18

<210> SEQ ID NO 6
<211> LENGTH: 31
<212> TYPE: RNA
<213> ORGANISM: Artificial Sequence
<220> FEATURE:
<223> OTHER INFORMATION: target 2: dsRNA

<400> SEQUENCE: 6
ggaacuugaa cugauucauu ccuuucuaaa g                                  31

<210> SEQ ID NO 7
<211> LENGTH: 20
<212> TYPE: RNA
<213> ORGANISM: Artificial Sequence
<220> FEATURE:
<223> OTHER INFORMATION: siRNA sense strand

<400> SEQUENCE: 7
cugagugacu cuauauagcu                                               20

<210> SEQ ID NO 8
```

```
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 8
agcuauauag agucacucag                                                      20

<210> SEQ ID NO 9
<211> LENGTH: 29
<212> TYPE: RNA
<213> ORGANISM: Artificial Sequence
<220> FEATURE:
<223> OTHER INFORMATION: dsRNA

<400> SEQUENCE: 9
cugagugacu cuauauagcu uuucuaaag                                            29

<210> SEQ ID NO 10
<211> LENGTH: 19
<212> TYPE: RNA
<213> ORGANISM: Artificial Sequence
<220> FEATURE:
<223> OTHER INFORMATION: siRNA sense strand

<400> SEQUENCE: 10
gcaugaagac auaccgagc                                                       19

<210> SEQ ID NO 11
<211> LENGTH: 19
<212> TYPE: RNA
<213> ORGANISM: Artificial Sequence
<220> FEATURE:
<223> OTHER INFORMATION: siRNA antisense strand

<400> SEQUENCE: 11
gcucgguaug ucuucaugc                                                       19

<210> SEQ ID NO 12
<211> LENGTH: 28
<212> TYPE: RNA
<213> ORGANISM: Artificial Sequence
<220> FEATURE:
<223> OTHER INFORMATION: dsRNA

<400> SEQUENCE: 12
gcaugaagac auaccgagcu uucuaaag                                             28

<210> SEQ ID NO 13
<211> LENGTH: 18
<212> TYPE: RNA
<213> ORGANISM: Artificial Sequence
<220> FEATURE:
<223> OTHER INFORMATION: siRNA sense strand

<400> SEQUENCE: 13
auguuugcac cuuucuag                                                        18

<210> SEQ ID NO 14
<211> LENGTH: 18
<212> TYPE: RNA
<213> ORGANISM: Artificial Sequence
<220> FEATURE:
<223> OTHER INFORMATION: siRNA antisense strand

<400> SEQUENCE: 14
```
cuagaaaggu gcaaacau                                                     18

<210> SEQ ID NO 15
<211> LENGTH: 31
<212> TYPE: RNA
<213> ORGANISM: Artificial Sequence
<220> FEATURE:
<223> OTHER INFORMATION: dsRNA

<400> SEQUENCE: 15
auguuugcac cuuucuaguu ccuuucuaaa g                                      31

<210> SEQ ID NO 16
<211> LENGTH: 18
<212> TYPE: RNA
<213> ORGANISM: Artificial Sequence
<220> FEATURE:
<223> OTHER INFORMATION: siRNA sense strand

<400> SEQUENCE: 16
ugagaggaga cagccagu                                                     18

<210> SEQ ID NO 17
<211> LENGTH: 18
<212> TYPE: RNA
<213> ORGANISM: Artificial Sequence
<220> FEATURE:
<223> OTHER INFORMATION: siRNA antisense strand

<400> SEQUENCE: 17
acuggcuguc uccucuca                                                     18

<210> SEQ ID NO 18
<211> LENGTH: 31
<212> TYPE: RNA
<213> ORGANISM: Artificial Sequence
<220> FEATURE:
<223> OTHER INFORMATION: dsRNA

<400> SEQUENCE: 18
ugagaggaga cagccaguuu ccuuucuaaa g                                      31

<210> SEQ ID NO 19
<211> LENGTH: 18
<212> TYPE: RNA
<213> ORGANISM: Artificial Sequence
<220> FEATURE:
<223> OTHER INFORMATION: siRNA sense strand

<400> SEQUENCE: 19
uucgguggua cguguac                                                      18

<210> SEQ ID NO 20
<211> LENGTH: 18
<212> TYPE: RNA
<213> ORGANISM: Artificial Sequence
<220> FEATURE:
<223> OTHER INFORMATION: siRNA antisense strand

<400> SEQUENCE: 20
guacaccgua ccaccgaa                                                     18

<210> SEQ ID NO 21
<211> LENGTH: 31
<212> TYPE: RNA

```
<213> ORGANISM: Artificial Sequence
<220> FEATURE:
<223> OTHER INFORMATION: dsRNA

<400> SEQUENCE: 21
uucgguggua cgguguacuu ccuuucuaaa g                              31

<210> SEQ ID NO 22
<211> LENGTH: 20
<212> TYPE: RNA
<213> ORGANISM: Artificial Sequence
<220> FEATURE:
<223> OTHER INFORMATION: siRNA sense strand

<400> SEQUENCE: 22
uccuuccaga gcagcugcaa                                           20

<210> SEQ ID NO 23
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 23
uugcagcugc ucuggaagga                                           20

<210> SEQ ID NO 24
<211> LENGTH: 29
<212> TYPE: RNA
<213> ORGANISM: Artificial Sequence
<220> FEATURE:
<223> OTHER INFORMATION: dsRNA

<400> SEQUENCE: 24
uccuuccaga gcagcugcaa uuucuaaag                                 29

<210> SEQ ID NO 25
<211> LENGTH: 19
<212> TYPE: RNA
<213> ORGANISM: Artificial Sequence
<220> FEATURE:
<223> OTHER INFORMATION: siRNA sense strand

<400> SEQUENCE: 25
ugugugacga gcccaagga                                            19

<210> SEQ ID NO 26
<211> LENGTH: 19
<212> TYPE: RNA
<213> ORGANISM: Artificial Sequence
<220> FEATURE:
<223> OTHER INFORMATION: siRNA antisense strand

<400> SEQUENCE: 26
uccuugggcu cgucacaca                                            19

<210> SEQ ID NO 27
<211> LENGTH: 28
<212> TYPE: RNA
<213> ORGANISM: Artificial Sequence
<220> FEATURE:
<223> OTHER INFORMATION: dsRNA

<400> SEQUENCE: 27
ugugugacga gcccaaggau uucuaaag                                  28
```

<210> SEQ ID NO 28
<211> LENGTH: 20
<212> TYPE: RNA
<213> ORGANISM: Artificial Sequence
<220> FEATURE:
<223> OTHER INFORMATION: siRNA sense strand

<400> SEQUENCE: 28
ugccuggucc agaccacaga                                               20

<210> SEQ ID NO 29
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 29
ucuguggucu ggaccaggca                                               20

<210> SEQ ID NO 30
<211> LENGTH: 33
<212> TYPE: RNA
<213> ORGANISM: Artificial Sequence
<220> FEATURE:
<223> OTHER INFORMATION: dsRNA

<400> SEQUENCE: 30
ugccuggucc agaccacaga uuccuuucua aag                                 33

<210> SEQ ID NO 31
<211> LENGTH: 18
<212> TYPE: RNA
<213> ORGANISM: Artificial Sequence
<220> FEATURE:
<223> OTHER INFORMATION: siRNA sense strand

<400> SEQUENCE: 31
caggcuagag aagcagag                                                 18

<210> SEQ ID NO 32
<211> LENGTH: 18
<212> TYPE: RNA
<213> ORGANISM: Artificial Sequence
<220> FEATURE:
<223> OTHER INFORMATION: siRNA antisense strand

<400> SEQUENCE: 32
cucugcuucu cuagccug                                                 18

<210> SEQ ID NO 33
<211> LENGTH: 27
<212> TYPE: RNA
<213> ORGANISM: Artificial Sequence
<220> FEATURE:
<223> OTHER INFORMATION: dsRNA

<400> SEQUENCE: 33
caggcuagag aagcagaguu ucuaaag                                       27

<210> SEQ ID NO 34
<211> LENGTH: 18
<212> TYPE: RNA
<213> ORGANISM: Artificial Sequence
<220> FEATURE:

<223> OTHER INFORMATION: siRNA sense strand

<400> SEQUENCE: 34
ugugcauggu caggccuu                                                   18

<210> SEQ ID NO 35
<211> LENGTH: 18
<212> TYPE: RNA
<213> ORGANISM: Artificial Sequence
<220> FEATURE:
<223> OTHER INFORMATION: siRNA antisense strand

<400> SEQUENCE: 35
aaggccugac caugcaca                                                   18

<210> SEQ ID NO 36
<211> LENGTH: 31
<212> TYPE: RNA
<213> ORGANISM: Artificial Sequence
<220> FEATURE:
<223> OTHER INFORMATION: dsRNA

<400> SEQUENCE: 36
ugugcauggu caggccuuuu ccuuucuaaa g                                    31

<210> SEQ ID NO 37
<211> LENGTH: 18
<212> TYPE: RNA
<213> ORGANISM: Artificial Sequence
<220> FEATURE:
<223> OTHER INFORMATION: siRNA sense strand

<400> SEQUENCE: 37
ugauuucagu agcacaag                                                   18

<210> SEQ ID NO 38
<211> LENGTH: 18
<212> TYPE: RNA
<213> ORGANISM: Artificial Sequence
<220> FEATURE:
<223> OTHER INFORMATION: siRNA antisense strand

<400> SEQUENCE: 38
cuugugcuac ugaaauca                                                   18

<210> SEQ ID NO 39
<211> LENGTH: 31
<212> TYPE: RNA
<213> ORGANISM: Artificial Sequence
<220> FEATURE:
<223> OTHER INFORMATION: dsRNA

<400> SEQUENCE: 39
ugauuucagu agcacaaguu ccuuucuaaa g                                    31

<210> SEQ ID NO 40
<211> LENGTH: 18
<212> TYPE: RNA
<213> ORGANISM: Artificial Sequence
<220> FEATURE:
<223> OTHER INFORMATION: siRNA sense strand

<400> SEQUENCE: 40
uagcgugcuc acugaccu                                                   18

```
<210> SEQ ID NO 41
<211> LENGTH: 18
<212> TYPE: RNA
<213> ORGANISM: Artificial Sequence
<220> FEATURE:
<223> OTHER INFORMATION: siRNA antisense strand

<400> SEQUENCE: 41
aggucaguga gcacgcua                                                 18

<210> SEQ ID NO 42
<211> LENGTH: 31
<212> TYPE: RNA
<213> ORGANISM: Artificial Sequence
<220> FEATURE:
<223> OTHER INFORMATION: dsRNA

<400> SEQUENCE: 42
uagcgugcuc acugaccuuu ccuuucuaaa g                                  31

<210> SEQ ID NO 43
<211> LENGTH: 20
<212> TYPE: RNA
<213> ORGANISM: Artificial Sequence
<220> FEATURE:
<223> OTHER INFORMATION: siRNA sense strand

<400> SEQUENCE: 43
cugauucgaa ugacacuguu                                               20

<210> SEQ ID NO 44
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 44
aacaguguca uucgaaucag                                               20

<210> SEQ ID NO 45
<211> LENGTH: 33
<212> TYPE: RNA
<213> ORGANISM: Artificial Sequence
<220> FEATURE:
<223> OTHER INFORMATION: dsRNA

<400> SEQUENCE: 45
cugauucgaa ugacacuguu uuccuuucua aag                                33

<210> SEQ ID NO 46
<211> LENGTH: 18
<212> TYPE: RNA
<213> ORGANISM: Artificial Sequence
<220> FEATURE:
<223> OTHER INFORMATION: siRNA sense strand

<400> SEQUENCE: 46
cagauuguuu gcaaaggg                                                 18

<210> SEQ ID NO 47
<211> LENGTH: 18
<212> TYPE: RNA
<213> ORGANISM: Artificial Sequence
<220> FEATURE:
<223> OTHER INFORMATION: siRNA antisense strand
```

-continued

```
<400> SEQUENCE: 47
cccuuugcaa acaaucug                                                   18

<210> SEQ ID NO 48
<211> LENGTH: 31
<212> TYPE: RNA
<213> ORGANISM: Artificial Sequence
<220> FEATURE:
<223> OTHER INFORMATION: dsRNA

<400> SEQUENCE: 48
cagauuguuu gcaaaggguu ccuuucuaaa g                                    31

<210> SEQ ID NO 49
<211> LENGTH: 18
<212> TYPE: RNA
<213> ORGANISM: Artificial Sequence
<220> FEATURE:
<223> OTHER INFORMATION: siRNA sense strand

<400> SEQUENCE: 49
gcaucagugu ccuuggca                                                   18

<210> SEQ ID NO 50
<211> LENGTH: 18
<212> TYPE: RNA
<213> ORGANISM: Artificial Sequence
<220> FEATURE:
<223> OTHER INFORMATION: siRNA antisense strand

<400> SEQUENCE: 50
ugccaaggac acugaugc                                                   18

<210> SEQ ID NO 51
<211> LENGTH: 31
<212> TYPE: RNA
<213> ORGANISM: Artificial Sequence
<220> FEATURE:
<223> OTHER INFORMATION: dsRNA

<400> SEQUENCE: 51
gcaucagugu ccuuggcauu ccuuucuaaa g                                    31

<210> SEQ ID NO 52
<211> LENGTH: 18
<212> TYPE: RNA
<213> ORGANISM: Artificial Sequence
<220> FEATURE:
<223> OTHER INFORMATION: siRNA sense strand

<400> SEQUENCE: 52
gacauuaacu cauuagac                                                   18

<210> SEQ ID NO 53
<211> LENGTH: 18
<212> TYPE: RNA
<213> ORGANISM: Artificial Sequence
<220> FEATURE:
<223> OTHER INFORMATION: siRNA antisense strand

<400> SEQUENCE: 53
gucuaaugag uuaauguc                                                   18

<210> SEQ ID NO 54
<211> LENGTH: 27
```

```
<212> TYPE: RNA
<213> ORGANISM: Artificial Sequence
<220> FEATURE:
<223> OTHER INFORMATION: dsRNA

<400> SEQUENCE: 54
gacauuaacu cauuagacuu ucuaaag                                              27

<210> SEQ ID NO 55
<211> LENGTH: 18
<212> TYPE: RNA
<213> ORGANISM: Artificial Sequence
<220> FEATURE:
<223> OTHER INFORMATION: siRNA sense strand

<400> SEQUENCE: 55
aacucauuag acuggaac                                                        18

<210> SEQ ID NO 56
<211> LENGTH: 18
<212> TYPE: RNA
<213> ORGANISM: Artificial Sequence
<220> FEATURE:
<223> OTHER INFORMATION: siRNA antisense strand

<400> SEQUENCE: 56
guuccagucu aaugaguu                                                        18

<210> SEQ ID NO 57
<211> LENGTH: 27
<212> TYPE: RNA
<213> ORGANISM: Artificial Sequence
<220> FEATURE:
<223> OTHER INFORMATION: dsRNA

<400> SEQUENCE: 57
aacucauuag acuggaacuu ucuaaag                                              27

<210> SEQ ID NO 58
<211> LENGTH: 18
<212> TYPE: RNA
<213> ORGANISM: Artificial Sequence
<220> FEATURE:
<223> OTHER INFORMATION: siRNA sense strand

<400> SEQUENCE: 58
acucauuaga cuggaacu                                                        18

<210> SEQ ID NO 59
<211> LENGTH: 18
<212> TYPE: RNA
<213> ORGANISM: Artificial Sequence
<220> FEATURE:
<223> OTHER INFORMATION: siRNA antisense strand

<400> SEQUENCE: 59
aguuccaguc uaaugagu                                                        18

<210> SEQ ID NO 60
<211> LENGTH: 27
<212> TYPE: RNA
<213> ORGANISM: Artificial Sequence
<220> FEATURE:
<223> OTHER INFORMATION: dsRNA

<400> SEQUENCE: 60
```

```
acucauuaga cuggaacuuu ucuaaag                                              27

<210> SEQ ID NO 61
<211> LENGTH: 18
<212> TYPE: RNA
<213> ORGANISM: Artificial Sequence
<220> FEATURE:
<223> OTHER INFORMATION: siRNA sense strand

<400> SEQUENCE: 61
uuagacugga acugaac                                                         18

<210> SEQ ID NO 62
<211> LENGTH: 18
<212> TYPE: RNA
<213> ORGANISM: Artificial Sequence
<220> FEATURE:
<223> OTHER INFORMATION: siRNA antisense strand

<400> SEQUENCE: 62
guucaaguuc cagucuaa                                                        18

<210> SEQ ID NO 63
<211> LENGTH: 27
<212> TYPE: RNA
<213> ORGANISM: Artificial Sequence
<220> FEATURE:
<223> OTHER INFORMATION: dsRNA

<400> SEQUENCE: 63
uuagacugga acugaacuu ucuaaag                                               27

<210> SEQ ID NO 64
<211> LENGTH: 18
<212> TYPE: RNA
<213> ORGANISM: Artificial Sequence
<220> FEATURE:
<223> OTHER INFORMATION: siRNA sense strand

<400> SEQUENCE: 64
auuagacugg aacugaa                                                         18

<210> SEQ ID NO 65
<211> LENGTH: 18
<212> TYPE: RNA
<213> ORGANISM: Artificial Sequence
<220> FEATURE:
<223> OTHER INFORMATION: siRNA antisense strand

<400> SEQUENCE: 65
uucaaguucc agucuaau                                                        18

<210> SEQ ID NO 66
<211> LENGTH: 27
<212> TYPE: RNA
<213> ORGANISM: Artificial Sequence
<220> FEATURE:
<223> OTHER INFORMATION: dsRNA

<400> SEQUENCE: 66
auuagacugg aacugaauu ucuaaag                                               27

<210> SEQ ID NO 67
<211> LENGTH: 18
<212> TYPE: RNA
<213> ORGANISM: Artificial Sequence
```

```
<220> FEATURE:
<223> OTHER INFORMATION: siRNA sense strand

<400> SEQUENCE: 67
cauuagacug gaacuuga                                          18

<210> SEQ ID NO 68
<211> LENGTH: 18
<212> TYPE: RNA
<213> ORGANISM: Artificial Sequence
<220> FEATURE:
<223> OTHER INFORMATION: siRNA antisense strand

<400> SEQUENCE: 68
ucaaguucca gucuaaug                                          18

<210> SEQ ID NO 69
<211> LENGTH: 27
<212> TYPE: RNA
<213> ORGANISM: Artificial Sequence
<220> FEATURE:
<223> OTHER INFORMATION: dsRNA

<400> SEQUENCE: 69
cauuagacug gaacuugauu ucuaaag                                27

<210> SEQ ID NO 70
<211> LENGTH: 18
<212> TYPE: RNA
<213> ORGANISM: Artificial Sequence
<220> FEATURE:
<223> OTHER INFORMATION: siRNA sense strand

<400> SEQUENCE: 70
ucauuagacu ggaacuug                                          18

<210> SEQ ID NO 71
<211> LENGTH: 18
<212> TYPE: RNA
<213> ORGANISM: Artificial Sequence
<220> FEATURE:
<223> OTHER INFORMATION: siRNA antisense strand

<400> SEQUENCE: 71
caaguuccag ucuaauga                                          18

<210> SEQ ID NO 72
<211> LENGTH: 27
<212> TYPE: RNA
<213> ORGANISM: Artificial Sequence
<220> FEATURE:
<223> OTHER INFORMATION: dsRNA

<400> SEQUENCE: 72
ucauuagacu ggaacuuguu ucuaaag                                27

<210> SEQ ID NO 73
<211> LENGTH: 19
<212> TYPE: RNA
<213> ORGANISM: Artificial Sequence
<220> FEATURE:
<223> OTHER INFORMATION: siRNA sense strand

<400> SEQUENCE: 73
gcaccagugu gaagacaua                                         19
```

<210> SEQ ID NO 74
<211> LENGTH: 19
<212> TYPE: RNA
<213> ORGANISM: Artificial Sequence
<220> FEATURE:
<223> OTHER INFORMATION: siRNA antisense strand

<400> SEQUENCE: 74
uaugucuuca cacuggugc                                                    19

<210> SEQ ID NO 75
<211> LENGTH: 18
<212> TYPE: DNA
<213> ORGANISM: Artificial Sequence
<220> FEATURE:
<223> OTHER INFORMATION: primer forward strand

<400> SEQUENCE: 75
gctcgtcgac aagggctc                                                     18

<210> SEQ ID NO 76
<211> LENGTH: 18
<212> TYPE: DNA
<213> ORGANISM: Artificial Sequence
<220> FEATURE:
<223> OTHER INFORMATION: primer reverse strand

<400> SEQUENCE: 76
caaacatgat ctgggtca                                                     18

<210> SEQ ID NO 77
<211> LENGTH: 20
<212> TYPE: DNA
<213> ORGANISM: Artificial Sequence
<220> FEATURE:
<223> OTHER INFORMATION: primer forward strand

<400> SEQUENCE: 77
caagggcctc ttctgtgact                                                   20

<210> SEQ ID NO 78
<211> LENGTH: 20
<212> TYPE: DNA
<213> ORGANISM: Artificial Sequence
<220> FEATURE:
<223> OTHER INFORMATION: primer reverse strand

<400> SEQUENCE: 78
ccgtcggtac atactccaca                                                   20

<210> SEQ ID NO 79
<211> LENGTH: 22
<212> TYPE: DNA
<213> ORGANISM: Artificial Sequence
<220> FEATURE:
<223> OTHER INFORMATION: primer forward strand

<400> SEQUENCE: 79
gcctcccttc ttgggtatgg aa                                                22

<210> SEQ ID NO 80
<211> LENGTH: 20
<212> TYPE: DNA
<213> ORGANISM: Artificial Sequence
<220> FEATURE:
<223> OTHER INFORMATION: primer reverse strand

<400> SEQUENCE: 80
cagctcagta acagtccgcc                                                  20

<210> SEQ ID NO 81
<211> LENGTH: 19
<212> TYPE: DNA
<213> ORGANISM: Artificial Sequence
<220> FEATURE:
<223> OTHER INFORMATION: primer forward strand

<400> SEQUENCE: 81
gggcctcttc tgcgatttc                                                   19

<210> SEQ ID NO 82
<211> LENGTH: 21
<212> TYPE: DNA
<213> ORGANISM: Artificial Sequence
<220> FEATURE:
<223> OTHER INFORMATION: primer reverse strand

<400> SEQUENCE: 82
atccaggcaa gtgcattggt a                                                21

<210> SEQ ID NO 83
<211> LENGTH: 20
<212> TYPE: DNA
<213> ORGANISM: Artificial Sequence
<220> FEATURE:
<223> OTHER INFORMATION: primer forward strand

<400> SEQUENCE: 83
gagcggagag tactggatcg                                                  20

<210> SEQ ID NO 84
<211> LENGTH: 20
<212> TYPE: DNA
<213> ORGANISM: Artificial Sequence
<220> FEATURE:
<223> OTHER INFORMATION: primer reverse strand

<400> SEQUENCE: 84
gttcgggctg atgtaccagt                                                  20

<210> SEQ ID NO 85
<211> LENGTH: 24
<212> TYPE: DNA
<213> ORGANISM: Artificial Sequence
<220> FEATURE:
<223> OTHER INFORMATION: primer forward strand

<400> SEQUENCE: 85
agctttgtgc aaagtggaac ctgg                                             24

<210> SEQ ID NO 86
<211> LENGTH: 24
<212> TYPE: DNA
<213> ORGANISM: Artificial Sequence
<220> FEATURE:
<223> OTHER INFORMATION: primer reverse strand

<400> SEQUENCE: 86
caaggtggct gcatcccaat tcat                                             24

<210> SEQ ID NO 87

```
<211> LENGTH: 16
<212> TYPE: DNA
<213> ORGANISM: Artificial Sequence
<220> FEATURE:
<223> OTHER INFORMATION: PNA antisense strand

<400> SEQUENCE: 87
ttagactgga acttga                                                       16

<210> SEQ ID NO 88
<211> LENGTH: 16
<212> TYPE: DNA
<213> ORGANISM: Artificial Sequence
<220> FEATURE:
<223> OTHER INFORMATION: PNA antisense strand

<400> SEQUENCE: 88
cattagactg gaactt                                                       16

<210> SEQ ID NO 89
<211> LENGTH: 16
<212> TYPE: DNA
<213> ORGANISM: Artificial Sequence
<220> FEATURE:
<223> OTHER INFORMATION: PNA antisense strand

<400> SEQUENCE: 89
tccagtctaa tgagtt                                                       16

<210> SEQ ID NO 90
<211> LENGTH: 16
<212> TYPE: DNA
<213> ORGANISM: Artificial Sequence
<220> FEATURE:
<223> OTHER INFORMATION: PNA antisense strand

<400> SEQUENCE: 90
ttccagtcta atgagt                                                       16

<210> SEQ ID NO 91
<211> LENGTH: 16
<212> TYPE: DNA
<213> ORGANISM: Artificial Sequence
<220> FEATURE:
<223> OTHER INFORMATION: PNA antisense strand

<400> SEQUENCE: 91
agttccagtc taatga                                                       16

<210> SEQ ID NO 92
<211> LENGTH: 16
<212> TYPE: DNA
<213> ORGANISM: Artificial Sequence
<220> FEATURE:
<223> OTHER INFORMATION: PNA antisense strand

<400> SEQUENCE: 92
tcaagttcca gtctaa                                                       16

<210> SEQ ID NO 93
<211> LENGTH: 16
<212> TYPE: DNA
<213> ORGANISM: Artificial Sequence
<220> FEATURE:
<223> OTHER INFORMATION: PNA antisense strand

<400> SEQUENCE: 93
```

```
ttcaagttcc agtcta                                                    16

<210> SEQ ID NO 94
<211> LENGTH: 16
<212> TYPE: DNA
<213> ORGANISM: Artificial Sequence
<220> FEATURE:
<223> OTHER INFORMATION: PNA antisense strand

<400> SEQUENCE: 94
caagttccag tctaat                                                    16

<210> SEQ ID NO 95
<211> LENGTH: 16
<212> TYPE: DNA
<213> ORGANISM: Artificial Sequence
<220> FEATURE:
<223> OTHER INFORMATION: PNA antisense strand

<400> SEQUENCE: 95
ttcaagttcc agtcta                                                    16

<210> SEQ ID NO 96
<211> LENGTH: 16
<212> TYPE: DNA
<213> ORGANISM: Artificial Sequence
<220> FEATURE:
<223> OTHER INFORMATION: PNA antisense strand

<400> SEQUENCE: 96
caagttccag tctaat                                                    16

<210> SEQ ID NO 97
<211> LENGTH: 16
<212> TYPE: DNA
<213> ORGANISM: Artificial Sequence
<220> FEATURE:
<223> OTHER INFORMATION: PNA antisense strand

<400> SEQUENCE: 97
tcaagttcca gtctaa                                                    16

<210> SEQ ID NO 98
<211> LENGTH: 16
<212> TYPE: DNA
<213> ORGANISM: Artificial Sequence
<220> FEATURE:
<223> OTHER INFORMATION: PNA antisense strand

<400> SEQUENCE: 98
agttccagtc taatga                                                    16

<210> SEQ ID NO 99
<211> LENGTH: 16
<212> TYPE: DNA
<213> ORGANISM: Artificial Sequence
<220> FEATURE:
<223> OTHER INFORMATION: PNA antisense strand

<400> SEQUENCE: 99
caagttccag tctaat                                                    16

<210> SEQ ID NO 100
<211> LENGTH: 10
<212> TYPE: RNA
```

-continued

```
<213> ORGANISM: Artificial Sequence
<220> FEATURE:
<223> OTHER INFORMATION: siRNA palindrome sequence

<400> SEQUENCE: 100
aacuugaacu                                                          10

<210> SEQ ID NO 101
<211> LENGTH: 4
<212> TYPE: PRT
<213> ORGANISM: Artificial Sequence
<220> FEATURE:
<223> OTHER INFORMATION: peptide conjugate binding to PNA end

<400> SEQUENCE: 101

Lys Lys Lys Lys
1

<210> SEQ ID NO 102
<211> LENGTH: 4
<212> TYPE: PRT
<213> ORGANISM: Artificial Sequence
<220> FEATURE:
<223> OTHER INFORMATION: peptide conjugate binding to PNA end

<400> SEQUENCE: 102

Arg Arg Arg Arg
1

<210> SEQ ID NO 103
<211> LENGTH: 25
<212> TYPE: PRT
<213> ORGANISM: Artificial Sequence
<220> FEATURE:
<223> OTHER INFORMATION: peptide conjugate binding to PNA end

<400> SEQUENCE: 103

Arg Arg Arg Arg Arg Arg Arg Gln Ile Lys Ile Trp Phe Gln Asn Arg
1               5                   10                  15

Arg Met Lys Trp Lys Lys Gly Gly Cys
            20                  25

<210> SEQ ID NO 104
<211> LENGTH: 16
<212> TYPE: PRT
<213> ORGANISM: Artificial Sequence
<220> FEATURE:
<223> OTHER INFORMATION: peptide conjugate binding to PNA end

<400> SEQUENCE: 104

Lys Lys Trp Lys Met Arg Arg Asn Gln Phe Trp Val Lys Val Gln Arg
1               5                   10                  15

<210> SEQ ID NO 105
<211> LENGTH: 27
<212> TYPE: PRT
<213> ORGANISM: Artificial Sequence
<220> FEATURE:
<223> OTHER INFORMATION: peptide conjugate binding to PNA end

<400> SEQUENCE: 105

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25
```

<210> SEQ ID NO 106
<211> LENGTH: 16
<212> TYPE: PRT
<213> ORGANISM: Artificial Sequence
<220> FEATURE:
<223> OTHER INFORMATION: peptide conjugate binding to PNA end

<400> SEQUENCE: 106

Arg Gln Ile Lys Ile Trp Phe Gln Asn Arg Arg Met Lys Trp Lys Lys
1               5                   10                  15

<210> SEQ ID NO 107
<211> LENGTH: 13
<212> TYPE: PRT
<213> ORGANISM: Artificial Sequence
<220> FEATURE:
<223> OTHER INFORMATION: peptide conjugate binding to PNA end

<400> SEQUENCE: 107

Gly Arg Lys Lys Arg Arg Gln Arg Arg Arg Pro Pro Gln
1               5                   10

<210> SEQ ID NO 108
<211> LENGTH: 18
<212> TYPE: DNA
<213> ORGANISM: Homo sapiens

<400> SEQUENCE: 108
ctcattagac tggaactt                                              18

<210> SEQ ID NO 109
<211> LENGTH: 18
<212> TYPE: DNA
<213> ORGANISM: Homo sapiens

<400> SEQUENCE: 109
ggaacttgaa ctgattca                                              18

<210> SEQ ID NO 110
<211> LENGTH: 20
<212> TYPE: DNA
<213> ORGANISM: Homo sapiens

<400> SEQUENCE: 110
ctgagtgact ctatatagct                                            20

<210> SEQ ID NO 111
<211> LENGTH: 19
<212> TYPE: DNA
<213> ORGANISM: Homo sapiens

<400> SEQUENCE: 111
gcatgaagac ataccgagc                                             19

<210> SEQ ID NO 112
<211> LENGTH: 18
<212> TYPE: DNA
<213> ORGANISM: Homo sapiens

<400> SEQUENCE: 112
atgtttgcac ctttctag                                              18

<210> SEQ ID NO 113
<211> LENGTH: 18

```
<212> TYPE: DNA
<213> ORGANISM: Homo sapiens

<400> SEQUENCE: 113
tgagaggaga cagccagt                                                 18

<210> SEQ ID NO 114
<211> LENGTH: 18
<212> TYPE: DNA
<213> ORGANISM: Homo sapiens

<400> SEQUENCE: 114
ttcggtggta cggtgtac                                                 18

<210> SEQ ID NO 115
<211> LENGTH: 20
<212> TYPE: DNA
<213> ORGANISM: Homo sapiens

<400> SEQUENCE: 115
tccttccaga gcagctgcaa                                               20

<210> SEQ ID NO 116
<211> LENGTH: 19
<212> TYPE: DNA
<213> ORGANISM: Homo sapiens

<400> SEQUENCE: 116
tgtgtgacga gcccaagga                                                19

<210> SEQ ID NO 117
<211> LENGTH: 20
<212> TYPE: DNA
<213> ORGANISM: Homo sapiens

<400> SEQUENCE: 117
tgcctggtcc agaccacaga                                               20

<210> SEQ ID NO 118
<211> LENGTH: 18
<212> TYPE: DNA
<213> ORGANISM: Homo sapiens

<400> SEQUENCE: 118
caggctagag aagcagag                                                 18

<210> SEQ ID NO 119
<211> LENGTH: 18
<212> TYPE: DNA
<213> ORGANISM: Homo sapiens

<400> SEQUENCE: 119
tgtgcatggt caggcctt                                                 18

<210> SEQ ID NO 120
<211> LENGTH: 18
<212> TYPE: DNA
<213> ORGANISM: Homo sapiens

<400> SEQUENCE: 120
tgatttcagt agcacaag                                                 18

<210> SEQ ID NO 121
```

-continued

```
<211> LENGTH: 18
<212> TYPE: DNA
<213> ORGANISM: Homo sapiens

<400> SEQUENCE: 121
tagcgtgctc actgacct                                                      18

<210> SEQ ID NO 122
<211> LENGTH: 20
<212> TYPE: DNA
<213> ORGANISM: Homo sapiens

<400> SEQUENCE: 122
ctgattcgaa tgacactgtt                                                    20

<210> SEQ ID NO 123
<211> LENGTH: 18
<212> TYPE: DNA
<213> ORGANISM: Homo sapiens

<400> SEQUENCE: 123
cagattgttt gcaaaggg                                                      18

<210> SEQ ID NO 124
<211> LENGTH: 18
<212> TYPE: DNA
<213> ORGANISM: Homo sapiens

<400> SEQUENCE: 124
gcatcagtgt ccttggca                                                      18

<210> SEQ ID NO 125
<211> LENGTH: 18
<212> TYPE: DNA
<213> ORGANISM: Homo sapiens

<400> SEQUENCE: 125
gacattaact cattagac                                                      18

<210> SEQ ID NO 126
<211> LENGTH: 18
<212> TYPE: DNA
<213> ORGANISM: Homo sapiens

<400> SEQUENCE: 126
aactcattag actggaac                                                      18

<210> SEQ ID NO 127
<211> LENGTH: 18
<212> TYPE: DNA
<213> ORGANISM: Homo sapiens

<400> SEQUENCE: 127
actcattaga ctggaact                                                      18

<210> SEQ ID NO 128
<211> LENGTH: 18
<212> TYPE: DNA
<213> ORGANISM: Homo sapiens

<400> SEQUENCE: 128
ttagactgga acttgaac                                                      18
```

```
<210> SEQ ID NO 129
<211> LENGTH: 18
<212> TYPE: DNA
<213> ORGANISM: Homo sapiens

<400> SEQUENCE: 129
attagactgg aacttgaa                                                 18

<210> SEQ ID NO 130
<211> LENGTH: 18
<212> TYPE: DNA
<213> ORGANISM: Homo sapiens

<400> SEQUENCE: 130
cattagactg gaacttga                                                 18

<210> SEQ ID NO 131
<211> LENGTH: 18
<212> TYPE: DNA
<213> ORGANISM: Homo sapiens

<400> SEQUENCE: 131
tcattagact ggaacttg                                                 18
```